US010913943B2

United States Patent
Streeter et al.

(10) Patent No.: US 10,913,943 B2
(45) Date of Patent: Feb. 9, 2021

(54) ENHANCED STEM CELL THERAPY AND STEM CELL PRODUCTION THROUGH THE ADMINISTRATION OF LOW LEVEL LIGHT ENERGY

(71) Applicant: Pthera LLC, Newark, DE (US)

(72) Inventors: Jackson Streeter, Newberry, FL (US); Luis De Taboada, Carlsbad, CA (US)

(73) Assignee: Pthera LLC, Newark, DE (US)

(*) Notice: Subject to any disclaimer, the term of this patent is extended or adjusted under 35 U.S.C. 154(b) by 46 days.

(21) Appl. No.: 16/190,229

(22) Filed: Nov. 14, 2018

(65) Prior Publication Data

US 2019/0078073 A1 Mar. 14, 2019

Related U.S. Application Data

(60) Division of application No. 12/846,560, filed on Jul. 29, 2010, now Pat. No. 10,683,494, and a continuation-in-part of application No. 12/817,090, filed on Jun. 16, 2010, now Pat. No. 9,993,659, which is a continuation-in-part of application No.
(Continued)

(51) Int. Cl.
*A61N 5/06* (2006.01)
*C12N 13/00* (2006.01)
*A61N 5/067* (2006.01)

(52) U.S. Cl.
CPC ........... *C12N 13/00* (2013.01); *A61N 5/0613* (2013.01); *A61N 5/0622* (2013.01); *A61N 2005/063* (2013.01); *A61N 2005/067* (2013.01); *A61N 2005/0647* (2013.01); *A61N 2005/0659* (2013.01)

(58) Field of Classification Search
CPC .................................. A61N 5/06; C12N 13/00
See application file for complete search history.

(56) References Cited

U.S. PATENT DOCUMENTS 3,735,755 A 5/1973 Eggleton et al.
3,810,367 A 5/1974 Peterson
(Continued)

FOREIGN PATENT DOCUMENTS

DE 3200584 7/1983
DE 4108328 9/1992
(Continued)

OTHER PUBLICATIONS

Agov et al., "On the mechanism of therapeutic action of helium-neon laser in ischemic heart disease", Klin Med, Oct. 1985, 63(10):102-105 (Abstract only).
(Continued)

*Primary Examiner* — Lynsey C Eiseman
(74) *Attorney, Agent, or Firm* — Fish & Richardson P.C.

(57) ABSTRACT

Methods of enhancing stem cell therapy through the administration of low level light energy are provided in several embodiments. Some embodiments comprise irradiating stem cells before or after implantation at a target tissue having loss of function due to damage or disease, with a resultant increase in the efficacy of the cell therapy. In some embodiments, light energy enhances one or more of the viability, proliferation, migration or engraftment of the stem cells, thereby enhancing the therapeutic effects of the irradiated cells during cell therapy.

9 Claims, 55 Drawing Sheets

Related U.S. Application Data

11/844,205, filed on Aug. 23, 2007, now Pat. No. 8,308,784, and a continuation-in-part of application No. 11/482,220, filed on Jul. 7, 2006, now abandoned, which is a continuation-in-part of application No. 10/682,379, filed on Oct. 9, 2003, now Pat. No. 7,303,578, and a continuation-in-part of application No. 10/287,432, filed on Nov. 1, 2002, now abandoned, application No. 16/190,229, which is a continuation-in-part of application No. 12/435,274, filed on May 4, 2009, now Pat. No. 8,025,687, which is a continuation-in-part of application No. 10/764,986, filed on Jan. 26, 2004, now Pat. No. 7,534,255.

(60) Provisional application No. 61/229,694, filed on Jul. 29, 2009, provisional application No. 60/840,370, filed on Aug. 24, 2006, provisional application No. 60/502,147, filed on Sep. 11, 2003, provisional application No. 60/487,979, filed on Jul. 17, 2003, provisional application No. 60/442,693, filed on Jan. 24, 2003, provisional application No. 60/369,260, filed on Apr. 2, 2002, provisional application No. 60/336,436, filed on Nov. 1, 2001, provisional application No. 60/537,190, filed on Jan. 19, 2004.

(56) References Cited

U.S. PATENT DOCUMENTS

| | | |
|---|---|---|
| 4,315,514 A | 2/1982 | Drewes et al. |
| 4,343,301 A | 8/1982 | Indech |
| 4,630,273 A | 12/1986 | Inoue et al. |
| 4,633,872 A | 1/1987 | Chaffee et al. |
| 4,669,466 A | 6/1987 | L'Esperance |
| 4,798,215 A | 1/1989 | Turner |
| 4,846,196 A | 1/1989 | Wiksell et al. |
| 4,850,351 A | 7/1989 | Herman et al. |
| 4,930,504 A | 6/1990 | Diamantopoulos et al. |
| 4,951,482 A | 8/1990 | Gilbert |
| 4,951,653 A | 8/1990 | Fry et al. |
| 4,966,144 A | 10/1990 | Rochkind et al. |
| 5,029,581 A | 7/1991 | Kaga et al. |
| 5,037,374 A | 8/1991 | Carol |
| 5,054,470 A | 10/1991 | Fry et al. |
| 5,150,704 A | 9/1992 | Tatebayashi et al. |
| 5,259,380 A | 11/1993 | Mendes et al. |
| 5,267,294 A | 11/1993 | Kuroda et al. |
| 5,282,797 A | 2/1994 | Chess |
| 5,358,503 A | 10/1994 | Bertwell et al. |
| 5,401,270 A | 3/1995 | Muller et al. |
| 5,441,495 A | 8/1995 | Liboff et al. |
| 5,445,146 A | 8/1995 | Bellinger |
| 5,445,608 A | 8/1995 | Chen et al. |
| 5,464,436 A | 11/1995 | Smith |
| 5,474,528 A | 12/1995 | Meserol |
| 5,501,655 A | 3/1996 | Rolt et al. |
| 5,511,563 A | 4/1996 | Diamond |
| 5,540,737 A | 7/1996 | Fenn |
| 5,580,550 A | 12/1996 | Gough et al. |
| 5,580,555 A | 12/1996 | Schwartz |
| 5,601,526 A | 2/1997 | Chapelon et al. |
| 5,616,140 A | 4/1997 | Prescott |
| 5,621,091 A | 4/1997 | Kunkel et al. |
| 5,622,168 A | 4/1997 | Keusch et al. |
| 5,627,870 A | 5/1997 | Kopecky |
| 5,640,978 A | 6/1997 | Wong |
| 5,643,334 A | 7/1997 | Eckhouse et al. |
| 5,707,396 A | 1/1998 | Benabid |
| 5,755,752 A | 5/1998 | Segal |
| 5,762,867 A | 6/1998 | D'Silva |
| 5,817,008 A | 10/1998 | Rafert et al. |
| 5,832,932 A | 11/1998 | Elsberry et al. |
| 5,842,477 A | 12/1998 | Naughton et al. |
| 5,843,073 A | 12/1998 | Sinofsky |
| 5,849,585 A | 12/1998 | Mather et al. |
| 5,871,521 A | 2/1999 | Kaneda et al. |
| 5,879,376 A | 3/1999 | Miller |
| 5,902,741 A | 5/1999 | Purchio et al. |
| 5,928,207 A | 7/1999 | Pisano et al. |
| 5,928,945 A | 7/1999 | Seliktar et al. |
| 5,954,762 A | 9/1999 | Di Mino et al. |
| 5,958,761 A | 9/1999 | Yogev et al. |
| 5,983,141 A | 11/1999 | Sluijter et al. |
| 5,989,245 A | 11/1999 | Prescott |
| 6,033,431 A | 3/2000 | Segal |
| 6,042,531 A | 3/2000 | Holcomb |
| 6,045,575 A | 4/2000 | Rosen et al. |
| 6,046,046 A | 4/2000 | Hassanein |
| 6,060,306 A | 5/2000 | Flatt et al. |
| 6,063,108 A | 5/2000 | Salansky et al. |
| 6,100,290 A | 8/2000 | Levy et al. |
| 6,107,325 A | 8/2000 | Chan et al. |
| 6,107,608 A | 8/2000 | Hayes |
| 6,112,110 A | 8/2000 | Wilk |
| 6,117,128 A | 9/2000 | Gregory |
| 6,129,748 A | 10/2000 | Kamei |
| 6,143,878 A | 11/2000 | Koopman et al. |
| 6,146,410 A | 11/2000 | Nagypal et al. |
| 6,156,028 A | 12/2000 | Prescott |
| 6,162,211 A | 12/2000 | Tankovich et al. |
| 6,179,771 B1 | 1/2001 | Muller |
| 6,179,830 B1 | 1/2001 | Kokubu |
| 6,187,210 B1 | 2/2001 | Lebouitz et al. |
| 6,210,317 B1 | 4/2001 | Bonlie |
| 6,214,035 B1 | 4/2001 | Streeter |
| 6,221,095 B1 | 4/2001 | Van Zuylen et al. |
| 6,253,097 B1 | 6/2001 | Aronow et al. |
| 6,267,780 B1 | 7/2001 | Streeter |
| 6,273,885 B1 | 8/2001 | Koop |
| 6,273,905 B1 | 8/2001 | Streeter |
| 6,277,974 B1 | 8/2001 | Lo et al. |
| 6,290,713 B1 | 9/2001 | Russell |
| 6,290,714 B1 | 9/2001 | Streeter |
| 6,306,130 B1 | 10/2001 | Anderson et al. |
| 6,312,451 B1 | 11/2001 | Streeter |
| 6,344,050 B1 | 2/2002 | Chen |
| 6,363,285 B1 | 3/2002 | Wey |
| 6,364,907 B1 | 4/2002 | Obochi et al. |
| 6,395,016 B1 | 5/2002 | Oron et al. |
| 6,397,107 B1 | 5/2002 | Lee et al. |
| 6,443,974 B1 | 9/2002 | Oron et al. |
| 6,443,978 B1 | 9/2002 | Zharov |
| 6,447,537 B1 | 9/2002 | Hartman |
| 6,471,716 B1 | 10/2002 | Pecukonis |
| 6,494,900 B1 | 12/2002 | Salansky et al. |
| 6,537,304 B1 | 3/2003 | Oron |
| 6,551,308 B1 | 4/2003 | Muller et al. |
| 6,571,735 B1 | 6/2003 | Wilkinson |
| 6,602,274 B1 | 8/2003 | Chen |
| 6,645,230 B2 | 11/2003 | Whitehurst |
| 6,663,659 B2 | 12/2003 | McDaniel |
| 6,665,562 B2 | 12/2003 | Gluckman et al. |
| 6,666,878 B2 | 12/2003 | Carlgren |
| 6,743,222 B2 | 6/2004 | Durkin et al. |
| 6,746,473 B2 | 6/2004 | Shanks et al. |
| 6,860,896 B2 | 3/2005 | Leber et al. |
| 6,918,922 B2 | 7/2005 | Oron |
| 7,041,094 B2 | 5/2006 | Conners |
| 7,066,929 B1 | 6/2006 | Azar et al. |
| 7,081,128 B2 | 7/2006 | Hart et al. |
| 7,118,563 B2 | 10/2006 | Weckwerth et al. |
| 7,303,578 B2 | 12/2007 | De Taboada et al. |
| 7,309,348 B2 | 12/2007 | Streeter et al. |
| 7,316,922 B2 | 1/2008 | Streeter |
| 7,534,255 B1 | 5/2009 | Streeter et al. |
| 7,575,589 B2 | 8/2009 | De Taboada et al. |
| 8,025,687 B2 | 9/2011 | Streeter et al. |
| 8,167,921 B2 | 5/2012 | Streeter et al. |
| 9,795,803 B2 | 10/2017 | Streeter et al. |
| 10,683,494 B2 | 6/2020 | Streeter et al. |
| 2002/0034796 A1* | 3/2002 | Shastri ............... C12N 5/0068 435/173.1 |
| 2002/0068927 A1 | 6/2002 | Prescot |

(56) References Cited

U.S. PATENT DOCUMENTS

| | | |
|---|---|---|
| 2002/0177885 A1 | 11/2002 | Eisfeld et al. |
| 2002/0188334 A1 | 12/2002 | Calgren |
| 2003/0004556 A1 | 1/2003 | McDaniel |
| 2003/0021124 A1 | 1/2003 | Elbrecht et al. |
| 2003/0023283 A1 | 1/2003 | McDaniel |
| 2003/0125782 A1 | 7/2003 | Streeter |
| 2003/0125783 A1 | 7/2003 | Moran |
| 2003/0144712 A1 | 7/2003 | Streeter |
| 2003/0167080 A1 | 9/2003 | Hart et al. |
| 2003/0181982 A1 | 9/2003 | Streeter |
| 2003/0212442 A1 | 11/2003 | Streeter |
| 2004/0132002 A1 | 7/2004 | Streeter |
| 2004/0153130 A1 | 8/2004 | Oron et al. |
| 2004/0153131 A1 | 8/2004 | Yorke |
| 2004/0220513 A1 | 11/2004 | Streeter |
| 2004/0260367 A1 | 12/2004 | Taboada et al. |
| 2005/0009161 A1 | 1/2005 | Streeter |
| 2005/0049452 A1 | 3/2005 | Lawlis et al. |
| 2005/0107851 A1 | 5/2005 | Taboada |
| 2005/0159793 A1 | 7/2005 | Streeter |
| 2005/0203595 A1 | 9/2005 | Oron |
| 2006/0206172 A1 | 9/2006 | DiMauro et al. |
| 2007/0179570 A1 | 8/2007 | De Taboada et al. |
| 2008/0125836 A1* | 5/2008 | Streeter ............ A61N 5/0618 607/89 |
| 2008/0221211 A1 | 9/2008 | Streeter |
| 2009/0254154 A1 | 10/2009 | De Taboada et al. |
| 2010/0055074 A1 | 3/2010 | Romanczyk et al. |
| 2010/0105977 A1 | 4/2010 | De Taboada et al. |
| 2010/0152820 A1 | 6/2010 | Anders et al. |
| 2010/0204762 A1 | 8/2010 | De Taboada et al. |
| 2010/0211136 A1 | 8/2010 | De Taboada et al. |
| 2011/0060266 A1 | 3/2011 | Streeter et al. |
| 2011/0144723 A1 | 6/2011 | Streeter et al. |

FOREIGN PATENT DOCUMENTS

| | | |
|---|---|---|
| DE | 4213053 | 10/1993 |
| DE | 29515096 | 1/1996 |
| EP | 0130950 | 4/1990 |
| EP | 0763371 | 3/1997 |
| EP | 0783904 | 7/1997 |
| EP | 1074275 | 2/2001 |
| EP | 1226787 | 7/2002 |
| JP | 5-212131 | 8/1993 |
| WO | WO 92/03964 | 3/1992 |
| WO | WO 96/36396 | 1/1997 |
| WO | WO 98/04321 | 2/1998 |
| WO | WO 98/22573 | 5/1998 |
| WO | WO 99/42178 | 8/1999 |
| WO | WO 99/46005 | 9/1999 |
| WO | WO 99/62599 | 12/1999 |
| WO | WO 00/35534 | 6/2000 |
| WO | WO 02/055149 | 7/2002 |
| WO | WO 02/098509 | 12/2002 |
| WO | WO 05/025672 | 3/2005 |
| WO | WO 2006/037236 | 4/2006 |
| WO | WO 2006/105254 | 10/2006 |

OTHER PUBLICATIONS

Belevich et al., "Exploring the proton pump mechanism of cytochrome c oxidase in real time," Proc Nat'l Acad. Sci., Feb. 20, 2007, 104:2685-2690.

Belevich et al., "Protoncoupled electron transfer drives the proton pump of cytochrome c oxidase," Nature, Apr. 2006, 440(7085):829-832.

Eells et al., "Therapeutic photobiomodulation for methanol-induced retinal toxicity," Proceedings National Academy of Science, Mar. 18, 2003, 100(6):3439-3444.

Gasparyan et al., "Influence of laser radiation on migration of stem cells, Mechanisms for Low-Light Therapy," Proc. of SPIE, Feb. 28, 2006, 6140:61400P, 6 pages.

Hou et al., "In Vitro Effects of Low-Level Laser Irradiation for Bone Marrow Mesenchymal Stem Cells: Proliferation, Growth Factors Secretion and Myogenic Differentiation", Lasers in Surgery and Medicine, Dec. 1, 2008, 40:726-733.

Karu et al., "Cell Attachment to Extracellular Matrices is Modulated by Pulsed Radiation at 820 nm and Chemicals that Modify the Activity of Enzymes in the Plasma Membrane," Lasers in Surgery and Medicine, Sep. 1, 2001, 29(3):274-281.

Karu in "Mechanisms of Low-Power Laser Light Action on Cellular Level", In Effects of Low-Power Light on Biological Systems V, Proceedings of SPIE, Nov. 3, 2000, 4159:1-17.

Karu, "Mechanisms of interaction of monochromatic visible light with cells," Proc. SPIE, Jan. 15, 1996, 2630:2-9.

Karu, "Photobiological Fundamentals of Low Power Laser Therapy," IEEE Journal of Quantum Electronics, Oct. 1987, 23:1703-1717.

Kavanagh et al., "Adult Mesenchymal Stem Cells—Intelligent Therapies for Immune Reprogramming," Intl. Drug Discovery, Jun./Jul. 2010:44-51.

Lapchak et al., "Transcranial Infrared Laser Therapy Improves Clinical Rating Scores After Embolic Strokes in Rabbits," Stroke, Aug. 1, 2004, 35(8):1985-1988.

Lepselter et al., "Biological and clinical aspects in laser hair removal," J. Dermatological Treatment, Apr. 1, 2004, 15(2):72-83.

Lisman et al., "Two Light-Induced Processes in the Photoreceptor Cells of Limulus Ventral Eye," J. Gen. Physiology, vol. 1971, 58:544-561.

Mvula et al., "The effect of low level laser irradiation on adult human adipose derived stem cells," Laser Med. Sci., Jul. 1, 2008, 23(3):277-282.

Shefer et al., "Low-energy Laser Irradiation Promotes the Survival and Cell Cycle Entry of Skeletal Muscle Satellite Cells," J. of Cell. Sci., Apr. 1, 2002, 115(7):1461-1469.

Shefer et al., "Primary Myogenic Cells See the Light: Improved Survival of Transplanted Myogenic Cells Following Low Energy Laser Irradiation," Lasers in Surgery and Medicine, Jan. 1, 2008, 40(1):38-45.

Tuchin in "Tissue Optics: Light Scattering Methods and Instruments for Medical Diagnosis," SPIE Press (2000), Bellingham, WA, pp. 3-11.

Van Brengel et al., "Power Density and Exposure Time of He—Ne Laser Irradiation Are More Important Than Total Energy Dose in Photo-Biomodulation of Human Fibroblasts in Vitro," Lasers In Surgery and Medicine, Jan. 1, 1992, 12(5):528-537.

Wells et al., "Biophysical mechanisms responsible for pulsed low-level laser excitation of neural tissue," Proc. SPIE, Mar. 1, 2006, 6084:60840X, 7 pages.

Wong-Riley et al., "Light-emitting diode treatment reverses the effect of TTX on cytochrome oxidase in neurons," NeuroReport, Oct. 8, 2001, 12(14):3033-3037.

Yaakobi et al., "Long-term effect of low energy laser irradiation on infarction and reperfusion injury in the rat heart," J. Appl. Physiol., Jun. 1, 2001, 90(6):2411-2419.

\* cited by examiner

ENHANCED STEM CELL THERAPY AND STEM CELL PRODUCTION THROUGH THE ADMINISTRATION OF LOW LEVEL LIGHT ENERGY

RELATED APPLICATIONS

This application is a divisional of and claims the benefit under 35 U.S.C. § 120 of U.S. patent application Ser. No. 12/846,560, filed on Jul. 29, 2010, which claims the benefit under 35 U.S.C. § 119(e) of U.S. Provisional Appl. 61/229,694, filed Jul. 29, 2009 and is a continuation-in-part of U.S. patent application Ser. No. 12/817,090 filed on Jun. 16, 2010, which is a continuation-in-part of U.S. patent application Ser. No. 11/844,205 filed on Aug. 23, 2007, which claims the benefit under 35 U.S.C. § 119(e) of U.S. Provisional Application No. 60/840,370, filed Aug. 24, 2006; this application is also a continuation-in-part of U.S. patent application Ser. No. 11/482,220, filed on Jul. 7, 2006, which is a continuation of U.S. patent application Ser. No. 10/682,379, filed on Oct. 9, 2003, now U.S. Pat. No. 7,303,578, which claims the benefit under 35 U.S.C. § 119(e) of U.S. Provisional Application Nos. 60/502,147, filed Sep. 11, 2003, 60/487,979, filed Jul. 17, 2003, and 60/442,693, filed Jan. 24, 2003; U.S. patent application Ser. Nos. 10/682,379 and 11/482,220 each are a continuation-in-part of U.S. patent application Ser. No. 10/287,432, filed on Nov. 1, 2002, now abandoned, which claims the benefit under 35 U.S.C. § 119(e) of U.S. Provisional Application Nos. 60/369,260, filed Apr. 2, 2002 and 60/336,436, filed Nov. 1, 2001; this application is also a continuation-in-part of U.S. patent application Ser. No. 12/435,274, filed May 4, 2009, which is a continuation of U.S. patent application Ser. No. 10/764,986, filed Jan. 26, 2004, now U.S. Pat. No. 7,534,255, which claims the benefit under 35 U.S.C. § 119(e) of U.S. Provisional Application Nos. 60/537,190, filed Jan. 19, 2004, 60/487,979, filed Jul. 17, 2003, and 60/442,693, filed Jan. 24, 2003, all incorporated by reference in their entireties herein.

BACKGROUND

Field of the Invention

The present application relates to systems and methods for enhancing the efficacy of various aspects of stem cell therapy. Several embodiments are directed to enhancing one or more of the isolation, proliferation, delivery, engraftment, differentiation, or function of stem cells. Several embodiments are directed to enhancing neurologic function in individuals having a loss of one or more neurologic functions, including but not limited to, motor function, cognitive function, including that resulting from injury, neurological disorders, normal age-related degeneration, etc. Other embodiments are directed to improving the viability or culturability of stem cells to be used in stem cell therapy or research.

Description of the Related Art

The scope of human disease that involves loss of or damage to cells is vast and includes, but is not limited to, cancers, ocular disease, neurodegenerative disease, endocrine diseases, and cardiovascular disease. The result of these diseases is typically some degree of loss of function of particular cells, and possibly an entire organ. This may lead to compromised quality of life, disability, or death. Injury or trauma to these cells or organs may yield similar effects.

Cell therapy involves the use of cells, and in some cases fetal, umbilical cord, placenta-derived, adult, induced pluripotent, or human embryonic stem cells and/or their partially or fully differentiated cellular derivatives to treat diseased or damaged tissues via replacement or regeneration. It is rapidly coming to the forefront of technologies that are poised to treat many diseases, in particular those that affect individuals who are non-responsive to traditional pharmacologic therapies. In some cases, cell therapy may be used prior to, or in response to, a therapy that itself induces damage to cells or tissues.

By way of example, bone marrow contains hematopoietic stem cells (HSC), which are precursor cells not dedicated to any particular blood cell lineage. Upon stimulation by particular cytokines the HSC may become committed to differentiating into cells of a particular lineage. Neutrophils, which are the predominant circulating white blood cells and account for nearly 70% of the total white cell count (normal range of $4 \times 10^9$ to $11 \times 10^9$ white blood cells/L of blood), are formed when HSC become committed to the granulocyte and/or macrophage lineage. Granulocyte colony-stimulating factor (G-CSF) is one example of a molecule that can induce the HSC to commit to forming neutrophils.

G-CSF (e.g., filgrastim, NEUPOGEN® by Amgen) is a cytokine produced by vascular endothelium and multiple types of immune cells. A G-CSF receptor (G-CSF-R) is present on HSC in the bone marrow. Upon binding to the G-CSF-R, G-CSF stimulates the proliferation of HSC and their differentiation into mature granulocytes, such as neutrophils. G-CSF is also a potent inducer of HSC mobilization and differentiation from the bone marrow into the bloodstream. G-CSF exists naturally, and synthetic forms have been also been developed for clinical use. Other hematopoietic stem cell stimulator/mobilizers are also available, such as Plerixafor (AMD3100, MOBOZIL® by Genzyme Corporation), a CXCR4 alpha-chemokine receptor modulator, that functions to stimulate the HSCs from the bone marrow to the periphery. Synergy between Plerixafor and G-CSF is possible. Granulocyte-macrophage colony stimulating factor (GM-CSF) is another cytokine that can promote differentiation of HSCs into neutrophils.

In normal humans, approximately one hundred billion neutrophils are produced daily and function as the primary defense against bacterial infections. Inactive neutrophils circulate in the blood stream with a half-life of about 12 hours. When activated, the circulating neutrophils are recruited to infected or inflamed tissues where they can internalize and kill a variety of microbes. Active neutrophils survive for approximately 1-2 days in the tissue and serve to prevent or reduce the likelihood of a large scale infection.

After their functional life-span has elapsed, neutrophils are typically destroyed by apoptosis, a sort of pre-programmed cell death. Circulating neutrophils counts are a result of the balance of neutrophil production and death. Neutropenia is a hematological disorder characterized by an abnormally low number of neutrophils (neutrophil granulocyte count below $0.5 \times 10^9$/litre). Neutropenia can result from either decreased production or accelerated destruction of neutrophils. Neutropenic individuals are more susceptible to infections, including bacterial, fungal, and parasitic infections, with effects ranging from simple fevers to life-threatening sepsis.

Alterations in neutrophil homeostasis may result from autoimmune or hereditary disorders, cancers, particularly those affecting the blood cells, such as Hodgkin's disease or Non-Hodgkin lymphomas, stress, such as from surgery or trauma, or medication, such as chemotherapeutic agents. Some medications may also have agranulocytosis as a side effect, such as, for example, antiepileptics, antithyroid drugs (carbimazole, methimazole, and propylthiouracil), antibiotics (penicillin, chloramphenicol and co-trimoxazole), cytotoxic drugs, gold, NSAIDs (indomethacin, naproxen, phenylbutazone), mebendazole, the antidepressant mirtazapine, and some antipsychotics (the atypical antipsychotic clozapine). Some conditions may cause impaired neutrophil function without necessarily decreasing the quantitative number of neutrophils. This can be attributable to certain medications, such as steroids, alcoholism, or conditions such as diabetes, end-stage liver or renal disease, or immune disorders such as HIV.

Hodgkin's disease (HD) is a lymphoma, a hematological cancer that originates from uncontrolled growth of a subtype of white blood cells known as lymphocytes. Treatment for HD typically involves radiation therapy, chemotherapy, or a combination of the two. Non-Hodgkin lymphomas (NHLs) are those lymphomas that are not classified as HD. Numerous classes of NHLs exist and they vary greatly in their aggressiveness. Thus, therapy for NHLs is tailored to the particular classification, but generally involves combinations of chemotherapy, immunotherapy, and radiation therapy.

In a broad sense, cancer is the rapid, uncontrolled growth of cells. Most chemotherapeutic agents act by inhibiting cell division, effectively targeting the fast-dividing cancer cells. However, there is currently no known cancer cell specific marker that targets the chemotherapeutic agents to cancerous cells. As a result, many normal cells, such as rapidly produced blood cells like neutrophils can also be affected. In combination with additional damaging effects on bone marrow and the subsequent drop in white blood cell production, virtually all chemotherapeutic regimes can cause suppression of the immune system due to neutropenia. It is therefore evident that when the chemotherapy is targeted to blood cells, as in HD and NHLs, the risk of neutropenia is even greater.

While there is no ideal therapy for neutropenia, several approaches have evolved to address neutropenia in the cancer treatment setting. When doses of chemotherapy are relatively low, the bone marrow may remain viable and marginally functional. In these cases, G-CSF and/or administration of other agents concurrent with chemotherapy may be used to combat neutropenia through the increased production of neutrophils. However, when higher doses of chemotherapy are needed, G-CSF may be used prior to chemotherapy to stimulate proliferation of HSC, which can be harvested and later transplanted back into the patient. While these approaches have produced positive results, increasing production of HSC and neutrophils in cancer patients remain major hurdles.

SUMMARY

Several embodiments of the invention provide methods for the efficient production of hematopoietic stem cells and the treatment of neutropenia. Several embodiments further provide methods for isolating, mobilizing, stimulating, proliferating, or otherwise enhancing the effects of other types of stem cells. In one embodiment, the therapeutic effect of stem cells that are used in cell therapy is enhanced.

In several embodiments of the invention, a method for enhancing the suitability of stem cells (e.g., neural) for use in cell therapy using low level light therapy (LLLT) is provided. In some embodiments, the method comprises obtaining a population of stem cells, providing a LLLT device having a light emitting surface that emits light energy, delivering light energy to the stem cells, wherein the light energy increases one or more of the viability, proliferation, differentiation, migration, or engraftment of the stem cells, thereby enhancing the suitability of the stem cells for use in cell therapy. In one embodiment, the invention enhances the suitability of neural stem cells for use in neural cell therapy, including but not limited to cell therapy targeted for brain tissue, spinal cord and other central and peripheral nervous system tissue.

In several embodiments, a method for enhancing the efficacy of stem cell therapy in a mammal using LLLT is provided. In one embodiment, the method comprises identifying a mammal having a tissue with impaired function, administering one or more stem cells to the tissue, providing a LLLT device having a light emitting surface that emits light energy, and delivering light energy to the tissue, wherein the light energy enhances one or more of the viability, engraftment, proliferation, migration, or differentiation of the administered stem cells, thereby enhancing the efficacy of the stem cell therapy.

In several embodiments, a method for improving the efficiency of one or more peripheral collections of stem cells in a mammal using LLLT and a stem cell mobilizing compound is provided. In some embodiments, the method comprises administering a stem cell stimulating or mobilizing compound to a mammal, providing a LLLT device having a light emitting surface that emits light energy, and delivering light energy to at least one long bone of the mammal, thereby increasing the mobilization of stem cells from the bone marrow to the peripheral blood of the mammal. In several embodiments the stem cell stimulating or mobilizing compound works synergistically with the light energy to stimulate bone marrow within the long bone, thereby increasing the mobilization of stem cells from the bone marrow to the peripheral blood of the mammal and improving the efficiency of peripheral collection of stem cells.

In some embodiments, the light energy has a wavelength between about 350 nm and 1200 nm. In some embodiments, the light energy has a wavelength between about 500 nm and 1000 nm. In some embodiments, the light energy has a wavelength between about 670 and 900 nm (e.g., 670, 700, 730, 760, 790, 800, 810, 830, 850, 870, 900 nm). Depending on the target tissue, longer or shorter wavelengths are used. In one embodiment, the light energy has a time averaged irradiance at or within about one centimeter of the stem cells of at least about 0.01 mW/cm$^2$. In one embodiment, the light energy has a time averaged irradiance at or within about one centimeter of the stem cells of about 20 mW/cm$^2$ to about 60 mW/cm$^2$ (e.g., 20, 30, 40, 50, or 60 mW/cm$^2$). In one embodiment, the light energy has a time averaged irradiance at or within about one centimeter of the stem cells of about 50 mW/cm$^2$. Depending on the target tissue (and the amount of overlying light energy absorbing and/or reflecting tissue), greater or lesser time averaged irradiances are used.

In several embodiments, the light energy is delivered continuously. In several embodiments, the light energy is delivered in pulses. In some embodiments, the light energy is delivered in pulses at a frequency ranging from about 80 to about 120 Hz. Depending on the target tissue (and the amount of overlying light energy absorbing and/or reflecting tissue), lower or higher frequencies are used. In some embodiments, the pulsing frequency is adjusted over time to tailor the therapy to the characteristics of a particular patient (e.g., frequency adjustment based on patient responsiveness to cell therapy). In some embodiments, combinations of continuous and pulsed light parameters are used.

In some embodiments, the light energy is delivered to the stem cells in vitro, while in some embodiments, the light energy is delivered to the stem cells in vivo (e.g., post administration to a cell therapy subject). In still other embodiments, light energy is administered both in vitro and in vivo. In several embodiments, an ongoing regime of light energy administration is used (e.g., daily, twice daily administration, either in vitro, in vivo, or both). Many varied patterns of LLLT administration are used, based on the specific disease or injury, and cell type being used for cell therapy.

In several embodiments, the stem cells are derived from one of a variety of stem cell sources consisting of adult stem cells, embryonic stem cells, placenta-derived stem cells, bone marrow-derived stem cells, mesenchymal stem cells, adipose stem cells, and induced pluripotent stem cells. In some embodiments, the stem cells are differentiated to a desired lineage (e.g., neural) prior to administration to a cell therapy subject. In several embodiments, the stem cells are neural stem cells. In other embodiments, the stem cells differentiate in vivo after administration to a cell therapy subject. In some embodiments, in vitro differentiation is not complete (e.g., the cells are not terminally differentiated), but are lineage committed.

In several embodiments, the administered stem cells are autologous with respect to the recipient. In other embodiments, the stem cells are allogeneic with respect to the recipient. In one embodiment, mesenchymal stem cells are used in allogeneic transplants due to the ability of the cells to modulate the immune response in the target tissue. In one embodiment, the stem cells alter T-cell or antigen presenting cell function, thereby reducing immunologic rejection of transplanted cells. In one embodiment, the stem cells additionally reduce fibrosis in the target tissue.

In several embodiments, the stem cells are for use in cell therapy to treat a neurological disease or injury. For example, in some embodiments, the tissue with impaired function is neural tissue having impaired function due to degenerative neural disease. In some embodiments, the stem cells are administered to a subject for the treatment of Parkinson's disease. In some embodiments, other degenerative diseases, such as dopaminergic impairment, Alzheimer's, amyotrophic lateral sclerosis, Huntington's disease, and/or dementia are treated. In several embodiments, impaired neural function is a result of injury to the neurons. In one embodiment, LLLT and cell therapy are used to treat the damage due to stroke. In one embodiment, cerebral ischemia (including focal cerebral ischemia), traumatic brain injury, and/or physical trauma such as crush or compression injury in the CNS, including a crush or compression injury of the brain, spinal cord, nerves or retina, is treated.

In several embodiments, neutropenia is treated using LLLT and a stem cell mobilizing compound by stimulating release of stem cells to the peripheral blood for later readministration to the patient (or another patient) in order to repopulate dwindling cell numbers due to disease. In some embodiments, such methods are used to treat Non-Hodgkin lymphoma, Hodgkin's disease, cancer, or a side-effect of a therapy for Non-Hodgkin lymphoma, Hodgkin's disease, or cancer.

In several embodiments, stem cells are mobilized, collected, and administered to treat other diseases. For example, in some embodiments, mobilized mesenchymal stem cells are differentiated to a pancreatic lineage and used to recapitulate insulin secretion in a diabetic subject. In one embodiment, LLLT is used to assist in mobilizing the cells, while in one embodiment, LLLT is used in the cell therapy itself. In still another embodiment, LLLT is used both in the mobilization and in the cell therapy aspects of treatment.

In certain embodiments, a method for improving hematopoietic stem cell (HSC) production and mobilization in a patient comprises administering a therapeutically-effective amount of a therapeutic agent configured to increase the quantity of in the bloodstream and/or improve the function of a particular type of cell in the body, such as, for example, granulocyte colony-stimulating factor (G-CSF) to the patient in conjunction with a therapeutically effective amount of electromagnetic radiation (e.g. LLLT). In certain embodiments, at least a portion of the therapeutically-effective amount of electromagnetic radiation is applied concurrently with the administration of the therapeutically-effective amount of G-CSF.

In some embodiments, a method for preventing neutropenia comprises administering a therapeutically-effective amount of G-CSF to the patient in conjunction with a therapeutically effective amount of electromagnetic radiation. In certain embodiments, at least a portion of the therapeutically-effective amount of electromagnetic radiation is applied concurrently with the administration of the therapeutically-effective amount of G-CSF. In certain such embodiments, the neutropenia may result from cancer or therapies to be used in treating the cancer.

In other embodiments, a method for treating neutropenia comprises administering a therapeutically-effective amount of G-CSF to the patient in conjunction with a therapeutically effective amount of electromagnetic radiation. In certain embodiments, at least a portion of the therapeutically-effective amount of electromagnetic radiation is applied concurrently with the administration of the therapeutically-effective amount of G-CSF. In certain such embodiments, the neutropenia is a result of cancer or therapies used to treat the cancer.

In some embodiments, there is provided a method for treating damage or illness in the central nervous system in a mammal or human, comprising delivering an effective amount of light energy to an in vitro culture comprising progenitor cells, and implanting the cells into the central nervous system of a mammal or human, wherein delivering an effective amount of light energy includes delivering light having a wavelength in the visible to near-infrared wavelength range and a power density of at least about 0.01 mW/cm$^2$ to the cells in culture. The progenitor cells may be treated with another therapeutic agent, for example a pharmaceutical compound or biologic prior to implantation. Without being bound by theory or a specific mechanism, the agent or combination of agents may have the effect of stimulating or mobilizing progenitor cells.

In some embodiments, there is provided a method for treating damage or degeneration in non-neural tissue, for example skeletal muscle, the method comprising delivering an effective amount of light energy to an in vitro culture comprising progenitor cells. Delivering an effective amount of light energy includes delivering light having a wavelength in the visible to near-infrared wavelength range and a power density of at least about 0.01 mW/cm$^2$ to the cells in culture. The site of implantation is chosen to permit the implanted cells to regenerate the damaged tissue, for example by directly repopulating the damaged or degenerating tissue, or by supporting the growth or proliferation of endogenous cells. The site of implantation may also be irradiated by laser light having a wavelength in the visible to near-infrared wavelength range and a power density of at least about 0.01 mW/cm$^2$.

In accordance with some embodiments there are provided methods directed toward the enhancement of neurologic function in a subject. The methods include delivering a neurologic enhancing effective amount of a light energy having a wavelength in the visible to near-infrared wavelength range to at least one area of the brain of a subject. In a preferred embodiment delivering the neurologic function enhancing effective amount of light energy includes delivering a predetermined power density of light energy through the skull to the target area of the brain and/or delivering light energy through the skull to at least one area of the brain of a subject, wherein the wavelength, power density and amount of the light energy delivered are sufficient to cause an enhancement of neurologic functioning.

The low level light therapy methods for enhancing neurologic function are based in part on the new and surprising discovery that power density (i.e., power per unit area) of the light energy applied to tissue appears to be a very important factor in determining the relative efficacy of low level light therapy, and particularly with respect to enhancing the function of neurons in both healthy and diseased states.

In accordance with one embodiment there is provided a method for preventing heat stroke in a subject. The term "preventing" in this context shall be given its ordinary meaning and shall include reducing the severity of a later heat stroke in a subject that has undergone treatment, reducing the incidence of heat stroke in individuals who have undergone treatment, as well as reducing the likelihood of onset heat stroke in a subject that has undergone treatment. In one embodiment, the method comprises delivering light energy having a wavelength in the visible to near-infrared wavelength range through the skull to at least one area of the brain of a subject, wherein the wavelength, power density and amount of the light energy delivered are sufficient to prevent, reduce the severity, or reduce the incidence of heat stroke in the subject.

In several embodiments, the target area of the brain may be all of the brain or a specific area of the brain including, but not limited to, an area associated with a particular cognitive or motor function, an area exhibiting neurodegeneration, the cortex, and/or an area that has been affected by trauma. The subject may have a cognitive or motor impairment such as from neurodegeneration or the subject may be normal.

In accordance with another embodiment, there is provided a method of increasing the production of ATP by neurons to increase neurologic function. The method comprises irradiating neurons with light energy having a wavelength in the near infrared to visible portion of the electromagnetic spectrum for at least about 1 second, where the power density of the light energy at the neurons is at least about 0.01 mW/cm$^2$.

In certain embodiments, a method of treating a patient having neurologic function affected by Parkinson's disease is provided. The method comprises providing a patient having neurologic function affected by Parkinson's disease. The method further comprises delivering electromagnetic radiation noninvasively through the scalp and the skull of the patient to at least one portion of the brain of the patient. The light energy has a wavelength in the visible to near-infrared wavelength range, and the wavelength, power density (or irradiance), and amount of the light energy delivered to the at least one portion of the brain are sufficient to reduce the severity of symptoms of Parkinson's disease in the patient.

In several embodiments, the predetermined power density is a power density of at least about 0.01 mW/cm$^2$. The predetermined power density in preferred embodiments is typically selected from the range of about 0.01 mW/cm$^2$ to about 100 mW/cm$^2$, including from about 0.01 mW/cm$^2$ to about 15 mW/cm$^2$ and from about 2 mW/cm$^2$ to about 50 mW/cm$^2$. In some embodiments, power densities above or below these values may be used.

In some embodiments, the methods encompass using light energy having a wavelength of about 630 nm to about 904 nm, and in one embodiment the light energy has a wavelength of about 780 nm to about 840 nm. The light energy is preferably from a coherent source (i.e. a laser), but light from non-coherent sources may also be used.

In some embodiments, the methods encompass placing a light source in contact with a region of skin that is either adjacent an area of the brain in which treatment is desired, contralateral to such area, or a combination of the foregoing, and then administering the light energy, including the neurologic function enhancing effective amount of light energy, as may be measured by power density, to the area of the brain. In delivering the light, the power density may be a predetermined power density. Some preferred methods encompass determining a surface power density of the light energy sufficient for the light energy to penetrate the skull. The determination of the required surface power density, which is relatively higher than the power density to be delivered to the brain tissue being treated, takes into account factors that attenuate power density as it travels through tissue, including skin pigmentation, and location of the brain area being treated, particularly the distance of the brain area from the skin surface where the light energy is applied.

In certain embodiments, a method of treating or preventing Parkinson's disease is provided. The method comprises noninvasively irradiating at least a portion of a patient's brain with electromagnetic radiation transmitted through the scalp. The electromagnetic radiation has a power density (or irradiance), between 0.01 mW/cm$^2$ and 100 mW/cm$^2$ at a depth of approximately 2 centimeters below the dura.

In certain embodiments, a method of treating a patient is provided. The method comprises delivering electromagnetic radiation noninvasively through the scalp and the skull to at least one portion of the brain of the patient. The light energy has a wavelength in the visible to near-infrared wavelength range, and the wavelength, power density, and amount of the light energy delivered to the at least one portion of the brain are sufficient to prevent, reduce the severity, or reduce the incidence of Parkinson's disease in the patient.

In certain embodiments, a method of preventing Parkinson's disease in a patient is provided. The method comprises providing a patient having a predisposition towards contracting Parkinson's disease. The method further comprises delivering electromagnetic radiation noninvasively through the scalp and the skull of the patient to at least one portion of the brain of the patient. The light energy has a wavelength in the visible to near-infrared wavelength range, and the wavelength, power density, and amount of the light energy delivered to the at least one portion of the brain are sufficient to reduce a probability of the patient contracting Parkinson's disease.

In certain embodiments, a method of treating the central nervous system of a patient is provided. The method comprises identifying a patient exhibiting symptoms of damage to the central nervous system due to Parkinson's disease.

The method further comprises irradiating an in vitro culture comprising progenitor cells with electromagnetic radiation having a wavelength in the visible to near-infrared wavelength range and a power density of at least about 0.01 mW/cm$^2$. The method further comprises implanting the irradiated cells into the central nervous system of the patient.

BRIEF DESCRIPTION OF THE FIGURES

FIG. 42 shows a hand-held laser device irradiating the long bone (femur) of the upper leg of a patient.

DETAILED DESCRIPTION

Figure 1:
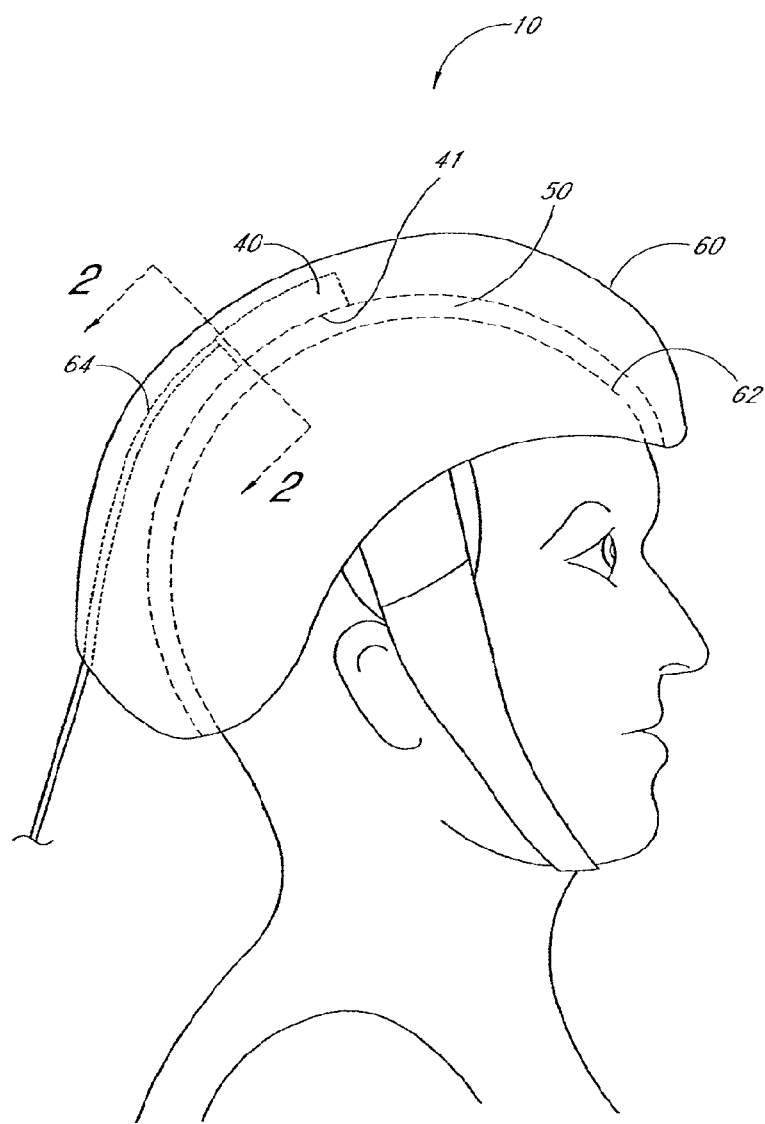
FIG. 1 schematically illustrates a therapy apparatus comprising a cap which fits securely over the patient's head.

As discussed above, injury and/or disease can result in the loss of function or death of cells in a tissue afflicted with or indirectly impacted by the disease or injury. For example, age-related degeneration of tissues can lead to loss of function of neurons in the eye, loss of tactile sensations, reduced control over muscle movement, memory failure, among many other possible effects. Non-neural tissues are also subject to damage or disease. For example, cardiac tissue may be damaged after an adverse myocardial event, such as a myocardial infarction or stroke. As discussed above, blood cells may be damaged by chemotherapy or radiation therapy. Liver cells may be damaged by toxins or metabolic waste by products. These diseases and/or injuries, among others, are all candidates for cell therapy.

Cell therapy, the introduction of new cells into a tissue in order to treat a disease, represents a possible method for repairing or replacing diseased tissue with healthy tissue.

In several embodiments described herein, low level laser therapy, also referred to as low level light therapy ("LLLT") is used to augment the effects of cell therapy. As described in more detail below, LLLT is used in several embodiments to enhance the viability of stem cells. In several embodiments, enhanced viability is manifest as a more robust population of cells to transplant into a subject requiring cellular therapy. In some embodiments, stem cells exposed to LLLT proliferate to a greater degree, have enhance survival post-implantation, have increased differentiation, and the like. In some embodiments, LLLT enhances the activation and differentiation of endogenous stem cells. In some embodiments, LLLT is used to treat harvested stem cells (or cultured stem cells) prior to administration to an individual requiring therapy. In some embodiments, stem cells are administered and then LLLT is employed. In some embodiments, cells are administered without previously exposing the cells the LLLT (e.g., cells not exposed until after administration). In some embodiments, a target tissue is pre-treated to LLLT prior to administration of cells (which either have or have not yet been treated with LLLT). In several embodiments, cells are treated with LLLT, then incubated for a period of time prior to administration. For example, the incubation period ranges from a one or more minutes to about 48 hours, in some embodiments. In some embodiments, the incubation period ranges from about 1 to about 5 minutes, about 5 to about 10 minutes, about 10 to about 15, minutes, about 15 to about 20 minutes, about 20 minutes to about 30 minutes, about 30 minutes to about 40 minutes, about 40 minutes to about 50 minutes, about 50 minutes to about 60 minutes, and overlapping ranges thereof. In some embodiments, the post-administration waiting period is from 1-4, 4-8, 8-12, 12-16, 16-20, 20-24 hours, and overlapping ranges thereof. Longer or shorter incubation periods are used in some embodiments. In some embodiments, cells are administered concurrently with LLLT administration to the target tissue. In some embodiments, cells are administered to a subject, a period of time elapses, and then LLLT is used to treat both the cells and the target tissue. For example, the post-administration waiting period ranges from a one or more minutes to about 48 hours, in some embodiments. In some embodiments, the post-administration waiting period ranges from about 1 to about 5 minutes, about 5 to about 10 minutes, about 10 to about 15, minutes, about 15 to about 20 minutes, about 20 minutes to about 30 minutes, about 30 minutes to about 40 minutes, about 40 minutes to about 50 minutes, about 50 minutes to about 60 minutes, and overlapping ranges thereof. In some embodiments, the post-administration waiting period is from 1-4, 4-8, 8-12, 12-16, 16-20, 20-24 hours, and overlapping ranges thereof. Longer or shorter incubation periods are used in some embodiments. LLLT in conjunction with stem cells can, in several embodiments, enhance the effects of the stem cells and advantageous provides improved therapy for a wide variety of clinical applications.

Low Level Light Therapy

High power density laser radiation is now well accepted as a surgical tool for cutting, cauterizing, and ablating biological tissue. High energy lasers are now routinely used for vaporizing superficial skin lesions and, to make deep cuts. For a laser to be suitable for use as a surgical laser, it must provide laser energy at a power sufficient to heart tissue to temperatures over 50° C. Power outputs for surgical lasers vary from 1-5 W for vaporizing superficial tissue, to about 100 W for deep cutting.

In contrast, LLLT involves therapeutic administration of laser energy to a patient at vastly lower power outputs than those used in high energy laser applications, resulting in desirable biological (e.g., biostimulatory) effects while leaving tissue undamaged. For example, in rat models of myocardial infarction and ischemia-reperfusion injury, low energy laser irradiation reduces infarct size and left ventricular dilation, and enhances angiogenesis in the myocardium. (Yaakobi et al., *J. Appl. Physiol.* 90, 2411-19 (2001)). LLLT has been described for treating pain, including headache and muscle pain, and inflammation. As discussed in herein, LLLT alters one or more characteristics of stem cells (either endogenous or delivered) that yields improved therapeutic effects in cellular therapy.

Certain embodiments described herein and related to LLLT methods for enhancing stem cell function and therapeutic benefit are based in part on the new and surprising discovery that power density (i.e., power per unit area or irradiance; as used herein, these terms are interchangeable) of the light energy applied to tissue appears to be an important factor in determining the relative efficacy of low level light therapy, and particularly with respect to enhancing the function of neurons in both healthy and diseased states.

Several embodiments described herein provide methods directed toward the enhancement of neurologic function in a subject. In several embodiments, the methods include delivering a neurologic enhancing effective amount of a light energy having a wavelength in the visible to near-infrared wavelength range to at least one area of the brain of a subject. In certain embodiments, delivering the neurologic function enhancing effective amount of light energy includes delivering a predetermined power density of light energy through the skull to the target area of the brain and/or delivering light energy through the skull to at least one area of the brain of a subject, wherein the wavelength, power density and amount of the light energy delivered are sufficient to cause an enhancement of neurologic functioning. As discussed herein, in other embodiments, LLLT is delivered to other target tissues to treat disease or injury, and/or to potentiate the efficacy of cell therapy.

LLLT, also referred to as phototherapy or laser therapy, involves therapeutic administration of light energy to a patient at lower power outputs than those used for cutting, cauterizing, or ablating biological tissue, which, in several embodiments, results in desirable biological (e.g., biostimulatory) effects while leaving tissue undamaged. In non-invasive phototherapy, it is desirable, in some embodiments, to apply an efficacious amount of light energy to the internal tissue to be treated using light sources positioned outside the body.

Laser therapy has been shown to be effective in a variety of settings, including treating lymphoedema and muscular trauma, and carpal tunnel syndrome. According to several embodiments, laser-generated infrared radiation penetrates various tissues, including the brain, and modifies function. In some embodiments, laser-generated infrared radiation can induce angiogenesis, modify growth factor (transforming growth factor-β) signaling pathways, and enhance protein synthesis.

In some embodiments, absorption of the light energy by intervening tissue can limit the amount of light energy delivered to the target tissue site, while heating the intervening tissue. In addition, scattering of the light energy by intervening tissue can limit the power density or energy density delivered to the target tissue site. Brute force attempts to circumvent these effects by increasing the power and/or power density applied to the outside surface of the body can result in damage (e.g., burning) of the intervening tissue.

Non-invasive phototherapy methods according to several embodiments are circumscribed by setting selected treatment parameters within specified limits so as to preferably avoid damaging the intervening tissue. A review of the existing scientific literature in this field would cast doubt on whether a set of undamaging, yet efficacious, parameters could be found. However, certain embodiments, as described herein, provide devices and methods which can achieve this goal.

Such embodiments may include selecting a wavelength of light at which the absorption by intervening tissue is below a damaging level. In several embodiments, wavelengths of light are used at which the absorption by intervening tissue is below a level that inhibits (partially or fully) the normal function of cells within the target tissue or the target tissue as whole. Such embodiments may also include setting the power output of the light source at very low, yet efficacious, power densities (e.g., between approximately 100 $\mu W/cm^2$ to approximately 500 $\mu W/cm^2$, approximately 500 $\mu W/cm^2$ to approximately 2.5 $mW/cm^2$, approximately 2.5 $mW/cm^2$ to approximately 5 $mW/cm^2$, approximately 5 $mW/cm^2$ to approximately 1 $W/cm^2$, approximately 1 $W/cm^2$ to approximately 5 $W/cm^2$, approximately 5 $W/cm^2$ to approximately 10 $W/cm^2$, and overlapping ranges thereof)) at the target tissue site, and time periods of application of the light energy at a few seconds to minutes to achieve an efficacious energy density at the target tissue site being treated. Other parameters can also be varied in the use of phototherapy. In some embodiments, these other parameters contribute to the light energy that is actually delivered to the treated tissue and may play key roles in the efficacy of phototherapy in augmenting the effect of stem cell therapy.

In certain embodiments, the irradiated portion of the brain (or other tissue) can comprise the entire brain (or tissue), or portions thereof (e.g., less than 0.1%, 0.5%, 1%, 5%, 10%, 15%, 25%, 50%, or 75% of the target area). In one embodiment, specific cells or cell-types are treated.

As used herein, the term "neurodegeneration" shall be given its ordinary meaning and shall also to the process of cell destruction resulting from primary destructive events such as stroke or trauma, and also secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amyotrophic lateral sclerosis, heat stroke, epilepsy, Alzheimer's disease, Parkinson's disease, Huntington's disease, dopaminergic impairment, dementia resulting from other causes such as AIDS, cerebral ischemia including focal cerebral ischemia, and physical trauma such as crush or compression injury in the CNS, including a crush or compression injury of the brain, spinal cord, nerves or retina, or any other acute injury or insult producing neurodegeneration. Secondary destructive mechanisms include any mechanism that leads to the generation and release of neurotoxic molecules, including apoptosis, depletion of cellular energy stores because of changes in mitochondrial membrane permeability, release or failure in the reuptake of excessive glutamate, reperfusion injury, and activity of cytokines and inflammation. Both primary and secondary mechanisms may contribute to forming a "zone of danger" for neurons, wherein the neurons in the zone have at least temporarily survived the primary destructive event, but are at risk of dying due to processes having delayed effect.

As used herein, the term "neuroprotection" shall be given its ordinary meaning and shall also refer to a therapeutic strategy for slowing or preventing the otherwise irreversible loss of neurons due to neurodegeneration after a primary destructive event, whether the neurodegeneration loss is due to disease mechanisms associated with the primary destructive event or secondary destructive mechanisms.

As used herein, the term "cognitive function" as used herein shall be given its ordinary meaning and shall also refer to cognition and cognitive or mental processes or functions, including those relating to knowing, thinking, learning, perception, memory (including immediate, recent, or remote memory), and judging. Symptoms of loss of cognitive function can also include changes in personality, mood, and behavior of the patient. Diseases or conditions affecting cognitive function include Alzheimer's disease, dementia, AIDS or HIV infection, Cruetzfeldt-Jakob disease, head trauma (including single-event trauma and long-term trauma such as multiple concussions or other traumas which may result from athletic injury), Lewy body disease, Pick's disease, Parkinson's disease, Huntington's disease, drug or alcohol abuse, brain tumors, hydrocephalus, kidney or liver disease, stroke, depression, and other mental diseases which cause disruption in cognitive function, and neurodegeneration.

As used herein, the term "motor function" as used herein shall be given its ordinary meaning and shall also refer to those bodily functions relating to muscular movements, primarily conscious muscular movements, including motor coordination, performance of simple and complex motor acts, and the like.

As used herein, the term "neurologic function" as used herein shall be given its ordinary meaning and shall also refer to both cognitive function and motor function.

As used herein, the terms "cognitive enhancement" and "motor enhancement" as used herein shall be given its ordinary meaning and shall also refer to the improving or heightening of cognitive function and motor function, respectively.

As used herein, the term "neurologic enhancement" as used herein shall be given its ordinary meaning and shall also include both cognitive enhancement and motor enhancement.

As used herein, the term "neuroprotective effective" as used herein shall be given its ordinary meaning and shall also refer to a characteristic of an amount of light energy, wherein the amount is a power density of the light energy measured in $mW/cm^2$. The amount of light energy achieves the goal of preventing, avoiding, reducing or eliminating neurodegeneration, which should result in cognitive enhancement and/or motor enhancement.

As used herein, the term "neurologic function enhancement effective" as used herein shall be given its ordinary meaning and shall also refer to a characteristic of an amount of light energy, wherein the amount is a power density of the light energy measured in $mW/cm^2$ (or another art-recognized unit of measure). The amount of light energy achieves the goal of neuroprotection, motor enhancement and/or cognitive enhancement, and/or enhancement of stem cell viability, proliferation, differentiation, or increased efficacy of cell therapy.

Thus, a method for the treatment or enhancement of neurologic function in a patient in need of such treatment involves delivering a neurologic function enhancement effective amount or a neuroprotective-effective amount of light energy having a wavelength in the visible to near-infrared wavelength range to a target area of the patient's brain 20. In certain embodiments, the target area of the patient's brain 20 includes an area exhibiting neurodegeneration. In other embodiments, the target area includes portions of the brain 20 not exhibiting neurodegeneration. Without being bound by theory or by a specific mechanism, it is believed that irradiation of healthy tissue in proximity to the area exhibiting neurodegeneration increases the production of ATP and copper ions in the healthy tissue and which then migrate to cells exhibiting neurodegeneration, thereby producing beneficial effects. Additional information regarding the biomedical mechanisms or reactions involved in phototherapy is provided by Tiina I. Karu in "Mechanisms of Low-Power Laser Light Action on Cellular Level", Proceedings of SPIE Vol. 4159 (2000), Effects of Low-Power Light on Biological Systems V, Ed. Rachel Lubart, pp. 1-17, which is incorporated in its entirety by reference herein. In a preferred embodiment, delivering the neurologic function enhancement effective amount of light energy includes selecting a surface power density of the light energy sufficient to deliver such predetermined power density of light energy to the target area of the brain or other tissue. Likewise, a method for preventing, reducing the severity of a later heat stroke in a subject, reducing the incidence of future heat stroke, and/or reducing the likelihood of onset heat stroke in a subject includes delivering light energy having a wavelength in the visible to near-infrared wavelength range and a predetermined power density through the skull to at least one area of the brain of a subject, wherein the wavelength, power density and amount of the light energy delivered are sufficient to prevent, reduce the severity, or reduce the incidence of heat stroke in the subject.

In certain embodiments, a method treats a subject suffering from Parkinson's disease. The method includes delivering light energy having a wavelength in the visible to near-infrared wavelength range through the skull to at least one target area of the brain of the subject, wherein the wavelength, power density and amount of the light energy delivered are sufficient to prevent, reduce the severity, or reduce the incidence of Parkinson's disease in the subject.

In certain embodiments, the target area of the brain may be all of the brain or a specific area of the brain including, but not limited to, an area associated with a particular cognitive or motor function, an area exhibiting neurodegeneration, the cortex, and/or an area that has been affected by trauma. The subject may have a cognitive or motor impairment such as from neurodegeneration or the subject may be normal.

In certain embodiments, the predetermined power density is a power density of at least about $0.01$ $mW/cm^2$. The predetermined power density in certain embodiments is typically selected from the range of about $0.01$ $mW/cm^2$ to about $100$ $mW/cm^2$. In certain embodiments, power densities above or below these values may be used. To deliver the predetermined power density at the level of the brain tissue, a required, relatively greater surface power density of the light energy is calculated taking into account attenuation of the light energy as it travels from the skin surface through various tissues including skin, bone and brain tissue. Factors known to affect penetration and to be taken into account in the calculation include skin pigmentation, the presence and color of hair over the area to be treated (if any), and the location of the affected brain region, particularly the depth of the area to be treated relative to the surface. For example, to obtain a desired power density of $50$ $mW/cm^2$ at the cortical surface of the brain may require a surface power density of approximately $3500$ $mW/cm^2$. When targeting depths further below the cortical surface (e.g., ~3 cm below the surface) an increased power density may be required. Likewise, when targeting more superficial tissues, a lower power density is used in certain embodiments. Certain characteristics of the target tissue define the particular power density requirements. As discussed above, the scalp, blood, bone and other intervening tissues absorb some of the administered light. With a higher level of skin pigmentation, a higher surface power density is required to deliver a predetermined power density of light energy to a subsurface brain site. Thus, adjustments are made in power density applied depending on patient characteristics, target tissue depth, and the amount and content of any intervening tissues. The light energy can have a predetermined power density at the subdermal target tissue (e.g., at a depth of approximately 2 centimeters below the dura). It is presently believed that phototherapy of tissue is most effective when irradiating the target tissue with power densities of light of at least about $0.01$ $mW/cm^2$ and up to about $1$ $W/cm^2$. In various embodiments, the subsurface power density is at least about $0.01, 0.05, 0.1, 0.5, 1, 5, 10, 15, 20, 30, 40, 50, 60, 70, 80,$ or $90$ $mW/cm^2$, respectively, depending on the desired clinical performance. In some embodiments, the subsurface power density is selected from a range of about $0.01$ $mW/cm^2$ to about $15$ $mW/cm^2$, or of about $2$ $mW/cm^2$ to about $50$ $mW/cm^2$. In certain embodiments, the subsurface power density is preferably about $0.01$ $mW/cm^2$ to about $100$ $mW/cm^2$, more preferably about $0.01$ $mW/cm^2$ to about $50$ $mW/cm^2$, and most preferably about $2$ $mW/cm^2$ to about $20$ $mW/cm^2$. It is believed that these subsurface power densities are especially effective at producing the desired biostimulative effects on the tissue being treated. However, in other embodiments, higher or lower power densities are used to generate the desired effects on the target tissue.

In certain embodiments, the methods encompass using light energy having a wavelength of about 630 nanometers to about 904 nanometers, and in certain embodiments the light energy has a wavelength of about 780 nanometers to about 840 nanometers. In one embodiment, the light energy is preferably from a coherent source (i.e. a laser, for example a GaAIAs laser diode), but light from non-coherent sources may also be used. In some embodiments, the light is substantially monochromatic (i.e. one wavelength or a very narrow band of wavelengths).

In certain embodiments, the methods encompass placing a light source in contact with a region of skin that is either adjacent an area of the brain or other organ in which treatment is desired, contralateral to such area, or a combination of the foregoing, and then administering the light energy, including the neurologic function enhancing effective amount of light energy, as may be measured by power density, to the target area of the brain. To treat a patient, including those suffering from neurodegeneration or a loss or diminishment of motor skills, cognition or cognitive or mental processes or functions, as well as persons having generally normal cognitive or motor functions (whether to enhance such functions or to pre-treat so as to prevent or lessen heat stroke), or to potentiate and/or otherwise improve the efficacy of cell therapy for other diseases, the light source is placed in contact with a region of skin, for example on the scalp, adjacent a target area of the brain. The target area may be an area of the brain affected by disease or trauma that has been identified such as by using standard medical imaging techniques, it may be a portion of the brain that is known to control certain functions or processes, or it may be any section of the brain, including but not limited to the cortex, cerebellum and other brain regions. In delivering the light, the power density may be a predetermined power density. In certain embodiments, a surface power density of the light energy sufficient for the light energy to penetrate the skull is determined. The determination of the required surface power density, which is relatively higher than the power density to be delivered to the brain (or other) tissue being treated, takes into account factors that attenuate power density as it travels through tissue, including skull thickness of the patient (or other intervening tissues), skin pigmentation, and location of the tissue being treated, particularly the distance of the brain area from the skin surface where the light energy is applied. The power and other parameters are then adjusted according to the results of the calculation.

In certain embodiments, a method increases the production of adenosine triphosphate (ATP) by neurons to increase neurologic function. The method comprises irradiating neurons with light energy having a wavelength in the near infrared to visible portion of the electromagnetic spectrum for at least about 1 second, where the power density of said light energy at the neurons is at least about 0.01 mW/cm$^2$. In other embodiments, ATP is increased in other cell types.

In several embodiments, the treatment proceeds continuously for a period of about 30 seconds to about 2 hours, more preferably for a period of about 1 to 20 minutes. The treatment may be terminated after one treatment period, or the treatment may be repeated with preferably about 1 to 2 days passing between treatments. The length of treatment time and frequency of treatment periods depends on several factors, including the functional recovery of the patient and the results of imaging analysis. In some cases, such as where the disease is degenerative (e.g. Alzheimer's disease) or where treatment is given to a generally healthy patient, the treatment may continue at chosen intervals indefinitely.

The precise power density selected for treating the patient will depend on a number of factors, including the specific wavelength of light selected, the type of disease (if any), the clinical condition of the subject including the extent of brain area affected, and the like. Similarly, it should be understood that the power density of light energy to be delivered to the target area or affected brain area may be adjusted to be combined with any other therapeutic agent or agents, especially pharmaceutical agents to achieve the desired biological effect. The selected power density will again depend on a number of factors, including the specific light energy wavelength chosen, the individual additional therapeutic agent or agents chosen, and the clinical condition of the subject.

During the treatment, the light energy may be continuously provided, or it may be pulsed. If the light is pulsed, the pulses are preferably at least about 10 ns long and occur at a frequency of up to about 100 Hz. In some embodiments, light is pulsed at a frequency of up to about 100 kHz. In some embodiments, pulsed light is administered at a frequency ranging from about 100 Hz to 500 Hz, 100 Hz to 1 kHz, 1 kHz to 10 kHz, 10 kHz to 20 kHz, 20 kHz to 30 kHz, 30 kHz to 40 kHz, 40 kHz to 50 kHz, 50 kHz to 60 kHz, 60 kHz to 70 kHz, 70 kHz to 80 kHz, 80 kHz to 90 kHz, 90 kHz to 100 kHz, and overlapping ranges thereof. Continuous wave light is also be used, in some embodiments.

It has been discovered that treatment of stroke using low level light therapy is more effective if treatment begins several hours after the stroke has occurred. This is a surprising result, in that the thrombolytic therapies currently in use for treatment of stroke must begin within a few hours of the stroke. Because oftentimes many hours pass before a person who has suffered a stroke receives medical treatment, the short time limit for initiating thrombolytic therapy excludes many patients from treatment. Consequently, the present methods may be used to treat a greater percentage of stroke patients. Accordingly, it is believed that treatment to enhance cognitive and/or motor function may also take place after a primary event occurs in that it appears that the neural cells need only be living to receive benefit from the methods described herein.

Apparatuses for LLLT

As discussed above, phototherapy involves therapeutic administration of light energy to a patient at lower power outputs than those used for cutting, cauterizing, or ablating biological tissue, resulting in desirable biostimulatory effects while leaving tissue undamaged. In other embodiments, the electromagnetic radiation comprises infrared light. In some embodiments a device may be used to administer at least a portion of the electromagnetic radiation to subdermal tissues. In certain such embodiments, the device comprises parameters for light administration to a patient. Examples of devices for infrared light administration to a patient compatible with certain embodiments described herein are disclosed in U.S. Pat. No. 7,303,578, U.S. Patent Application Publication Nos. 2005/0107851 A1, 2007/0179570 A1, and U.S. patent application Ser. No. 12/389,294, all of which are incorporated in their entireties by reference herein.

Element to Inhibit Temperature Increases at an Irradiated Surface

Figure 2:
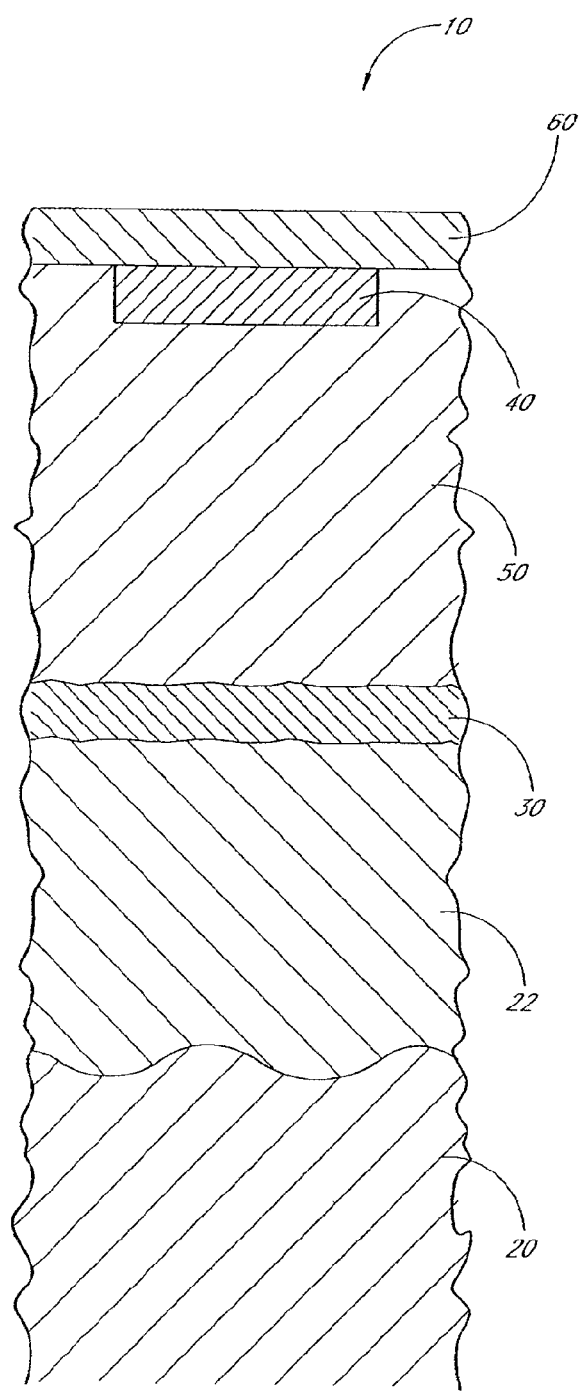
FIG. 2 schematically illustrates a fragmentary cross-sectional view taken along the lines 2-2 of FIG. 1, showing one embodiment of a portion of a therapy apparatus comprising an element and its relationship to the scalp and brain.

FIGS. 1 and 2 schematically illustrate an embodiment of a therapy apparatus 10 for treating a patient's brain 20. It shall be appreciated that other target tissues are treated in several embodiments disclosed herein. The therapy apparatus 10 comprises a light source 40 having an output emission area 41 positioned to irradiate a portion of the brain 20 with an efficacious power density and wavelength of light. The therapy apparatus 10 further comprises an element 50 interposed between the light source 40 and the patient's scalp 30. The element 50 is adapted to inhibit temperature increases at the scalp 30 caused by the light.

As used herein, the term "element" is used in its broadest sense, including, but not limited to, as a reference to a constituent or distinct part of a composite device. In certain embodiments, the element 50 is adapted to contact at least a portion of the patient's scalp 30 (see e.g., FIG. 1). In certain such embodiments, the element 50 is in thermal communication with and covers at least a portion of the scalp 30. In other embodiments, the element 50 is spaced away from the scalp 30 and does not contact the scalp 30.

In certain embodiments, the light passes through the element 50 prior to reaching the scalp 30 such that the element 50 is in the optical path of light propagating from the light source 40, through the scalp 30, through the bones, tissues, and fluids of the head, to the brain. In certain embodiments, the light passes through a transmissive medium of the element 50, while in other embodiments, the light passes through an aperture of the element 50. As described more fully below, the element 50 may be utilized with various embodiments of the therapy apparatus 10. Similar light penetration pathways occur in other embodiments that are targeting other tissues (e.g., light passes through skin and chest wall to target cardiac tissue).

In certain embodiments, the light source 40 is disposed on the interior surface of a cap 60 which fits securely over the patient's head. The cap 60 provides structural integrity for the therapy apparatus 10 and holds the light source 40 and element 50 in place. Example materials for the cap 60 include, but are not limited to, metal, plastic, or other materials with appropriate structural integrity. The cap 60 may include an inner lining 62 comprising a stretchable fabric or mesh material, such as Lycra or nylon. In certain embodiments, the light source 40 is adapted to be removably attached to the cap 60 in a plurality of positions so that the output emission area 41 of the light source 40 can be advantageously placed in a selected position for treatment of Parkinson's disease in any portion of the brain 20. In other embodiments, the light source 40 can be an integral portion of the cap 60.

The light source 40 illustrated by FIGS. 1 and 2 comprises at least one power conduit 64 coupled to a power source (not shown). In some embodiments, the power conduit 64 comprises an electrical conduit which is adapted to transmit electrical signals and power to an emitter (e.g., laser diode or light-emitting diode). In certain embodiments, the power conduit 64 comprises an optical conduit (e.g., optical waveguide) which transmits optical signals and power to the output emission area 41 of the light source 40. In certain such embodiments, the light source 40 comprises optical elements (e.g., lenses, diffusers, and/or waveguides) which transmit at least a portion of the optical power received via the optical conduit 64. In still other embodiments, the therapy apparatus 10 contains a power source (e.g., a battery) and the power conduit 64 is substantially internal to the therapy apparatus 10.

In certain embodiments, the patient's scalp 30 comprises hair and skin which cover the patient's skull. In other embodiments, at least a portion of the hair is removed prior to the phototherapy treatment, so that the therapy apparatus 10 substantially contacts the skin of the scalp 30.

In certain embodiments, the element 50 is adapted to contact the patient's scalp 30, thereby providing an interface between the therapy apparatus 10 and the patient's scalp 30. In certain such embodiments, the element 50 is coupled to the light source 40 and in other such embodiments, the element is also adapted to conform to the scalp 30, as schematically illustrated in FIG. 1. In this way, the element 50 positions the output emission area 41 of the light source 40 relative to the scalp 30. In certain such embodiments, the element 50 is mechanically adjustable so as to adjust the position of the light source 40 relative to the scalp 30. By fitting to the scalp 30 and holding the light source 40 in place, the element 50 inhibits temperature increases at the scalp 30 that would otherwise result from misplacement of the light source 40 relative to the scalp 30. In addition, in certain embodiments, the element 50 is mechanically adjustable so as to fit the therapy apparatus 10 to the patient's scalp 30.

In certain embodiments, the element 50 provides a reusable interface between the therapy apparatus 10 and the patient's scalp 30. In such embodiments, the element 50 can be cleaned or sterilized between uses of the therapy apparatus, particularly between uses by different patients. In other embodiments, the element 50 provides a disposable and replaceable interface between the therapy apparatus 10 and the patient's scalp 30. By using pre-sterilized and pre-packaged replaceable interfaces, certain embodiments can advantageously provide sterilized interfaces without undergoing cleaning or sterilization processing immediately before use.

In certain embodiments, the element 50 comprises a container (e.g., a cavity or bag) containing a material (e.g., gel or liquid). The container can be flexible and adapted to conform to the contours of the scalp 30. Other example materials contained in the container of the element 50 include, but are not limited to, thermal exchange materials such as glycerol and water. The element 50 of certain embodiments substantially covers the entire scalp 30 of the patient, as schematically illustrated in FIG. 2. In other embodiments, the element 50 only covers a localized portion of the scalp 30 in proximity to the irradiated portion of the scalp 30.

In certain embodiments, at least a portion of the element 50 is within an optical path of the light from the light source 40 to the scalp 30. In such embodiments, the element 50 is substantially optically transmissive at a wavelength of the light emitted by the output emission area 41 of the light source 40 and is adapted to reduce back reflections of the light. By reducing back reflections, the element 50 increases the amount of light transmitted to the brain 20 and reduces the need to use a higher power light source 40 which may otherwise create temperature increases at the scalp 30. In certain such embodiments, the element 50 comprises one or more optical coatings, films, layers, membranes, etc. in the optical path of the transmitted light which are adapted to reduce back reflections.

In certain such embodiments, the element 50 reduces back reflections by fitting to the scalp 30 so as to substantially reduce air gaps between the scalp 30 and the element 50 in the optical path of the light. The refractive-index mismatches between such an air gap and the element 50 and/or the scalp 30 would otherwise result in at least a portion of the light propagating from the light source 40 to the brain 20 to be reflected back towards the light source 40.

In addition, certain embodiments of the element 50 comprise a material having, at a wavelength of light emitted by the light source 40, a refractive index which substantially matches the refractive index of the scalp 30 (e.g., about 1.3), thereby reducing any index-mismatch-generated back reflections between the element 50 and the scalp 30. Examples of materials with refractive indices compatible with embodiments described herein include, but are not limited to, glycerol, water, and silica gels. Example index-matching gels include, but are not limited to, those available from Nye Lubricants, Inc. of Fairhaven, Mass.

In certain embodiments, the element 50 is adapted to cool the scalp 30 by removing heat from the scalp 30 so as to inhibit temperature increases at the scalp 30. In certain such embodiments, the element 50 comprises a reservoir (e.g., a chamber or a conduit) adapted to contain a coolant. The coolant flows through the reservoir near the scalp 30. The scalp 30 heats the coolant, which flows away from the scalp 30, thereby removing heat from the scalp 30 by active cooling. The coolant in certain embodiments circulates between the element 50 and a heat transfer device, such as a chiller, whereby the coolant is heated by the scalp 30 and is cooled by the heat transfer device. Example materials for the coolant include, but are not limited to, water or air.

Figure 3:
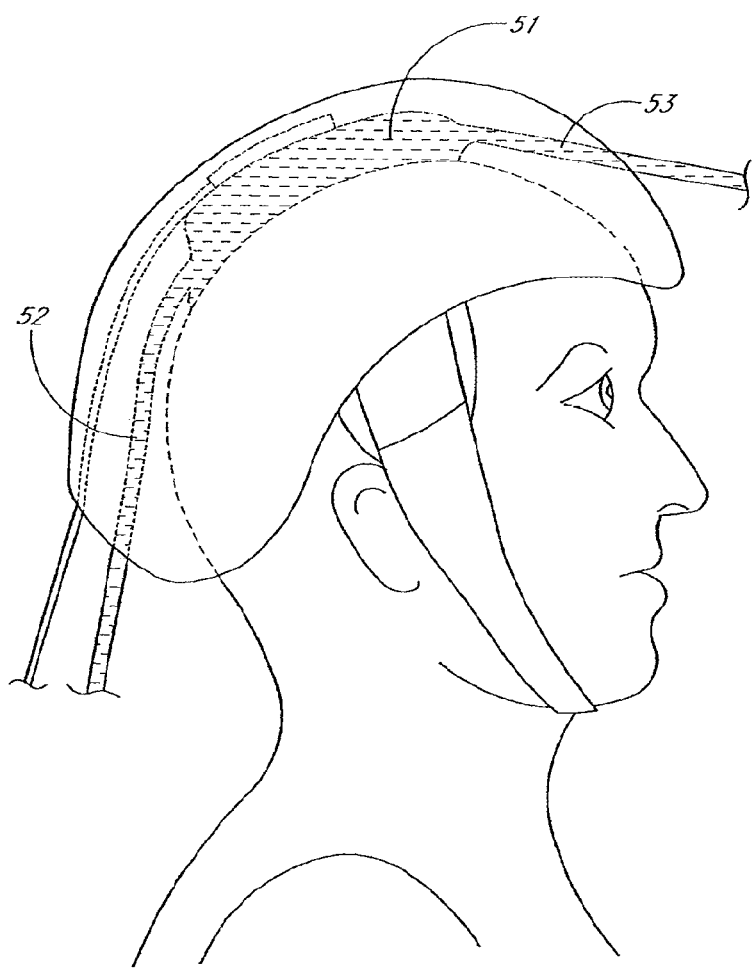
FIG. 3 schematically illustrates an embodiment with an element comprising a container coupled to an inlet conduit and an outlet conduit for the transport of a flowing material through the element.

In certain embodiments, the element 50 comprises a container 51 (e.g., a flexible bag) coupled to an inlet conduit 52 and an outlet conduit 53, as schematically illustrated in FIG. 3. A flowing material (e.g., water, air, or glycerol) can flow into the container 51 from the inlet conduit 52, absorb heat from the scalp 30, and flow out of the container 51 through the outlet conduit 53. Certain such embodiments can provide a mechanical fit of the container 51 to the scalp 30 and sufficient thermal coupling to prevent excessive heating of the scalp 30 by the light. In certain embodiments, the container 51 can be disposable and replacement containers 51 can be used for subsequent patients.

In still other embodiments, the element 50 comprises a container (e.g., a flexible bag) containing a material which does not flow out of the container but is thermally coupled to the scalp 30 so as to remove heat from the scalp 30 by passive cooling. Example materials include, but are not limited to, water, glycerol, and gel. In certain such embodiments, the non-flowing material can be pre-cooled (e.g., by placement in a refrigerator) prior to the phototherapy treatment to facilitate cooling of the scalp 30.

In certain embodiments, the element 50 is adapted to apply pressure to at least a portion of the scalp 30. By applying sufficient pressure, the element 50 can blanch the portion of the scalp 30 by forcing at least some blood out the optical path of the light energy. The blood removal resulting from the pressure applied by the element 50 to the scalp 30 decreases the corresponding absorption of the light energy by blood in the scalp 30. As a result, temperature increases due to absorption of the light energy by blood at the scalp 30 are reduced. As a further result, the fraction of the light energy transmitted to the subdermal target tissue of the brain 20 is increased. In certain embodiments, a pressure greater than two pounds per square inch is used to blanch the irradiated portion of the scalp 30, while in certain other embodiments, a pressure of at least one pound per square inch is used to blanch the irradiated portion of the scalp 30. Other ranges of pressures for blanching the irradiated portion of the scalp 30 are also compatible with certain embodiments described herein. The maximum pressure used to blanch the irradiated portion of the scalp 30 is limited in certain embodiments by patient comfort levels and tissue damage levels.

Figure 4A:
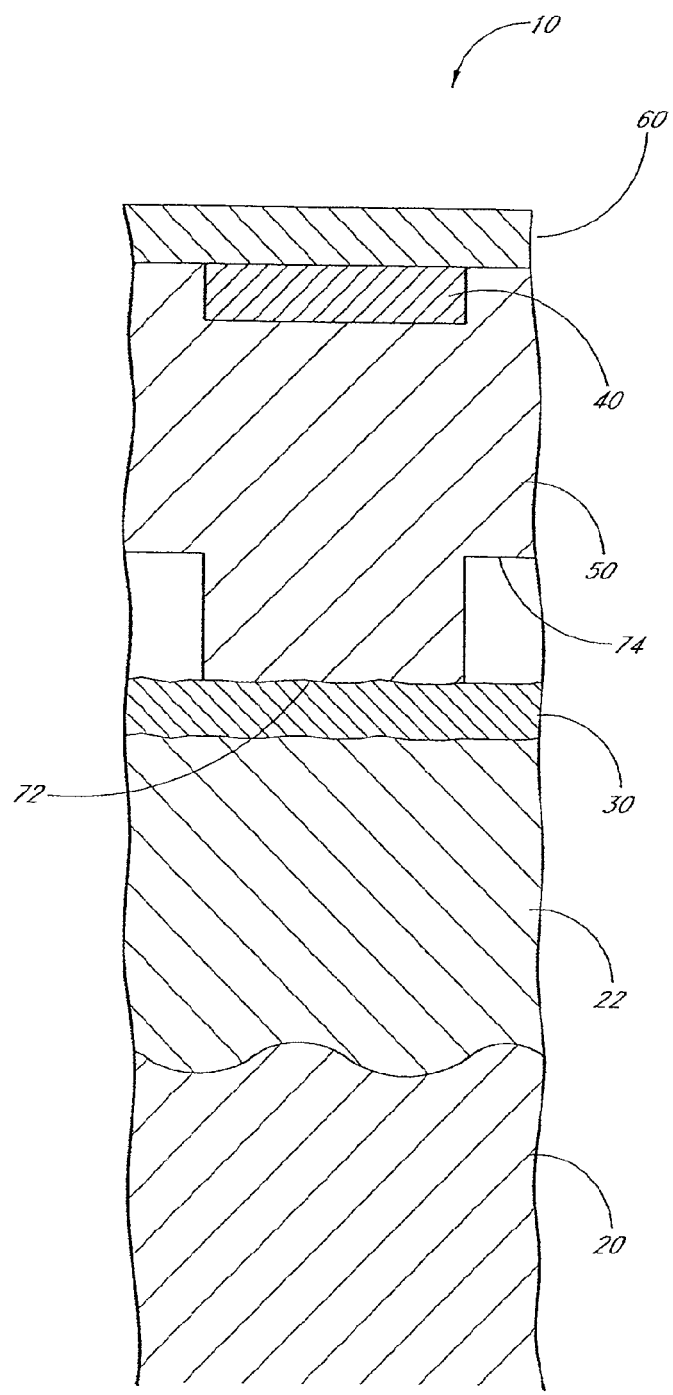
FIG. 4A schematically illustrates a fragmentary cross-sectional view taken along the lines 2-2 of FIG. 1, showing another embodiment of a portion of a therapy apparatus comprising an element with a portion contacting the scalp and a portion spaced away from the scalp.
Figure 4B:
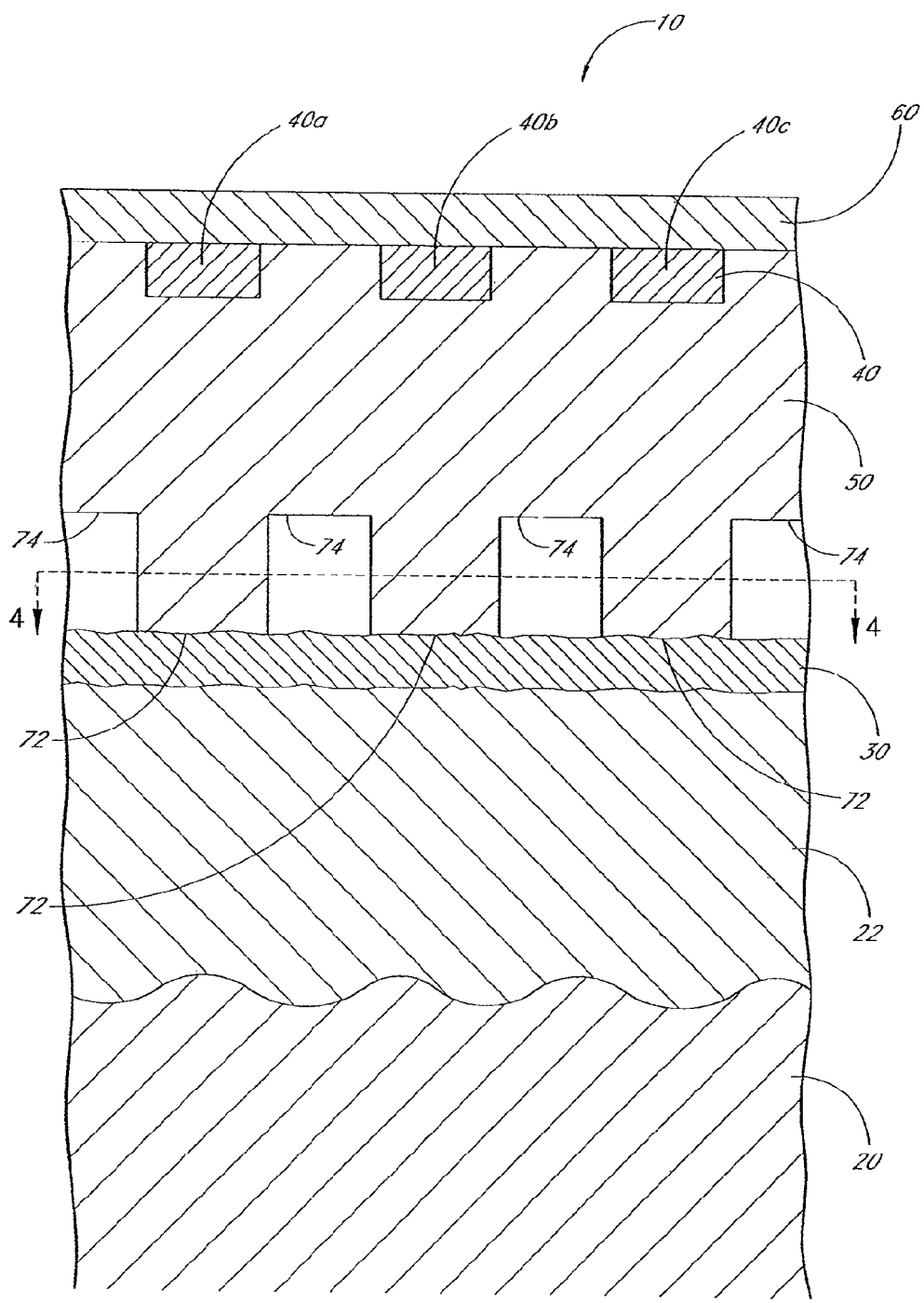
FIG. 4B schematically illustrates a fragmentary cross-sectional view taken along the lines 2-2 of FIG. 1, showing an embodiment of a portion of a therapy apparatus comprising a plurality of light sources and an element with portions contacting the scalp and portions spaced away from the scalp.

FIGS. 4A and 4B schematically illustrate embodiments of the element 50 adapted to facilitate the blanching of the scalp 30. In the cross-sectional view of a portion of the therapy apparatus 10 schematically illustrated in FIG. 4A, certain element portions 72 contact the patient's scalp 30 and other element portions 74 are spaced away from the scalp 30. The element portions 72 contacting the scalp 30 provide an optical path for light to propagate from the light source 40 to the scalp 30. The element portions 72 contacting the scalp 30 also apply pressure to the scalp 30, thereby forcing blood out from beneath the element portion 72. FIG. 4B schematically illustrates a similar view of an embodiment in which the light source 40 comprises a plurality of light sources 40a, 40b, 40c.

Figure 5A:
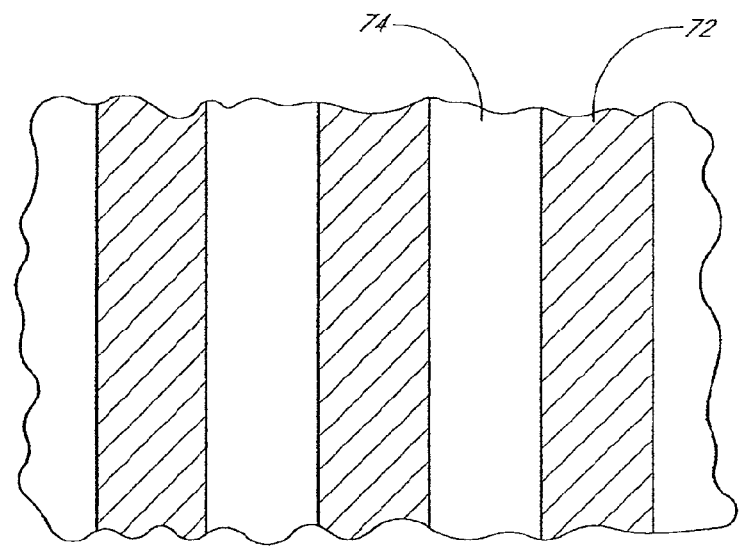
FIGS. 5A and 5B schematically illustrate cross-sectional views of two embodiments of the element in accordance with FIG. 4B taken along the line 4-4.
Figure 5B:
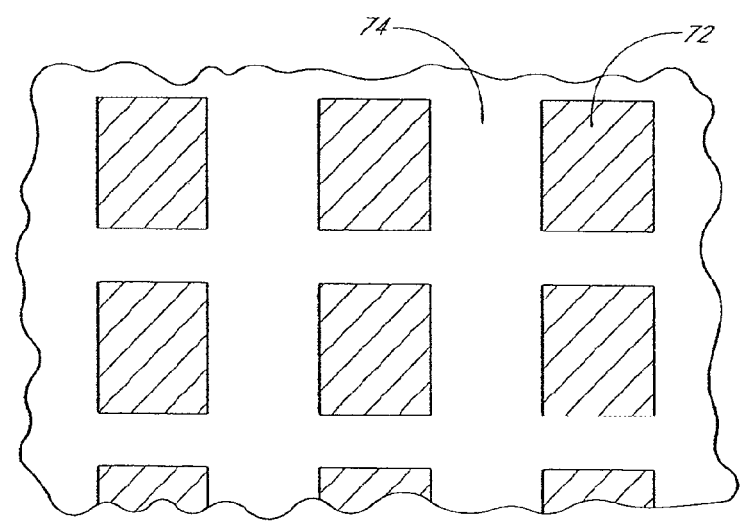

FIG. 5A schematically illustrates one embodiment of the cross-section along the line 4-4 of FIG. 4B. The element portions 72 contacting the scalp 30 comprise ridges extending along one direction, and the element portions 74 spaced away from the scalp 30 comprise troughs extending along the same direction. In certain embodiments, the ridges are substantially parallel to one another and the troughs are substantially parallel to one another. FIG. 5B schematically illustrates another embodiment of the cross-section along the line 4-4 of FIG. 4B. The element portions 72 contacting the scalp 30 comprise a plurality of projections in the form of a grid or array. More specifically, the portions 72 are rectangular and are separated by element portions 74 spaced away from the scalp 30, which form troughs extending in two substantially perpendicular directions. The portions 72 of the element 50 contacting the scalp 30 can be a substantial fraction of the total area of the element 50 or of the scalp 30.

Figure 6A:
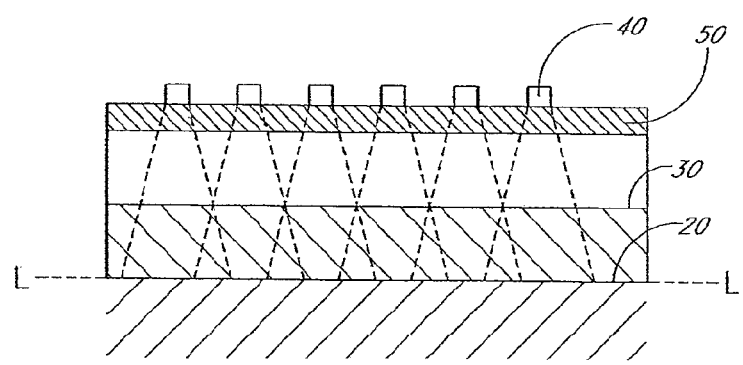
FIGS. 6A-6C schematically illustrate an embodiment in which the light sources are spaced away from the scalp.
Figure 6B:
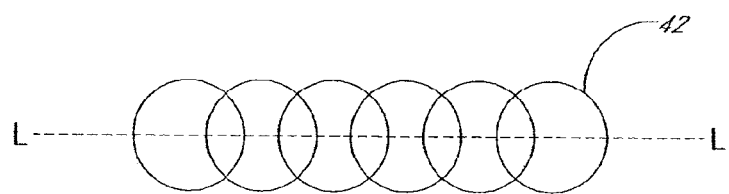
Figure 6C:
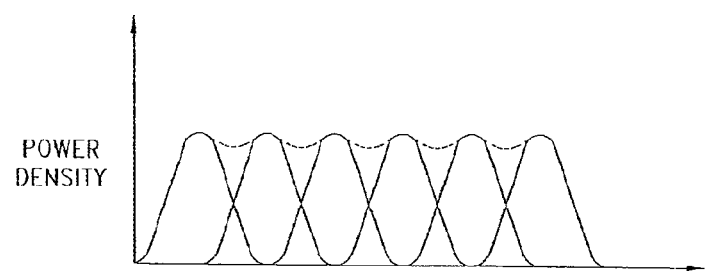

FIGS. 6A-6C schematically illustrate an embodiment in which the light sources 40 are spaced away from the scalp 30. In certain such embodiments, the light emitted by the light sources 40 propagates from the light sources 40 through the scalp 30 to the brain 20 and disperses in a direction generally parallel to the scalp 30, as shown in FIG. 6A. The light sources 40 are preferably spaced sufficiently far apart from one another such that the light emitted from each light source 40 overlaps with the light emitted from the neighboring light sources 40 at the brain 20. FIG. 6B schematically illustrates this overlap as the overlap of circular spots 42 at a reference depth at or below the surface of the brain 20. FIG. 6C schematically illustrates this overlap as a graph of the power density at the reference depth of the brain 20 along the line L-L of FIGS. 6A and 6B. Summing the power densities from the neighboring light sources 40 (shown as a dashed line in FIG. 6C) serves to provide a more uniform light distribution at the tissue to be treated. In such embodiments, the summed power density is preferably less than a damage threshold of the brain 20 and above an efficacy threshold.

Figure 7A:
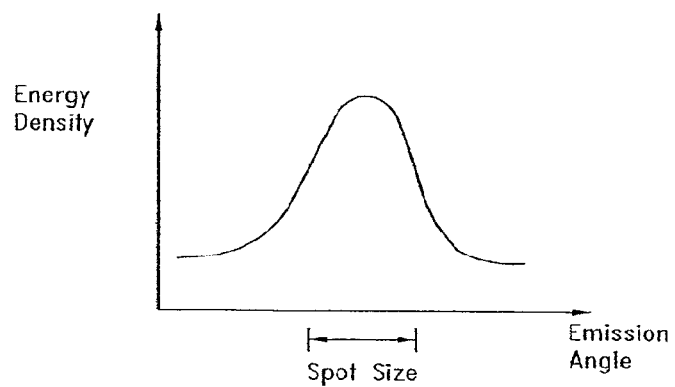
FIGS. 7A and 7B schematically illustrate the diffusive effect on the light by the element.
Figure 7B:
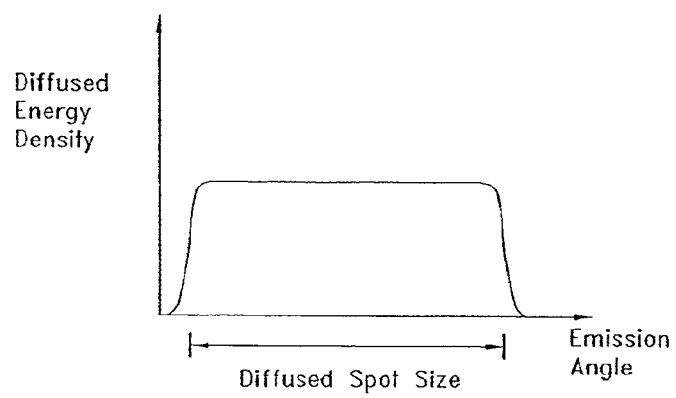

In certain embodiments, the element 50 is adapted to diffuse the light prior to reaching the scalp 30. FIGS. 7A and 7B schematically illustrate the diffusive effect on the light by the element 50. An example energy density profile of the light emitted by a light source 40, as illustrated by FIG. 7A, is peaked at a particular emission angle. After being diffused by the element 50, as illustrated by FIG. 7B, the energy density profile of the light does not have a substantial peak at any particular emission angle, but is substantially evenly distributed among a range of emission angles. By diffusing the light emitted by the light source 40, the element 50 distributes the light energy substantially evenly over the area to be illuminated, thereby inhibiting "hot spots" which would otherwise create temperature increases at the scalp 30. In addition, by diffusing the light prior to its reaching the scalp 30, the element 50 can effectively increase the spot size of the light impinging the scalp 30, thereby advantageously lowering the power density at the scalp 30, as described more fully below. In addition, in embodiments with multiple light sources 40, the element 50 can diffuse the light to alter the total light output distribution to reduce inhomogeneities.

In certain embodiments, the element 50 provides sufficient diffusion of the light such that the power density of the light is less than a maximum tolerable level of the scalp 30 and brain 20. In certain other embodiments, the element 50 provides sufficient diffusion of the light such that the power density of the light equals a therapeutic value at the target tissue. The element 50 can comprise example diffusers including, but are not limited to, holographic diffusers such as those available from Physical Optics Corp. of Torrance, Calif. and Display Optics P/N SN1333 from Reflexite Corp. of Avon, Conn.

Figure 8A:
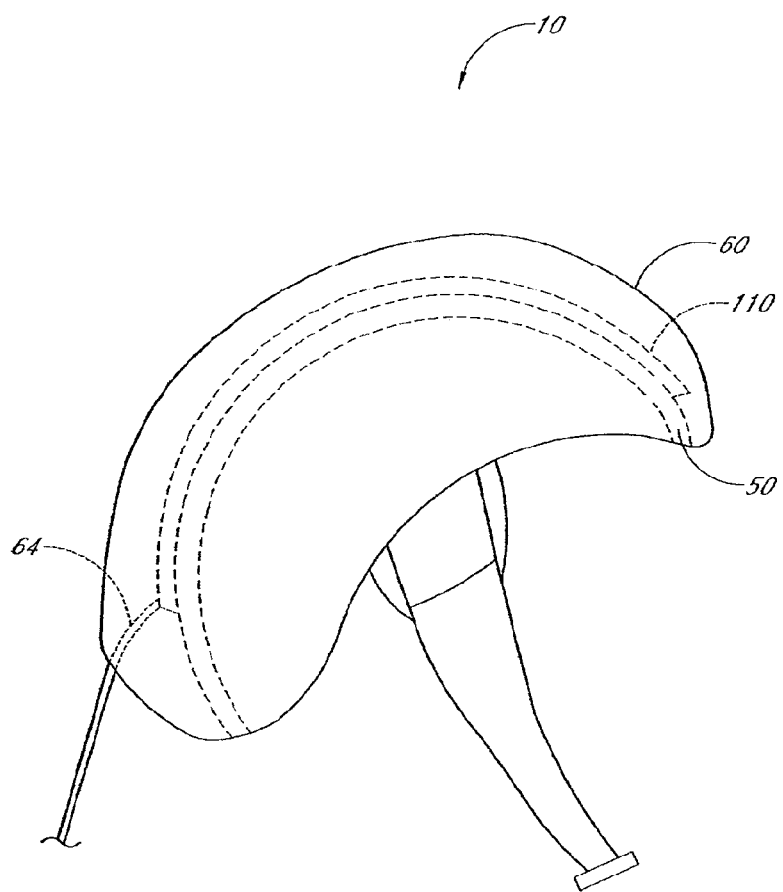
FIG. 8A schematically illustrates a therapy apparatus comprising a cap and a light source comprising a light blanket.
Figure 8B:
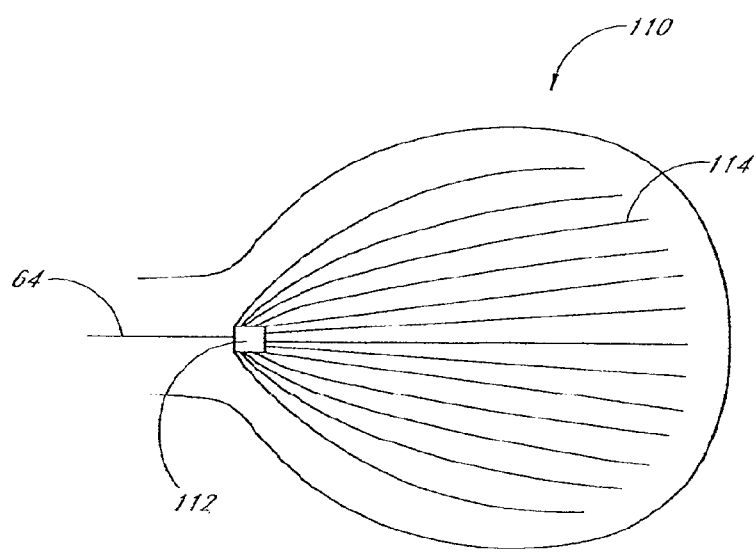
FIGS. 8B and 8C schematically illustrate two embodiments of the light blanket.
Figure 8C:
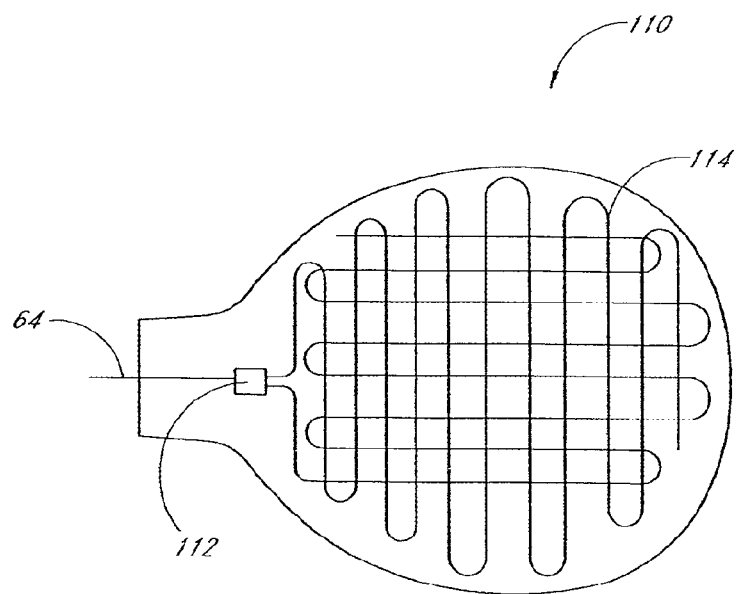

FIG. 8A schematically illustrates another embodiment of the therapy apparatus 10 which comprises the cap 60 and a light source comprising a light-emitting blanket 110. FIG. 8B schematically illustrates an embodiment of the blanket 110 comprising a flexible substrate 111 (e.g., flexible circuit board), a power conduit interface 112, and a sheet formed by optical fibers 114 positioned in a fan-like configuration. FIG. 8C schematically illustrates an embodiment of the blanket 110 comprising a flexible substrate 111, a power conduit interface 112, and a sheet formed by optical fibers 114 woven into a mesh. The blanket 110 is preferably positioned within the cap 60 so as to cover an area of the scalp 30 corresponding to a portion of the brain 20 to be treated.

In certain such embodiments, the power conduit interface 112 is adapted to be coupled to an optical fiber conduit 64 which provides optical power to the blanket 110. The optical power interface 112 of certain embodiments comprises a beam splitter or other optical device which distributes the incoming optical power among the various optical fibers 114. In other embodiments, the power conduit interface 112 is adapted to be coupled to an electrical conduit which provides electrical power to the blanket 110. In certain such embodiments, the power conduit interface 112 comprises one or more laser diodes, the output of which is distributed among the various optical fibers 114 of the blanket 110. In certain other embodiments, the blanket 110 comprises an electroluminescent sheet which responds to electrical signals from the power conduit interface 112 by emitting light. In such embodiments, the power conduit interface 112 comprises circuitry adapted to distribute the electrical signals to appropriate portions of the electroluminescent sheet.

The side of the blanket 110 nearer the scalp 30 is preferably provided with a light scattering surface, such as a roughened surface to increase the amount of light scattered out of the blanket 110 towards the scalp 30. The side of the blanket 110 further from the scalp 30 is preferably covered by a reflective coating so that light emitted away from the scalp 30 is reflected back towards the scalp 30. This configuration is similar to configurations used for the "back illumination" of liquid-crystal displays (LCDs). Other configurations of the blanket 110 are compatible with embodiments described herein.

In certain embodiments, the light source 40 generates light which cause eye damage if viewed by an individual. In such embodiments, the apparatus 50 can be configured to provide eye protection so as to avoid viewing of the light by individuals. For example, opaque materials can be appropriately placed to block the light from being viewed directly. In addition, interlocks can be provided so that the light source 40 is not activated unless the apparatus 50 is in place, or other appropriate safety measures are taken.

The phototherapy methods for the treatments described herein may be practiced and described using, for example, a low level laser therapy apparatus such as that shown and described in U.S. Pat. Nos. 6,214,035, 6,267,780, 6,273,905 and 6,290,714, which are all incorporated in their entirety by reference herein, as are the references incorporated by reference therein.

Figure 9:
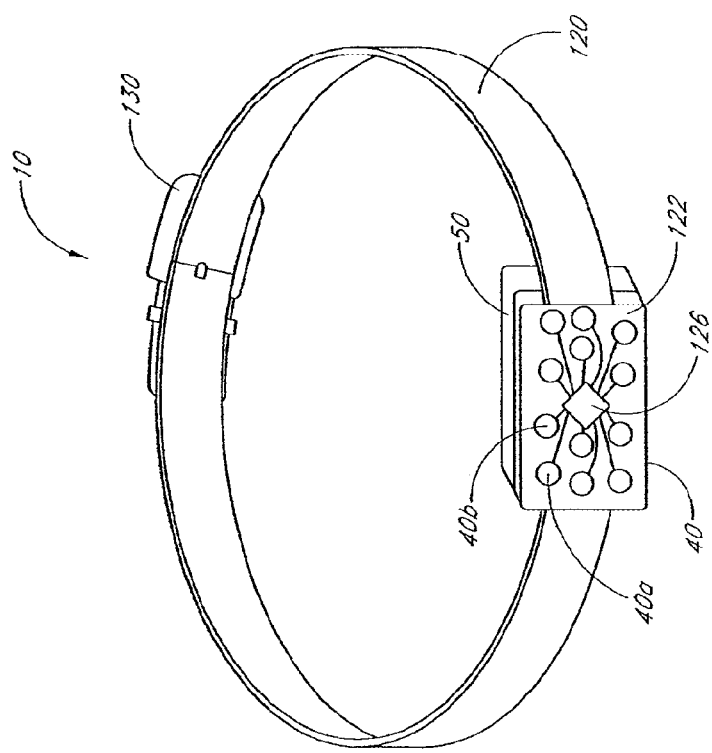
FIG. 9 schematically illustrates a therapy apparatus comprising a flexible strap and a housing.

Another suitable phototherapy apparatus in accordance with embodiments described here is illustrated in FIG. 9. The illustrated therapy apparatus 10 includes a light source 40, an element 50, and a flexible strap 120 adapted for securing the therapy apparatus 10 over an area of the patient's head, or other treatment site or external surface of the patient above or near a treatment site. The light source 40 can be disposed on the strap 120 itself, or in a housing 122 coupled to the strap 120. The light source 40 preferably comprises a plurality of diodes 40a, 40b, etc. capable of emitting light energy having a wavelength in the visible to near-infrared wavelength range. The element 50 is adapted to be positioned between the light source 40 and the patient's scalp 30.

It shall be appreciated that while several embodiments are described and illustrated as being directed to therapy of the brain (via the scalp) of a patient, the parameters, concepts, materials, methods and devices disclosed are also capable, in other embodiments, for the efficacious application of LLLT to other tissues. As such, similar variables (e.g., heat at skin surface overlying the heart, depth of light penetration) are accounted for in such embodiments.

The therapy apparatus 10 further includes a power supply (not shown) operatively coupled to the light source 40, and a programmable controller 126 operatively coupled to the light source 40 and to the power supply. The programmable controller 126 is configured to control the light source 40 so as to deliver a predetermined power density to the brain tissue 20. In certain embodiments, as schematically illustrated in FIG. 9, the light source 40 comprises the programmable controller 126. In other embodiments the programmable controller 126 is a separate component of the therapy apparatus 10.

The strap is preferably fabricated from an elastomeric material to which is secured any suitable securing means, such as mating Velcro strips, snaps, hooks, buttons, ties, or the like. Alternatively, the strap is a loop of elastomeric material sized appropriately to fit snugly over a particular body part, such as a particular arm or leg joint, or around the chest or head. The precise configuration of the strap is subject only to the limitation that the strap is capable of maintaining the light energy sources in a select position relative to the particular area of the body or tissue being treated. In any case, the light sources are secured to the strap so that when the strap is positioned around a body part of the patient, the light sources are positioned so that light energy emitted by the light sources is directed toward the skin surface over which the device is secured. Various strap configurations and spatial distributions of the light energy sources are contemplated so that the device can be adapted to treat different tissues in different areas of the body.

In some embodiments, a strap is not used and instead the light source or sources are incorporated into or attachable onto a light cap which fits securely over the head thereby holding the light source or sources in proximity to the patient's head for treatment. The light cap is preferably constructed of a stretchable fabric or mesh comprising materials such as Lycra or nylon. The light source or sources are preferably removably attached to the cap so that they may be placed in the position needed for treatment of any portion of the brain.

In the example embodiment illustrated in FIG. 9, the housing 122 comprises a layer of flexible plastic or fabric that is secured to the strap 120. In other embodiments, the housing 122 comprises a plate or an enlarged portion of the strap 120. Various strap configurations and spatial distributions of the light sources 40 are compatible with embodiments described herein so that the therapy apparatus 10 can treat selected portions of brain tissue.

Figure 10:
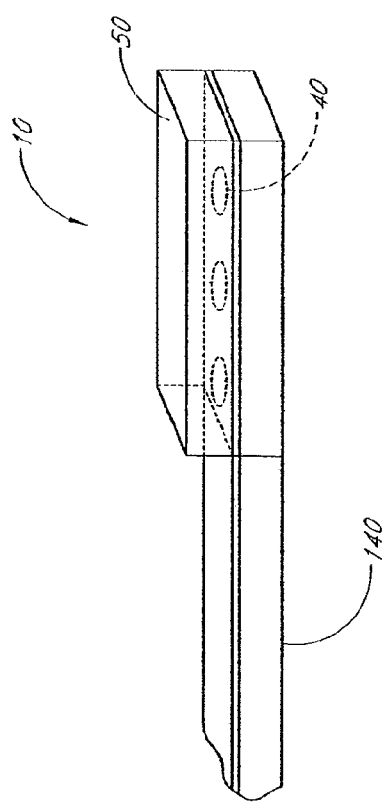
FIG. 10 schematically illustrates a therapy apparatus comprising a handheld probe.

In still other embodiments, the therapy apparatus 10 for delivering the light energy includes a handheld probe 140, as schematically illustrated in FIG. 10. The probe 140 includes a light source 40 and an element 50 as described herein.

Figure 11:
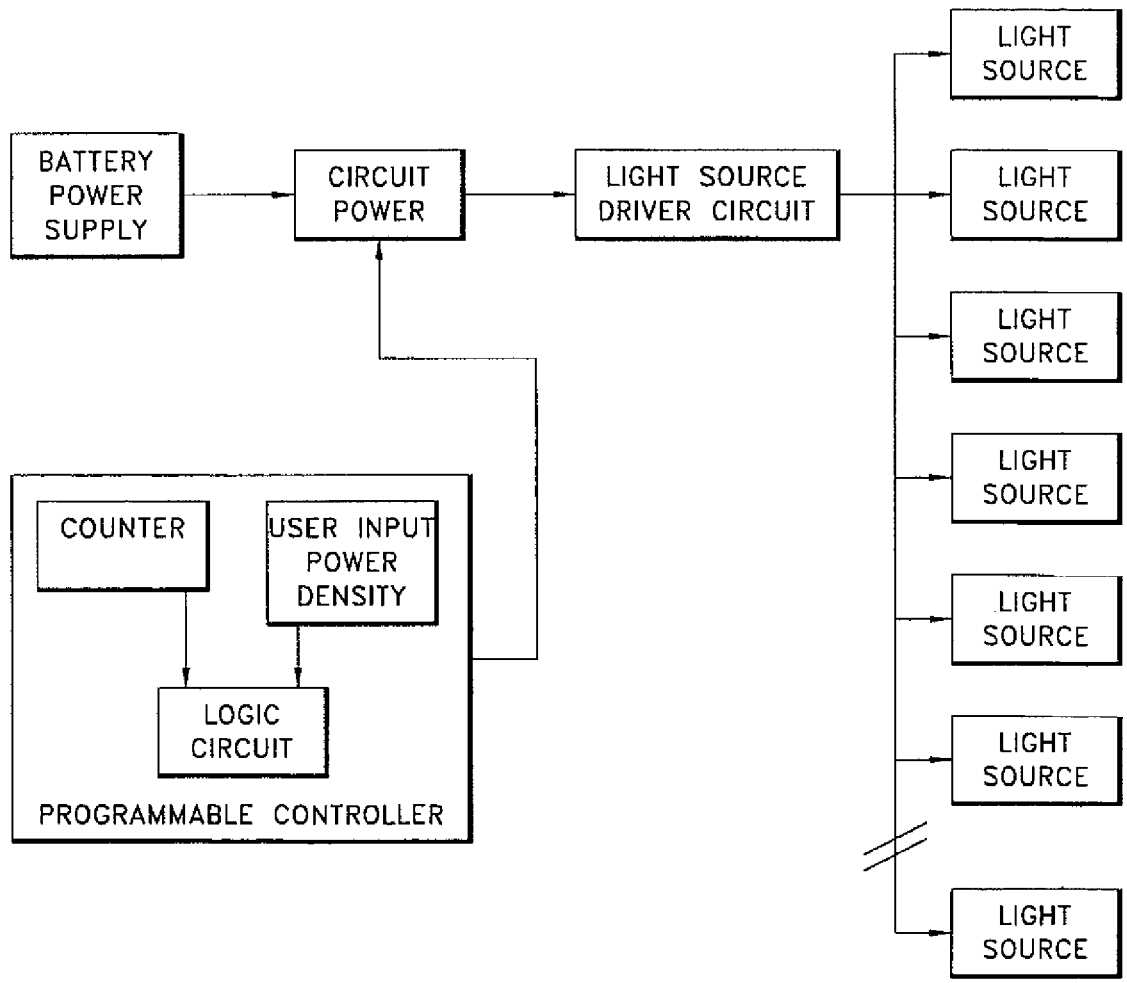
FIG. 11 is a block diagram of a control circuit comprising a programmable controller.

FIG. 11 is a block diagram of a control circuit comprising a programmable controller according to embodiments described herein. The control circuit is configured to adjust the power of the light energy emitted by the light source to generate a predetermined surface power density at the scalp corresponding to a predetermined energy delivery profile, such as a predetermined subsurface power density, to the target tissue.

In certain embodiments, the programmable controller comprises a logic circuit, a clock or counter coupled to the logic circuit, and an user input/interface coupled to the logic circuit. The clock of certain embodiments provides a timing signal to the logic circuit so that the logic circuit can monitor and control timing intervals of the applied light. Examples of timing intervals include, but are not limited to, total treatment times, pulsewidth times for pulses of applied light, and time intervals between pulses of applied light. In certain embodiments, the light sources can be selectively turned on and off to reduce the thermal load on the target tissue and to deliver a selected power density to particular areas of the brain.

The user input/interface of certain embodiments provides signals to the logic circuit which the logic circuit uses to control the applied light. The interface can comprise a user interface or an interface to a sensor monitoring at least one parameter of the treatment. In certain such embodiments, the programmable controller is responsive to signals from the sensor to preferably adjust the treatment parameters to optimize the measured response. The programmable controller can thus provide closed-loop monitoring and adjustment of various treatment parameters to optimize the phototherapy. The signals provided by the interface from a user are indicative of parameters that may include, but are not limited to, patient characteristics (e.g., skin type, fat percentage), selected applied power densities, target time intervals, and power density/timing profiles for the applied light.

In certain embodiments, the logic circuit is coupled to a light source driver. The light source driver is coupled to a power supply, which in certain embodiments comprises a battery and in other embodiments comprises an alternating current source. The light source driver is also coupled to the light source. The logic circuit is responsive to the signal from the clock and to user input from the user interface to transmit a control signal to the light source driver. In response to the control signal from the logic circuit, the light source driver adjust and controls the power applied to the light sources. Other control circuits besides the control circuit of FIG. 11 are compatible with embodiments described herein.

In certain embodiments, the logic circuit is responsive to signals from a sensor monitoring at least one parameter of the treatment to control the applied light. For example, certain embodiments comprise a temperature sensor thermally coupled to the scalp to provide information regarding the temperature of the scalp to the logic circuit. In such embodiments, the logic circuit is responsive to the information from the temperature sensor to transmit a control signal to the light source driver so as to adjust the parameters of the applied light to maintain the scalp temperature below a predetermined level. Other embodiments include example biomedical sensors including, but not limited to, a blood flow sensor, a blood gas (e.g., oxygenation) sensor, an ATP production sensor, or a cellular activity sensor. Such biomedical sensors can provide real-time feedback information to the logic circuit. In certain such embodiments, the logic circuit is responsive to signals from the sensors to preferably adjust the parameters of the applied light to optimize the measured response. The logic circuit can thus provide closed-loop monitoring and adjustment of various parameters of the applied light to optimize the phototherapy.

Figure 12:
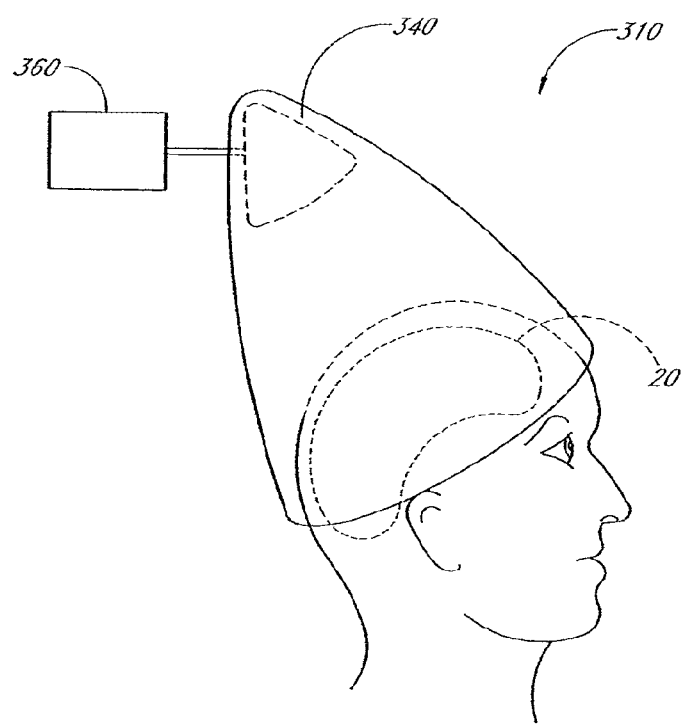
FIG. 12 schematically illustrates a therapy apparatus comprising a light source and a controller.

In certain embodiments, as schematically illustrated in FIG. 12, the therapy apparatus comprises a light source adapted to irradiate a portion of the patient's brain (or other target tissue) with an efficacious power density and wavelength of light. The therapy apparatus further comprises a controller for energizing said light source, so as to selectively produce a plurality of different irradiation patterns on the patient's scalp (or other target tissue). Each of the irradiation patterns is comprised of a least one illuminated area that is small compared to the target tissue, and at least one non-illuminated area.

Figure 13:
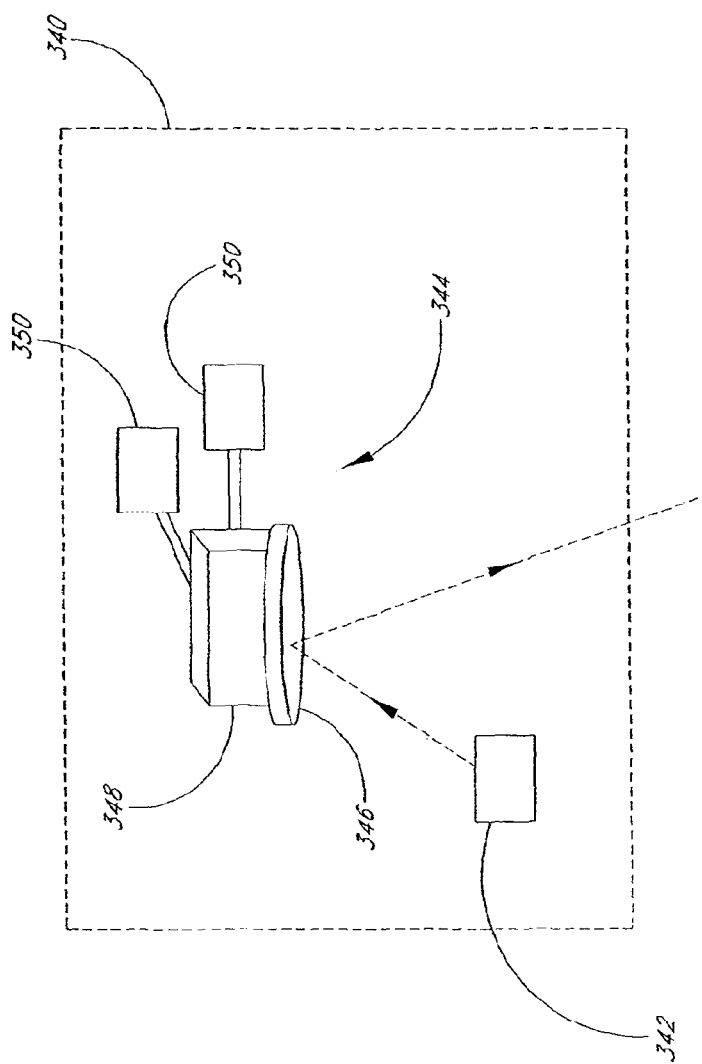
FIG. 13 schematically illustrates a light source comprising a laser diode and a galvometer with a mirror and a plurality of motors.

In certain embodiments, the light source 340 includes an apparatus for adjusting the emitted light to irradiate different portions of the scalp 30. In certain such embodiments, the apparatus physically moves the light source 40 relative to the scalp 30. In other embodiments, the apparatus does not move the light source 40, but redirects the emitted light to different portions of the scalp 30. In an example embodiment, as schematically illustrated in FIG. 13, the light source 340 comprises a laser diode 342 and a galvometer 344, both of which are electrically coupled to the controller 360. The galvometer 344 comprises a mirror 346 mounted onto an assembly 348 which is adjustable by a plurality of motors 350. Light emitted by the laser diode 342 is directed toward the mirror 346 and is reflected to selected portions of the patient's scalp 30 by selectively moving the mirror 346 and selectively activating the laser diode 342. In certain embodiments, the therapy apparatus 310 comprises an element 50 adapted to inhibit temperature increases at the irradiated surface of the patient, as described herein.

Figure 14A:
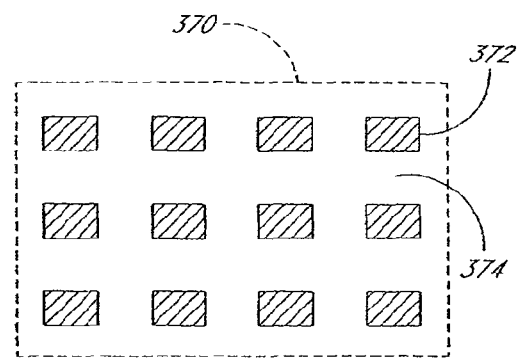
FIGS. 14A and 14B schematically illustrate two irradiation patterns that are spatially shifted relative to each other.

FIG. 14A schematically illustrates an irradiation pattern 370 in accordance with embodiments described herein. The irradiation pattern 370 comprises at least one illuminated area 372 and at least one non-illuminated area 374. In certain embodiments, the irradiation pattern 370 is generated by scanning the mirror 346 so that the light impinges the patient's scalp 30 in the illuminated area 372 but not in the non-illuminated area 374. Certain embodiments modify the illuminated area 372 and the non-illuminated area 374 as a function of time.

Figure 14B:
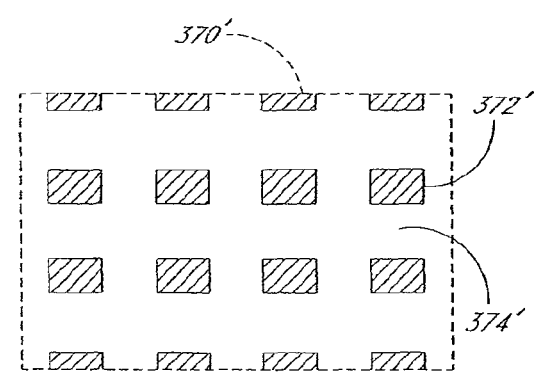

In some embodiments, this selective irradiation can be used to reduce the thermal load on particular locations of the scalp 30 by moving the light from one illuminated area 372 to another. For example, by irradiating the scalp 30 with the irradiation pattern 370 schematically illustrated in FIG. 14A, the illuminated areas 372 of the scalp 30 are heated by interaction with the light, and the non-illuminated areas 374 are not heated. By subsequently irradiating the scalp 30 with the complementary irradiation pattern 370' schematically illustrated in FIG. 14B, the previously non-illuminated areas 374 are now illuminated areas 372', and the previously illuminated areas 372 are now non-illuminated areas 374'. A comparison of the illuminated areas 372 of the irradiation pattern 370 of FIG. 14A with the illuminated area 372' of the irradiation pattern 370' of FIG. 14B shows that the illuminated areas 372, 372' do not significantly overlap one another. In this way, the thermal load at the scalp 30 due to the absorption of the light can be distributed across the scalp 30, thereby avoiding unduly heating one or more portions of the scalp 30.

Figure 15:
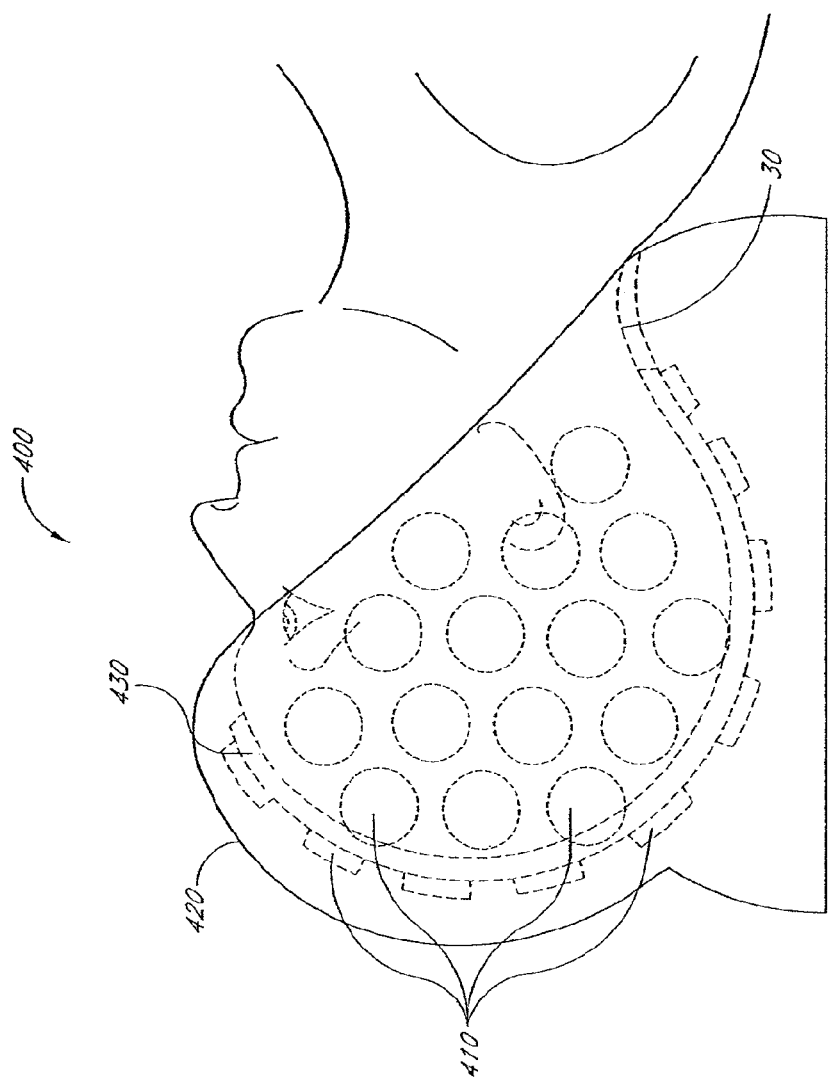
FIG. 15 schematically illustrates an example therapy apparatus in accordance with embodiments described herein.

FIG. 15 schematically illustrates another therapy apparatus 400 in accordance with embodiments described herein. The therapy apparatus 400 comprises a plurality of light sources 410 in a housing 420. Each light source 410 has an output emission area positioned to irradiate a corresponding portion of the brain 20 with an efficacious power density and wavelength of light. In certain embodiments, these portions overlap such that the portion of the brain 20 irradiated by two or more light sources 410 overlap one another at least in part. As described herein, the light sources 410 can be activated by a controller (not shown) in concert or separately to produce a predetermined irradiation pattern.

The therapy apparatus 400 of FIG. 15 further comprises a cap 430 interposed between the light sources 410 and the patient's scalp 30, such that light passes through the cap 430 prior to reaching the scalp 30. In certain embodiments, the cap 430 is substantially optically transmissive at the wavelength and reduces back reflections of the light. The cap 430 of certain embodiments fits to the scalp 30 so as to substantially reduce air gaps between the scalp 30 and the cap 430. In certain embodiments, the cap 430 comprises a material having a refractive index which substantially matches a refractive index of the scalp 30. In certain embodiments, the cap 430 comprises a material having a refractive index which substantially matches a refractive index of the skin and/or hair of the scalp 30.

In the embodiment schematically illustrated by FIG. 15, the cap 430 is wearable over the patient's scalp 30. In certain such embodiments, the patient wears the cap 430 and is in a reclining position so as to place his head in proximity to the light sources 410. The cap 430 is adapted to inhibit temperature increases at the scalp 30 caused by the light from the light sources 410, as described herein (e.g., by cooling the scalp 30, by blanching a portion of the scalp 30, by diffusing the light prior to reaching the scalp 30).

Figure 16:
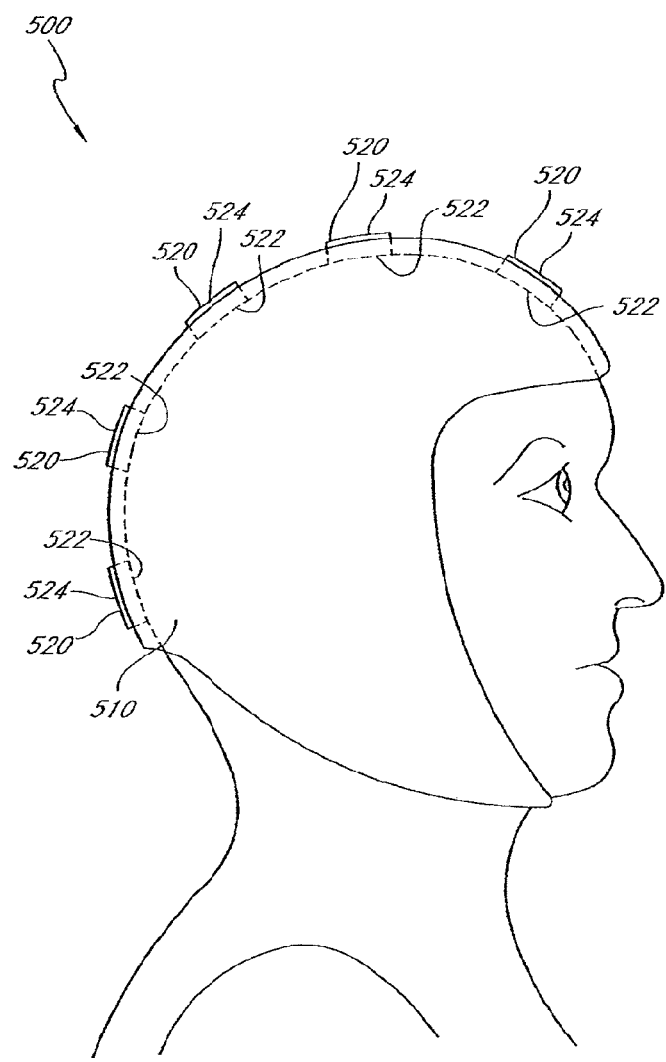
FIG. 16 schematically illustrates an example apparatus which is wearable by a patient for treating the patient's brain.

FIG. 16 schematically illustrates an example apparatus 500 which is wearable by a patient for treating the patient's brain. The apparatus 500 comprises a body 510 and a plurality of elements 520. The body 510 covers at least a portion of the patient's scalp when the apparatus 500 is worn by the patient. Each element 520 has a first portion 522 which conforms to a corresponding portion of the patient's scalp when the apparatus 500 is worn by the patient. Each element 520 has a second portion 524 which conforms to a light source (not shown in FIG. 16) removably contacting the element. Each element 520 is substantially transmissive (e.g., substantially transparent or substantially translucent) to light from the light source to irradiate at least a portion of the patient's brain. In certain embodiments, the light from the light source after being transmitted through each element 520 has a power density which penetrates the patient's cranium to deliver an efficacious amount of light to at least a portion of the patient's brain.

Figure 17:
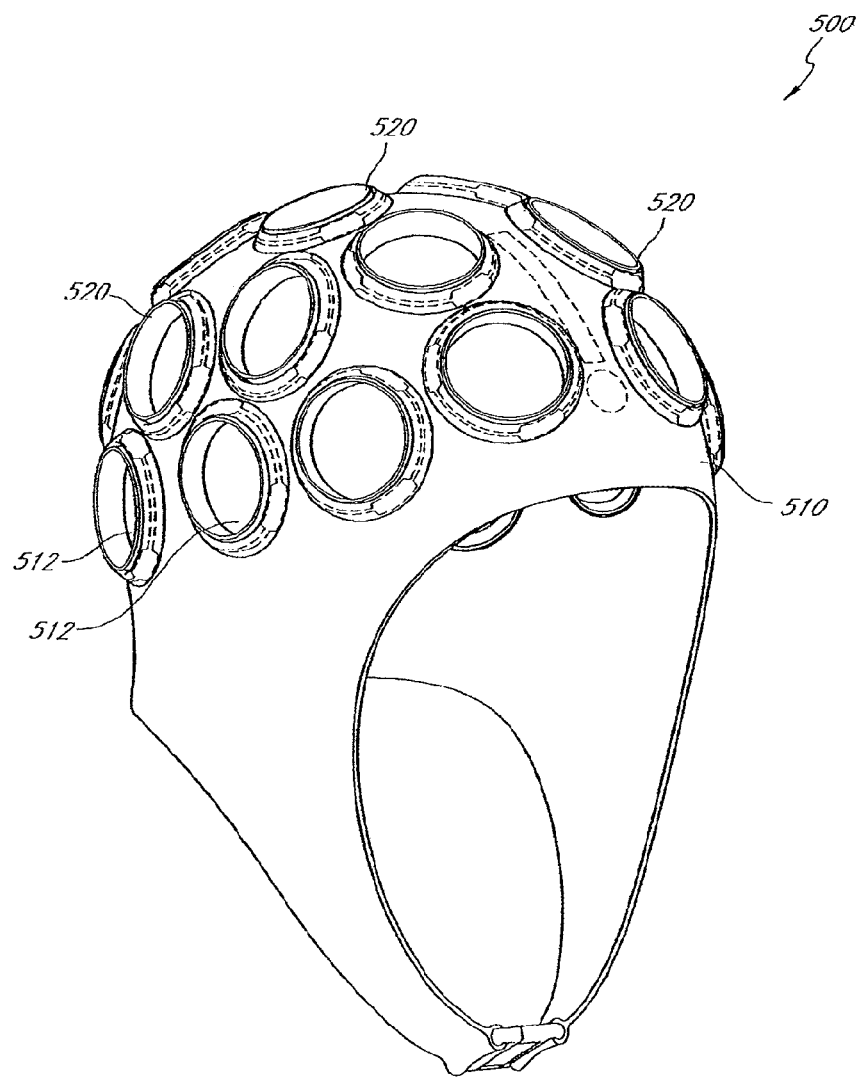
FIG. 17 schematically illustrates an example apparatus having a plurality of elements in accordance with certain embodiments described herein.

FIG. 17 schematically illustrates an example apparatus 500 having a plurality of elements 520 in accordance with certain embodiments described herein. The body 510 shown in FIG. 17 has a plurality of apertures 512 or openings which serve as indicators of treatment site locations. Each element 520 is positioned at a corresponding one of the plurality of apertures 512 and serves as an optical window. In certain embodiments, the plurality of elements 520 comprises at least about 10 elements 520, while in certain other embodiments, the plurality of elements 520 comprises 20 elements 520. In certain other embodiments, the plurality of elements 520 comprises between 15 and 25 elements 520. In certain embodiments in which the light emitting apparatus 600 is configured to directly contact the scalp, the apertures 512 of the body 510 do not contain any elements 520, but instead are indicators of treatment site locations through which the light emitting apparatus 600 is positioned for treatment.

In certain embodiments, the body 510 comprises a hood, as schematically illustrated by FIG. 17, while in other embodiments, the body 510 comprises a cap or has another configuration which is wearable on the patient's head and serves as a support for orienting the elements 520 on the patient's head. In certain embodiments, the body 510 comprises a stretchable material which generally conforms to the patient's scalp. In certain embodiments, the body 510 comprises nylon-backed polychloroprene. In certain embodiments, the body 510 is available in different sizes (e.g., small, medium, large) to accommodate different sizes of heads. In certain embodiments, the apparatus 500 is disposable after a single use to advantageously avoid spreading infection or disease between subsequent patients.

Figure 18:
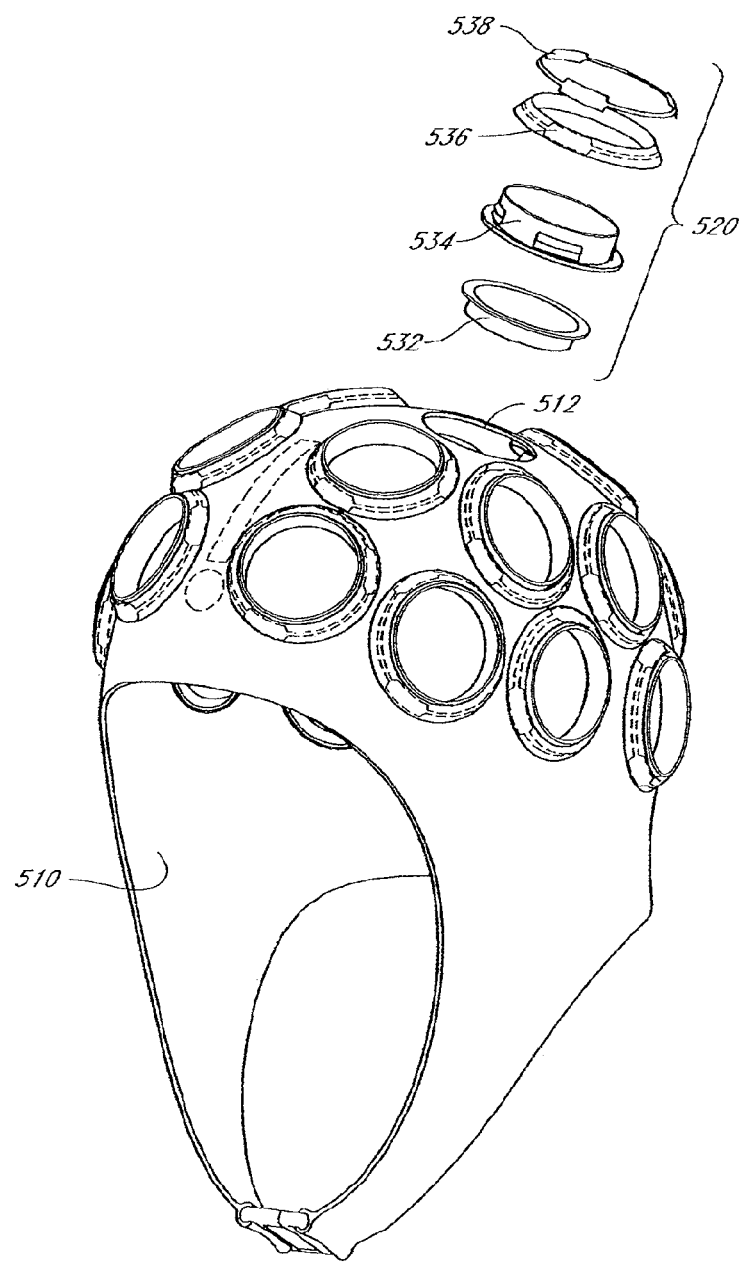
FIG. 18 schematically illustrates an example element in an exploded view.

FIG. 18 schematically illustrates an example element 520 in an exploded view. The example element 520 comprises an optical component 532, a first support ring 534, a second support ring 536, and a label 538. Other configurations of the element 520 are also compatible with certain embodiments described herein.

Figure 19A:
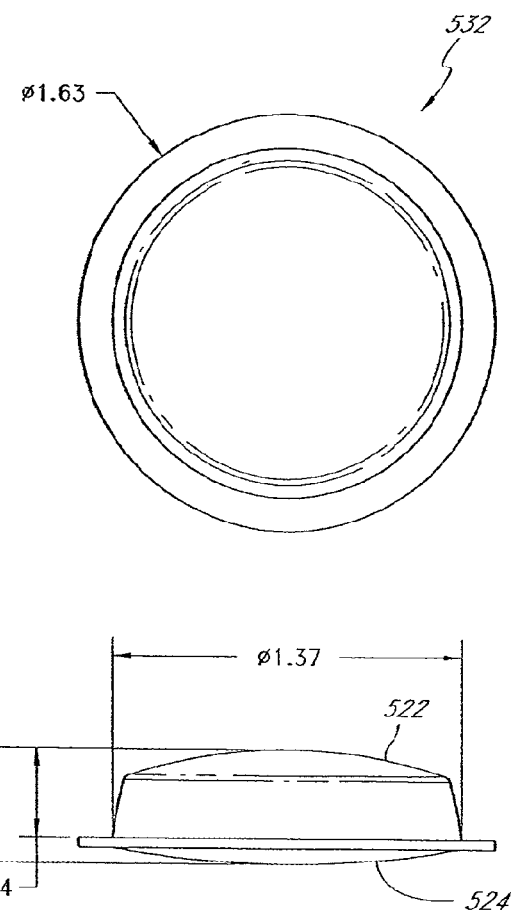
FIG. 19A schematically illustrates an example optical component with example dimensions in inches.

In certain embodiments, the optical component 532 comprises a substantially transmissive (e.g., substantially transparent or substantially translucent) bag comprising a flexible material (which can be biocompatible). FIG. 19A schematically illustrates an example optical component 532 with example dimensions in inches. The bag of FIG. 19A comprises an inflatable container which contains a substantially transmissive liquid (e.g., water) or gel. In certain embodiments, the bag has an outer diameter within a range between about 0.5 inch and about 3 inches. For example, the bag of FIG. 19A has an outer diameter of about 1.37 inches. In certain embodiments, the bag has a volume in a range between about 2 cubic centimeters and about 50 cubic centimeters.

Both the bag and the liquid contained within the bag are substantially transmissive to light having wavelengths to be applied to the patient's brain (e.g., wavelength of approximately 810 nanometers). In certain embodiments, the liquid has a refractive index which substantially matches a refractive index of the patient's scalp, thereby advantageously providing an optical match between the element 520 and the patient's scalp. While the example optical component 532 of FIG. 19A comprises a single bag, in certain other embodiments, the optical component 532 comprises a plurality of bags filled with a substantially transparent liquid.

Figure 19B:
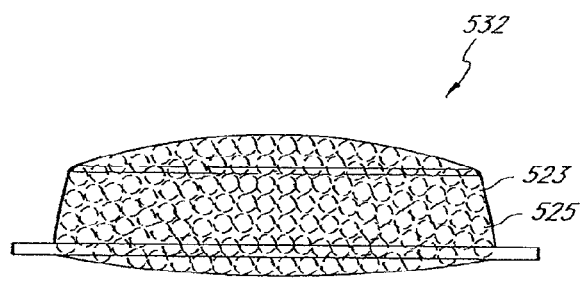
FIGS. 19B and 19C schematically illustrate other example optical components in accordance with certain embodiments described herein.
Figure 19C:
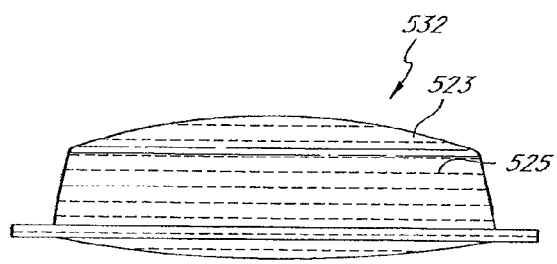

FIGS. 19B and 19C schematically illustrate other example optical components 532 in which the bag contains a composite material. For example, in FIGS. 19B and 19C, the bag contains a first material 523 and a second material 525. In certain embodiments, the first material 523 comprises a soft, substantially transmissive, thermally insulative material (e.g., gel). Example gels compatible with certain embodiments described herein include, but are not limited to, OC-431A-LVP, OCK-451, and OC-462 optical gels available from Nye Corporation of Fairhaven, Mass. In certain embodiments, the second material 525 comprises a rigid, substantially transmissive, thermally conductive material (e.g., silica).

In certain embodiments, as schematically illustrated in FIG. 19B, the second material 525 comprises a plurality of balls distributed within the first material 523. The balls of certain embodiments have diameters less than about 2 millimeters. In certain other embodiments, as schematically illustrated in FIG. 22C, the first material 523 comprises a first plurality of layers and the second material 525 comprises a second plurality of layers. The first plurality of layers is stacked with the second plurality of layers, thereby forming a stack having alternating layers of the first material 523 and the second material 525. In certain embodiments, each layer of the first plurality of layers has a thickness less than about 2 millimeters and each layer of the second plurality of layers has a thickness less than about 2 millimeters. In certain other embodiments, each layer of the first plurality of layers and each layer of the second plurality of layers has a thickness less than about 0.5 millimeter. Other configurations of the first material 523 and the second material 525 within the optical component 532 are also compatible with certain embodiments described herein.

The optical component 532 of certain embodiments advantageously deforms in response to pressure applied to the first portion 522 and the second portion 524. For example, without a load being applied, the optical component 532 of FIG. 19A has a thickness of approximately 0.41 inch, but with approximately four pounds of applied pressure, the optical component 532 of FIG. 19A has a thickness of approximately 0.315 inch. The first portion 522 of the optical component 532 advantageously deforms to substantially conform to a portion of the patient's skull to which the optical component 532 is pressed. For example, in certain embodiments, the first portion 522 comprises a conformable surface of the optical component 532. Thus, in certain such embodiments, the optical component 532 advantageously provides an interface with the patient's scalp which is substantially free of air gaps. The second portion 524 of the optical component 532 advantageously deforms to substantially conform to a light source being pressed thereon. For example, in certain embodiments, the second portion 524 comprises a conformable surface of the optical component 532. Thus, in certain such embodiments, the optical component 532 advantageously provides an interface with the light source which is substantially free of air gaps.

In certain embodiments, the optical component 532 advantageously serves as a heat sink to inhibit temperature increases at the patient's scalp caused by light which is transmitted through the optical component 532. In certain such embodiments, the optical component 532 has a sufficiently high heat capacity to provide an effective heat sink to the patient's scalp. For example, for a bag filled with water (which has a heat capacity of approximately 4180 joules/kilogram-K), a generally disk-shaped bag having a diameter of approximately 32 millimeters and a thickness of approximately 10 millimeters has a sufficient volume, and a sufficient heat capacity, to provide an effective heat sink. Thus, in certain embodiments, each element 520 advantageously inhibits temperature increases at the patient's scalp caused by the light transmitted through the element 520.

Figure 20:
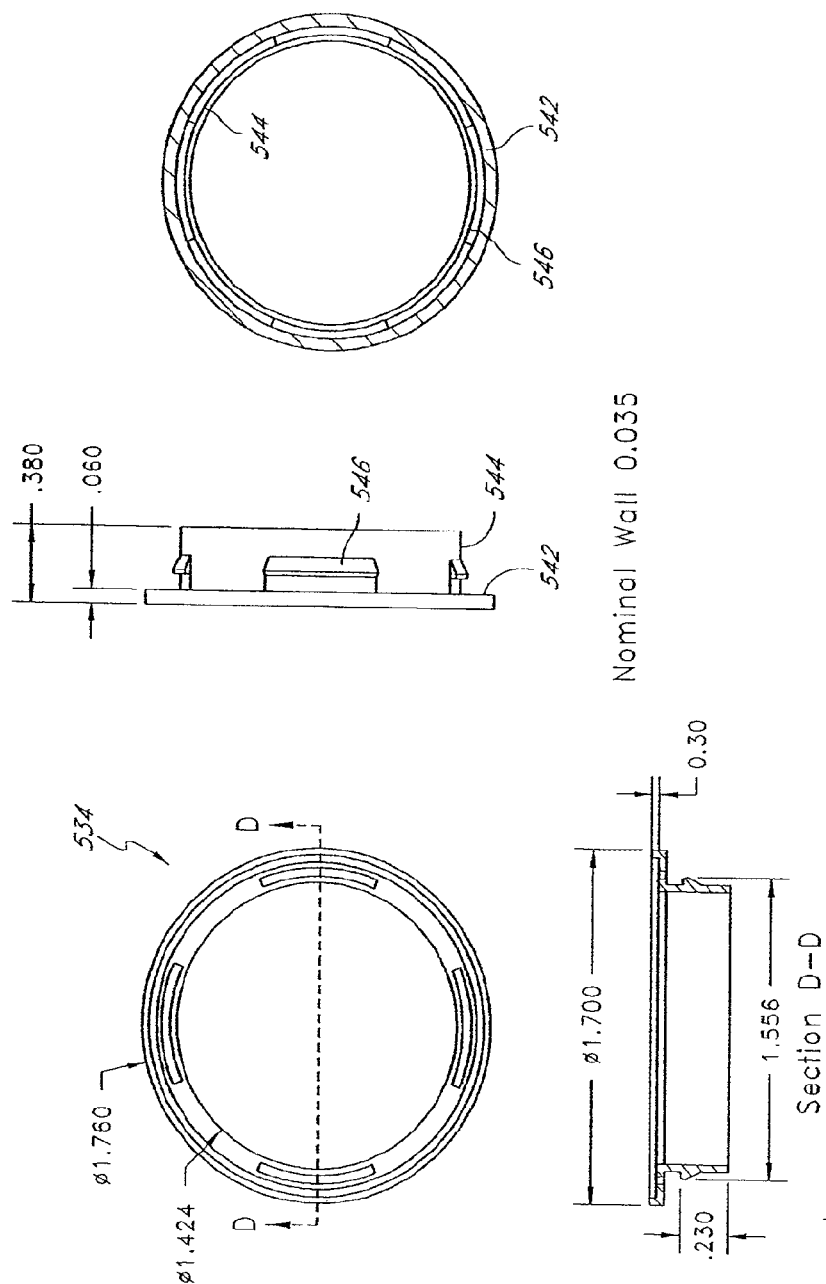
FIG. 20 schematically illustrates an example first support ring with example dimensions in inches.

FIG. 20 schematically illustrates an example first support ring 534 with example dimensions in inches. In certain embodiments, the first support ring 534 comprises a substantially rigid material. Examples of compatible materials include, but are not limited to, plastic (e.g., acrylonitrile butadiene styrene or ABS). As illustrated in FIG. 20, the first support ring 534 of certain embodiments is configured to be mounted in a corresponding aperture 512 of the body 510. The example first support ring 534 illustrated in FIG. 20 comprises a generally flat portion 542, an annular portion 544, and one or more protrusions 546 configured to connect to the second support ring 536, described more fully below. The generally flat portion 542 has an outer diameter which is larger than the diameter of the corresponding aperture 512 of the body 510 and is configured to be mechanically coupled to the body 510 (e.g., by adhesive). The annular portion 544 has an outer diameter which is smaller than or equal to the diameter of the corresponding aperture 512 of the body 510 and is configured to fit through the aperture 512. The one or more protrusions 546 extend generally radially from the annular portion 544 such that the overall width of the protrusions 546 and the annular portion 544 is larger than the diameter of the corresponding aperture 512 of the body 510.

Figure 21:
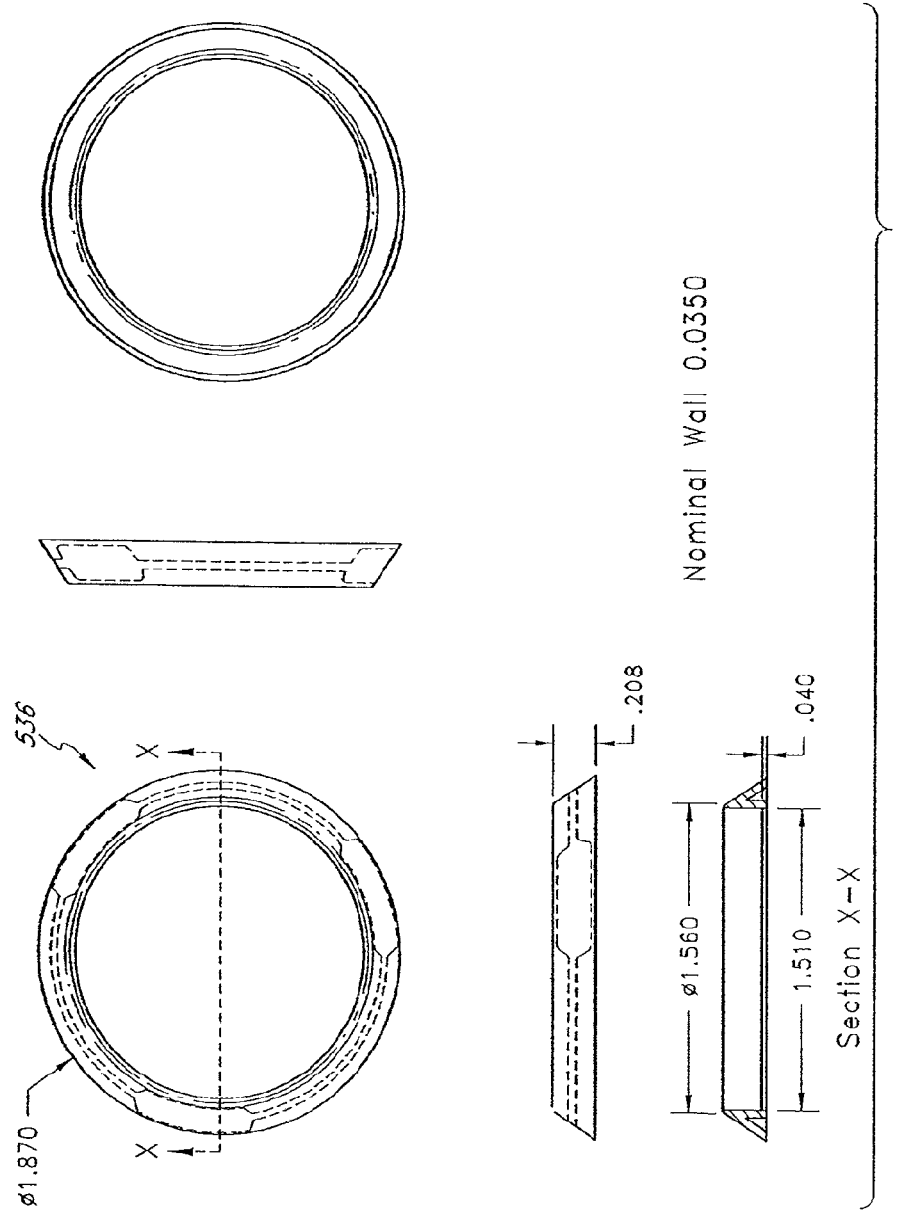
FIG. 21 schematically illustrates an example second support ring with example dimensions in inches.

FIG. 21 schematically illustrates an example second support ring 536 with example dimensions in inches. In certain embodiments, the second support ring 536 comprises a substantially rigid material. Examples of compatible materials include, but are not limited to, plastic (e.g., acrylonitrile butadiene styrene or ABS). As illustrated in FIG. 21, the second support ring 536 of certain embodiments is configured to be connected to the one or more protrusions 546 and the annular portion 544 of the first support ring 534. In certain embodiments, the second support ring 536 comprises one or more recesses (not shown) which are configured to fit with the one or more protrusions 546 of the first support ring 534. In certain such embodiments, the first support ring 534 and the second support ring 536 interlock together to advantageously hold the element 520 in place on the body 510. In certain other embodiments, the first support ring 534 comprises one or more recesses configured to mate with one or more corresponding protrusions of the second support ring 536.

Figure 22:
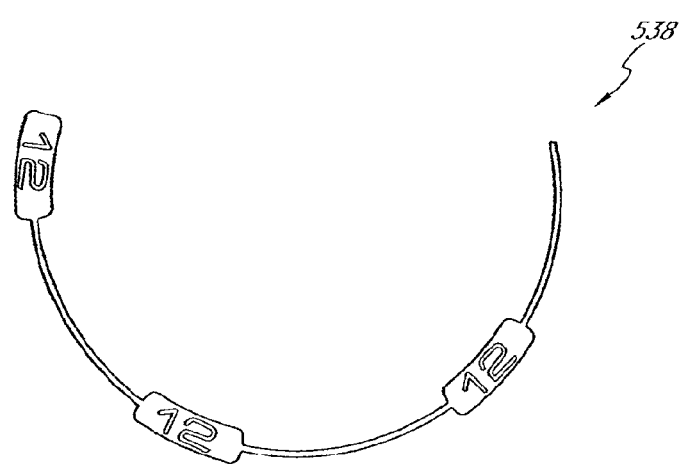
FIG. 22 schematically illustrates an example label compatible with certain embodiments described herein.

FIG. 22 schematically illustrates an example label 538 compatible with certain embodiments described herein. The labels 538 advantageously provide one or more numbers, letters, or symbols (e.g., bar codes) to each of the elements 520 to distinguish the various elements 520 from one another. In certain such embodiments, the labels 538 comprise a vinyl material and are mechanically coupled to the second support ring 536 (e.g., by adhesive) so as to be visible to users of the light therapy apparatus. Other types of labels 538 are also compatible with embodiments disclosed herein, including but not limited to, labels 538 which are painted or etched onto an outside surface of the second support ring 536.

Figure 23B:
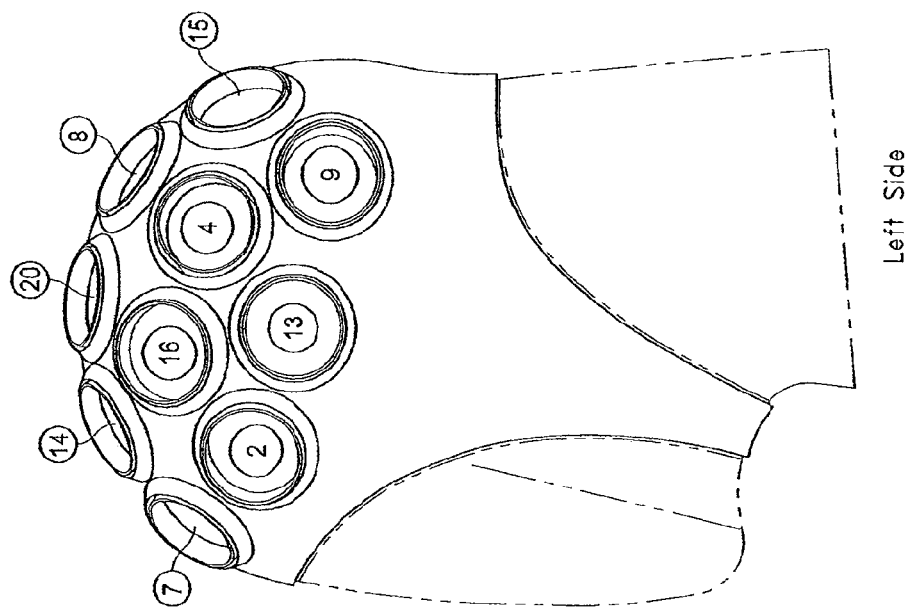
FIGS. 23A and 23B schematically illustrate an example labeling configuration for the apparatus on the left-side and right-side of the apparatus.
Figure 23A:
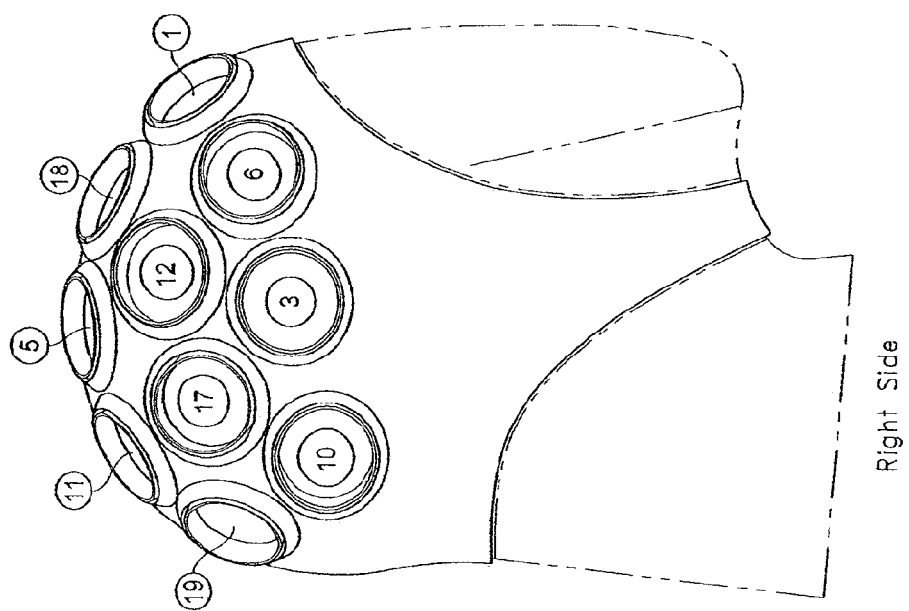
Figure 23C:
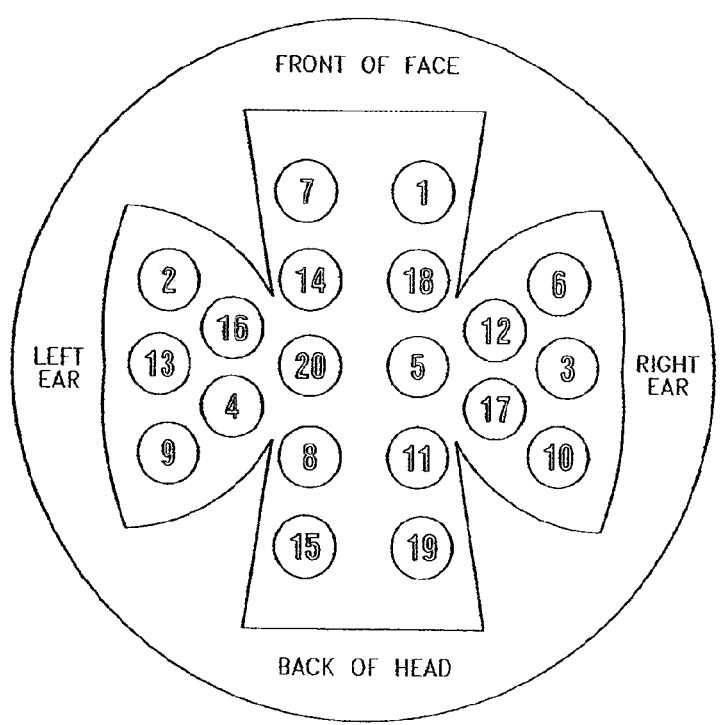
FIG. 23C schematically illustrates the example labeling configuration of FIGS. 23A and 23B from above a flattened view of the apparatus.

FIGS. 23A and 23B schematically illustrate the left-side and right-side of the apparatus 500, respectively, showing an example labeling configuration for the apparatus 500. FIG. 23C schematically illustrates the example labeling configuration of FIGS. 23A and 23B from above a flattened view of the apparatus 500. The labeling convention of FIGS. 23A-23C is compatible with irradiation of both halves of the patient's brain. Other labeling conventions are also compatible with embodiments described herein.

In certain embodiments, the labels 538 are advantageously used to guide an operator to irradiate the patient's brain at the various treatment sites sequentially at each of the treatment sites one at a time through the elements 520 in a predetermined order using a light source which can be optically coupled to sequential elements 520. For example, for the labeling configuration of FIGS. 23A-23C, the operator can first irradiate element "1," followed by elements "2,"

"3," "4," etc. to sequentially irradiate each of the twenty treatment sites one at a time. In certain such embodiments, the order of the elements 520 is selected to advantageously reduce temperature increases which would result from sequentially irradiating elements 520 in proximity to one another.

In certain embodiments, the labels 538 are advantageously used to keep track of which elements 520 have been irradiated and which elements 520 are yet to be irradiated. In certain such embodiments, at least a portion of each label 538 (e.g., a pull-off tab) is configured to be removed from the apparatus 500 when the corresponding element 520 has been irradiated. In certain embodiments, the label 538 has a code sequence which the operator enters into the controller prior to irradiation so as to inform the controller of which element 520 is next to be irradiated. In certain other embodiments, each label 538 comprises a bar code or a radio-frequency identification device (RFID) which is readable by a sensor electrically coupled to the controller. The controller of such embodiments keeps track of which elements 520 have been irradiated, and in certain such embodiments, the controller only actuates the light source when the light source is optically coupled to the proper element 520.

Figure 24A:
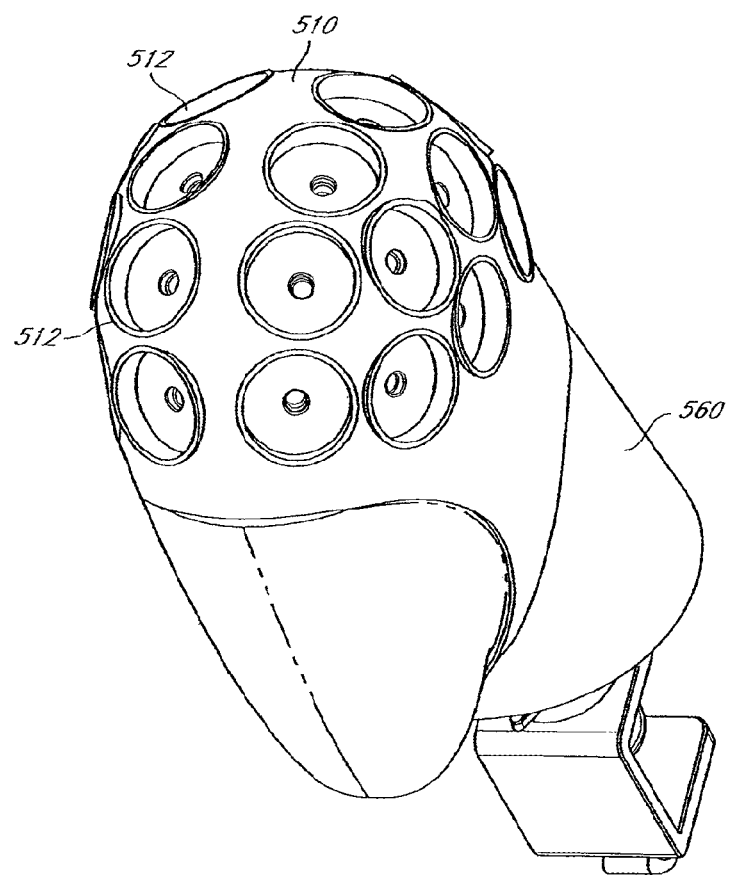
FIGS. 24A-24E schematically illustrate various stages of structures formed during the fabrication of the apparatus of FIGS. 17-22.
Figure 24B:
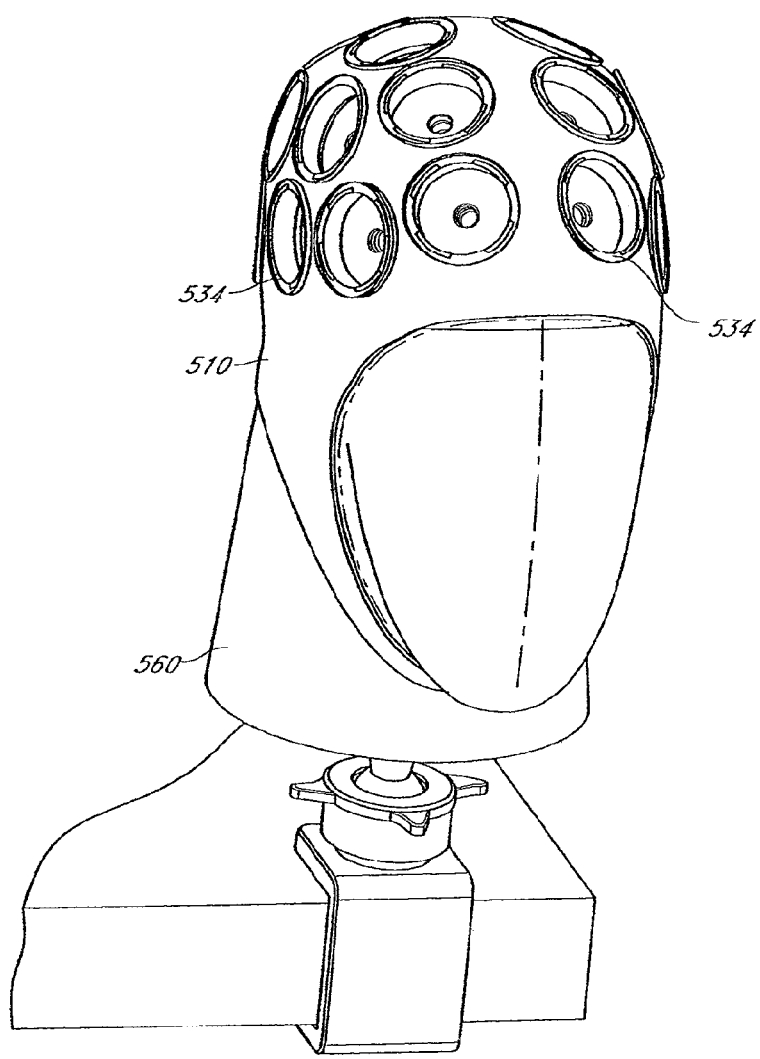
Figure 24C:
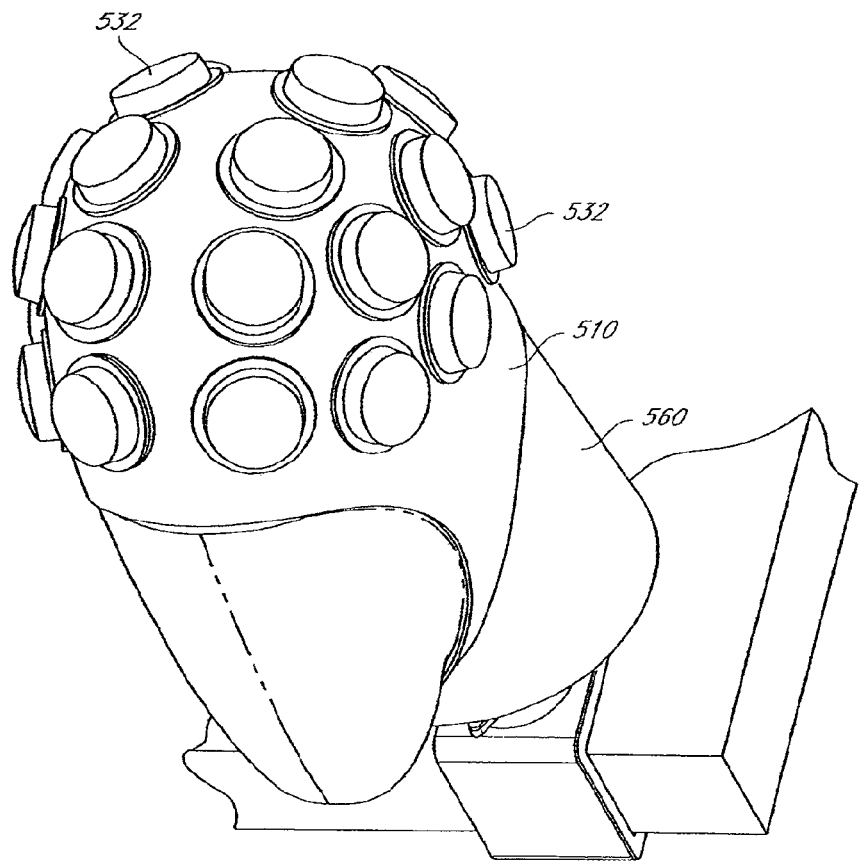
Figure 24D:
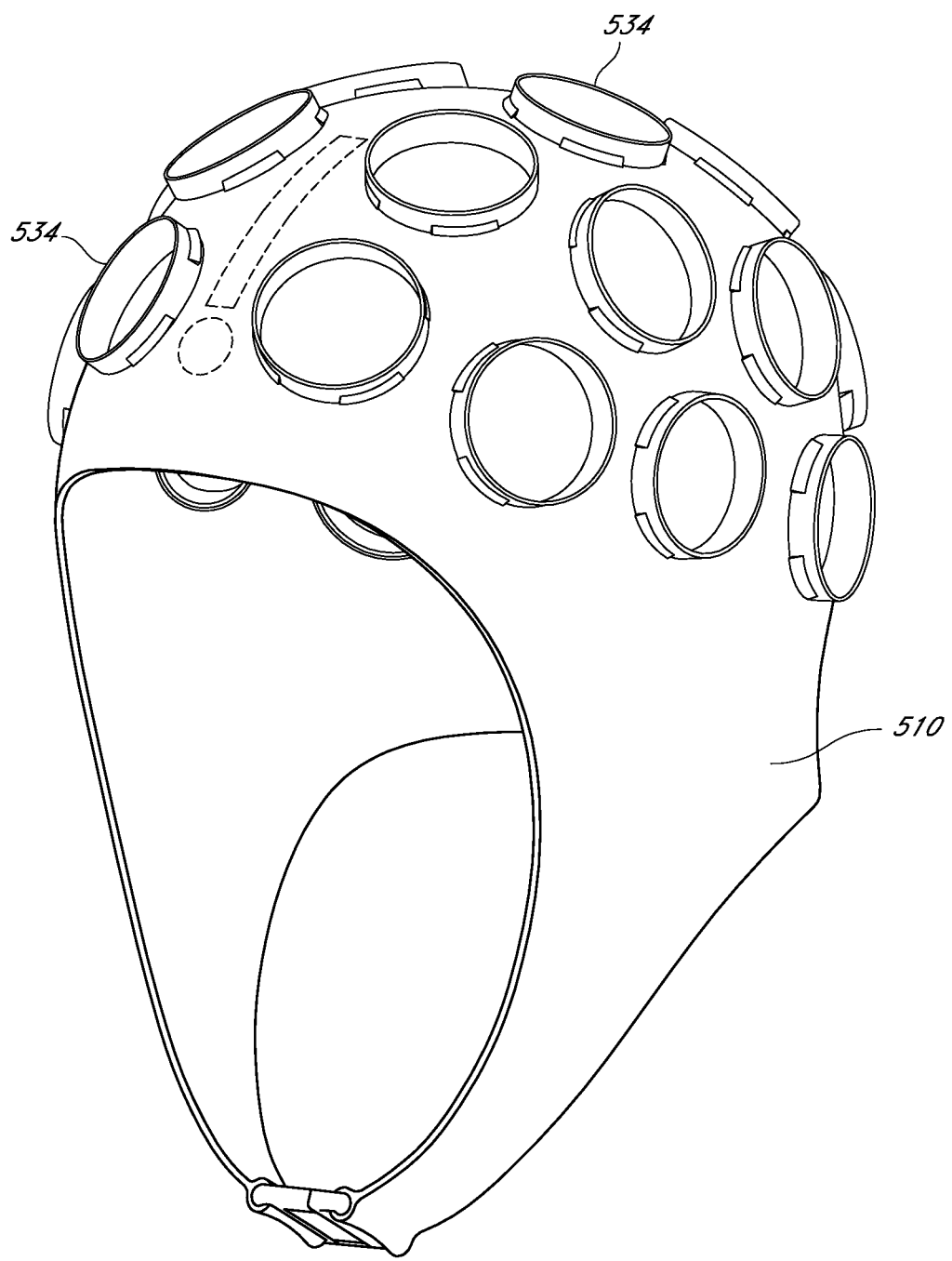
Figure 24E:
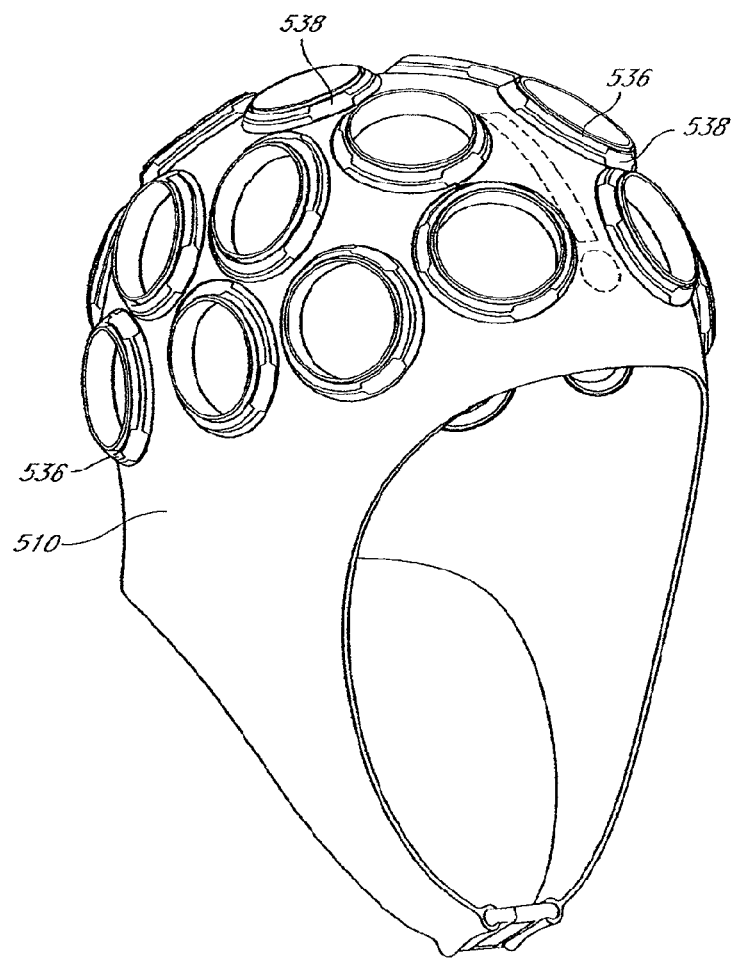

FIGS. 24A-24E schematically illustrate various stages of structures formed during the fabrication of the apparatus 500 of FIGS. 17-22. FIG. 24A schematically illustrates the body 510 mounted on a mannequin head fixture 560. The body 510 is mounted in an inside-out configuration and is shown in FIG. 24A after each of the apertures 512 has been cut in the body 510. In each of the apertures 512, a first support ring 534 is connected to the body 510, as shown in FIG. 24B. In certain embodiments, a layer of adhesive (e.g., CA40 Scotch-Weld™ instant adhesive available from 3M Company of Saint Paul, Minn.) is applied to a surface of the flat portion 542 which is then pressed onto the body 510 with the annular portion 544 extending through the aperture 512. FIG. 24C schematically illustrates the optical components 532 mounted on each of the first support rings 534. In certain embodiments, a layer of adhesive (e.g., Loctite® 3105 ultraviolet-cured adhesive available from Henkel Corporation of Rocky Hill, Conn.) is applied to a surface of the flat portion 542 which is then pressed together with a corresponding surface of the optical component 532 and the adhesive is cured by application of ultraviolet light. FIG. 24D schematically illustrates the body 510 after being removed from the mannequin head fixture 560 and returned to an right-side-out configuration. FIG. 24E schematically illustrates the apparatus 500 after the second support rings 536 have been mounted to the first support rings 534 and the labels 538 have been applied to the second support rings 536.

Figure 25:
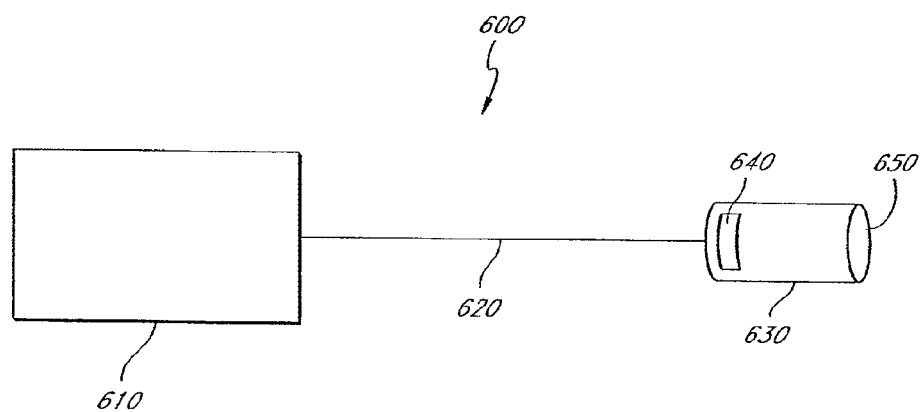
FIG. 25 schematically illustrates an apparatus which emits light for irradiating a patient's skin to treat portions of a patient's body underneath the patient's skin.

FIG. 25 schematically illustrates an apparatus 600 which emits light for irradiating a patient's skin to treat portions of a patient's body underneath the patient's skin. The apparatus 600 comprises a source 610 of light having a wavelength which is substantially transmitted by the patient's skin. The apparatus 600 further comprises an optical conduit 620 optically coupled to the source 610. The apparatus 600 further comprises an optical device 630 optically coupled to the optical conduit 620. The optical device 630 comprises an optical diffuser 640 optically coupled to the optical conduit 620. The optical device 630 further comprises an output optical element 650 comprising a rigid and substantially thermally conductive material. The output optical element 650 is optically coupled to the optical conduit 620 (e.g., via the optical diffuser 640). A portion of the light transmitted through the patient's skin irradiates at least a portion of the patient's body underneath the patient's skin with an efficacious power density of light.

In certain embodiments, the source 610 comprises a laser which emits light having at least one wavelength in a range between about 630 nanometers and about 1064 nanometers. The laser of certain other embodiments emits light having at least one wavelength in a range between about 780 nanometers and about 840 nanometers. In certain embodiments, the laser emits light having a center wavelength of approximately 808 nanometers. The laser of certain embodiments is capable of generating up to approximately 6 watts of laser light and has a numerical aperture of approximately 0.16.

Figure 26:
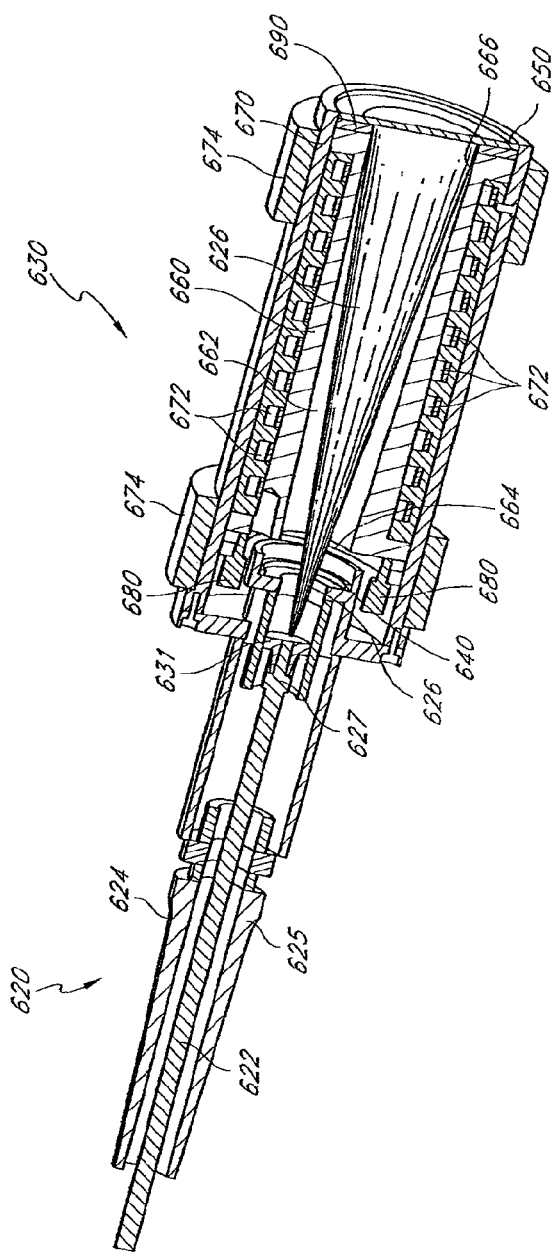
FIG. 26 schematically illustrates an example optical conduit optically coupled to an example optical device.

FIG. 26 schematically illustrates an example optical conduit 620 optically coupled to an example optical device 630. In certain embodiments, the optical conduit 620 comprises an optical fiber 622 and a protective sheath 624 around the optical fiber. The optical fiber 622 of certain embodiments is a step-index optical fiber having a numerical aperture of approximately 0.22 (e.g., a 1-millimeter diameter multi-mode fiber). In certain embodiments, the optical conduit 620 further comprises an electrically conductive conduit to transmit signals between the optical device 630 and the source 610 (e.g., from trigger switches or temperature sensors within the optical device 630) and/or to provide electrical power to the optical device 630 (e.g., for a thermoelectric cooler).

In certain embodiments, the protective sheath 624 comprises a strain relief apparatus 625 and a SMA connector 627 which mechanically couples to a corresponding adjustable SMA mount 631 of the optical device 630. The protective sheath 624 of certain embodiments has a plurality of rigid segments, with each segment having a generally cylindrical tubular shape and a longitudinal axis. Each segment is articulately coupled to neighboring segments such that an angle between the longitudinal axes of neighboring segments is limited to be less than a predetermined angle. In certain embodiments, the protective sheath 624 allows the optical conduit 620 to be moved and to bend, but advantageously limits the radius of curvature of the bend to be sufficiently large to avoid breaking the optical fiber 622 therein.

The example optical device 630 schematically illustrated by FIG. 26 comprises an optical diffuser 640 and an output optical element 650 (e.g., a lens). In certain embodiments, the output optical element 650 comprises glass (e.g., BK7 glass) which is substantially optically transmissive at wavelengths which are substantially transmitted by skin, but is not substantially thermally conductive. In certain other embodiments, the output optical element 650 is rigid, substantially optically transmissive at wavelengths which are substantially transmitted by skin, and substantially thermally conductive.

In certain embodiments, the output optical element 650 has a front surface facing generally towards the patient's scalp and a back surface facing generally away from the patient's scalp. In certain embodiments, the front surface is adapted to be placed in contact with either the skin or with an intervening material in contact with the skin during irradiation. In certain such embodiments, the thermal conductivity of the output optical element 650 is sufficient to allow heat to flow from the front surface of the output optical element 650 to a heat sink in thermal communication with the back surface of the output optical element 650. In certain embodiments, the output optical element 650 conducts heat from the front surface to the back surface at a sufficient rate to prevent, minimize, or reduce damage to the skin or discomfort to the patient from excessive heating of the skin due to the irradiation.

The existence of air gaps between the output optical element 650 and the scalp can create a problem in controlling the heating of the skin by the irradiation. In certain embodiments, the output optical element 650 is placed in contact with the skin of the scalp so as to advantageously avoid creating air gaps between the output optical element 650 and the skin. In certain other embodiments in which an intervening material is in contact with the skin and with the output optical element 650, the output optical element 650 is placed in contact with the intervening material so as to advantageously avoid creating air gaps between the output optical element 650 and the intervening material or between the intervening material and the skin.

In certain embodiments, the thermal conductivity of the output optical element 650 has a thermal conductivity of at least approximately 10 watts/meter-K. In certain other embodiments, the thermal conductivity of the output optical element 650 is at least approximately 15 watts/meter-K. Examples of materials for the output optical element 650 in accordance with certain embodiments described herein include, but are not limited to, sapphire which has a thermal conductivity of approximately 23.1 watts/meter-K, and diamond which has a thermal conductivity between approximately 895 watts/meter-K and approximately 2300 watts/meter-K.

In certain embodiments, the optical diffuser 640 receives and diffuses light 626 emitted from the optical coupler 620 to advantageously homogenize the light beam prior to reaching the output optical element 650. Generally, tissue optics is highly scattering, so beam non-uniformity less than approximately 3 millimeters in size has little impact on the illumination of the patient's cerebral cortex. In certain embodiments, the optical diffuser 640 advantageously homogenizes the light beam to have a non-uniformity less than approximately 3 millimeters. In certain embodiments, the optical diffuser 640 has a diffusing angle of approximately one degree.

In certain embodiments, the output optical element 650 receives the diffused light 626 propagating from the optical diffuser 640 and emits the light 626 out of the optical device 630. In certain embodiments, the output optical element 650 comprises a collimating lens. In certain embodiments, the light beam emitted from the output optical element 650 has a nominal diameter of approximately 30 millimeters. The perimeter of the light beam used to determine the diameter of the beam is defined in certain embodiments to be those points at which the intensity of the light beam is $1/e^2$ of the maximum intensity of the light beam. The maximum-useful diameter of certain embodiments is limited by the size of the patient's head and by the heating of the patient's head by the irradiation. The minimum-useful diameter of certain embodiments is limited by heating and by the total number of treatment sites that could be practically implemented. For example, to cover the patient's skull with a beam having a small beam diameter would correspondingly use a large number of treatment sites. In certain embodiments, the time of irradiation per treatment site can be adjusted accordingly to achieve a desired exposure dose. In certain embodiments, the beam intensity profile has a semi-Gaussian profile, while in certain other embodiments, the beam intensity profile has a "top hat" profile.

In certain embodiments, the optical device 630 comprises an optical lens which receives light from the optical conduit 620 and transmits the light to the output optical element 650. In certain such embodiments, the output optical element 650 comprises an optical diffuser. In certain embodiments, the output optical element 650 comprises both an optical lens and an optical diffuser.

In certain embodiments, the optical device 630 further comprises a heat sink 660 thermally coupled to the output optical element 650 (e.g., by a thermal adhesive, such as Resinlab EP1200 available from Ellsworth Adhesives of Germantown, Wis.). By having the thermally conductive output optical element 650 thermally coupled to the heat sink 660, certain embodiments advantageously provide a conduit for heat conduction away from the treatment site (e.g., the skin). In certain embodiments, the output optical element 650 is pressed against the patient's skin and transfers heat away from the treatment site. In certain other embodiments in which the output optical element 650 is pressed against an element 520 which contacts the patient's skin, as described above, the element 520 advantageously provides thermal conduction between the patient's skin and the output optical element 650.

As schematically illustrated by FIG. 26, the heat sink 660 of certain embodiments comprises a reflective inner surface 662, a first end 664, and a second end 666. The heat sink 660 is positioned so that light 626 from the optical diffuser 640 is transmitted into the first end 664, through the heat sink 660, out of the second end 666, and to the output optical element 650. The inner surface 662 of certain embodiments is substantially cylindrical, while for certain other embodiments, the inner surface 662 is substantially conical. In certain embodiments having a conical inner surface 662, the inner surface 662 at the first end 664 has a first inner diameter and the inner surface 662 at the second end 666 has a second inner diameter larger than the first inner diameter.

In certain embodiments, the heat sink 660 comprises aluminum and the reflective inner surface is gold-plated. In certain other embodiments, the reflective inner surface 662 is roughened (e.g., by grit sandblasting) to reduce specular reflections of light from the inner surface 662.

In certain embodiments, as schematically illustrated by FIG. 26, the optical device 630 further comprises a housing 670 comprising a plurality of ventilation slots 672. The ventilation slots 672 of certain embodiments allow air flow to remove heat from the heat sink 660, thereby cooling the heat sink 660.

In certain embodiments, the housing 670 is sized to be easily held in one hand (e.g., having a length of approximately 5½ inches). The housing 670 of certain embodiments further comprises one or more protective bumpers 674 comprising a shock-dampening material (e.g., rubber). The housing 670 of certain embodiments is configured so that the optical device 630 can be held in position and sequentially moved by hand to irradiate selected portions of the patient's skin.

In certain embodiments, as schematically illustrated by FIG. 26, the optical device 630 further comprises at least one trigger switch 680. The trigger switch 680 is electrically coupled to the source 610. The trigger switch 680 of certain embodiments is actuated by pressing the output optical element 650 against a surface. The source 610 of certain embodiments is responsive to the trigger switch 680 by emitting light only when the trigger switch 680 is actuated. Therefore, in certain such embodiments, to utilize the optical device 630, the output optical element 650 is pressed against the patient's skin or against an element 520, such as described above.

In certain embodiments, the optical device 630 further comprises a thermoelectric cooler 690 thermally coupled to the output optical element 650, as schematically illustrated by FIG. 26. The thermoelectric cooler 690 of certain embodiments has a cool side thermally coupled to the output optical element 650 and a hot side which is thermally coupled to the heat sink 660. The thermoelectric cooler 690 of certain embodiments advantageously removes heat from the output optical element 650. Certain embodiments of the optical device 630 comprising a thermoelectric cooler 690 which actively cools the patient's skin thereby advantageously avoiding large temperature gradients at the patient's skin which would otherwise cause discomfort to the patient. In certain embodiments, the optical device 630 further comprises one or more temperature sensors (e.g., thermocouples, thermistors) which generate electrical signals indicative of the temperature of the output optical element 650 or other portions of the optical device 630.

Figure 27:
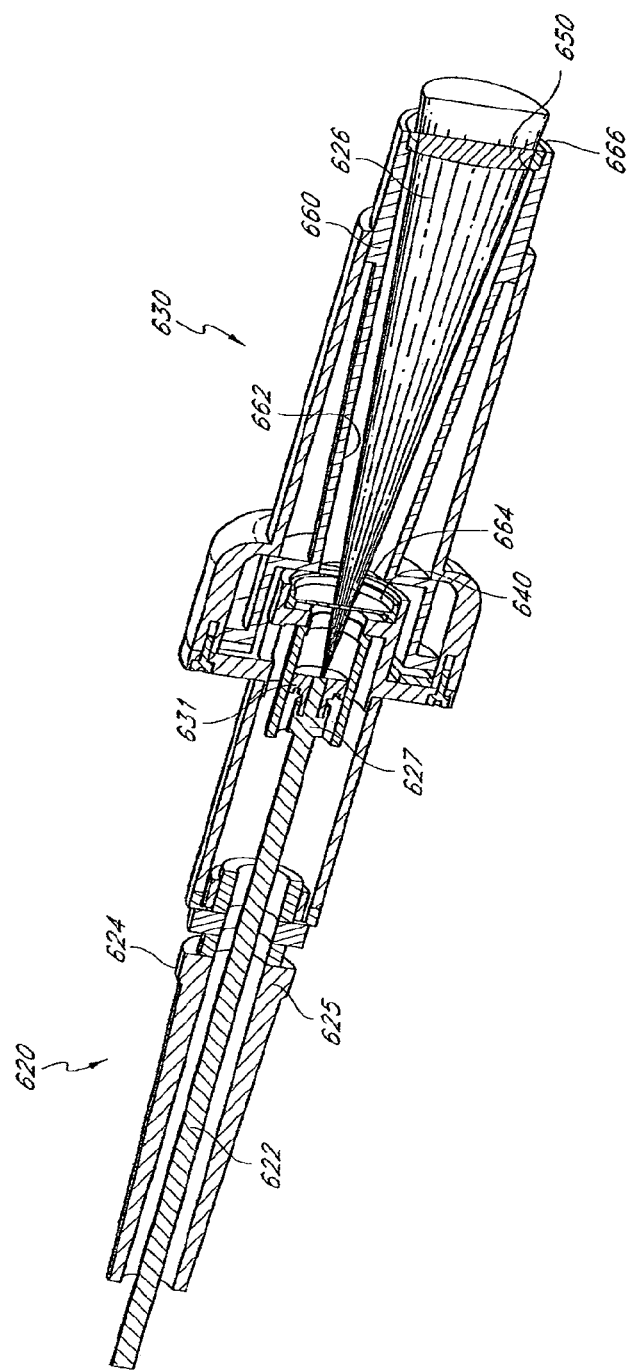
FIG. 27 schematically illustrates a simplified optical device compatible with certain embodiments described herein.
Figure 30:
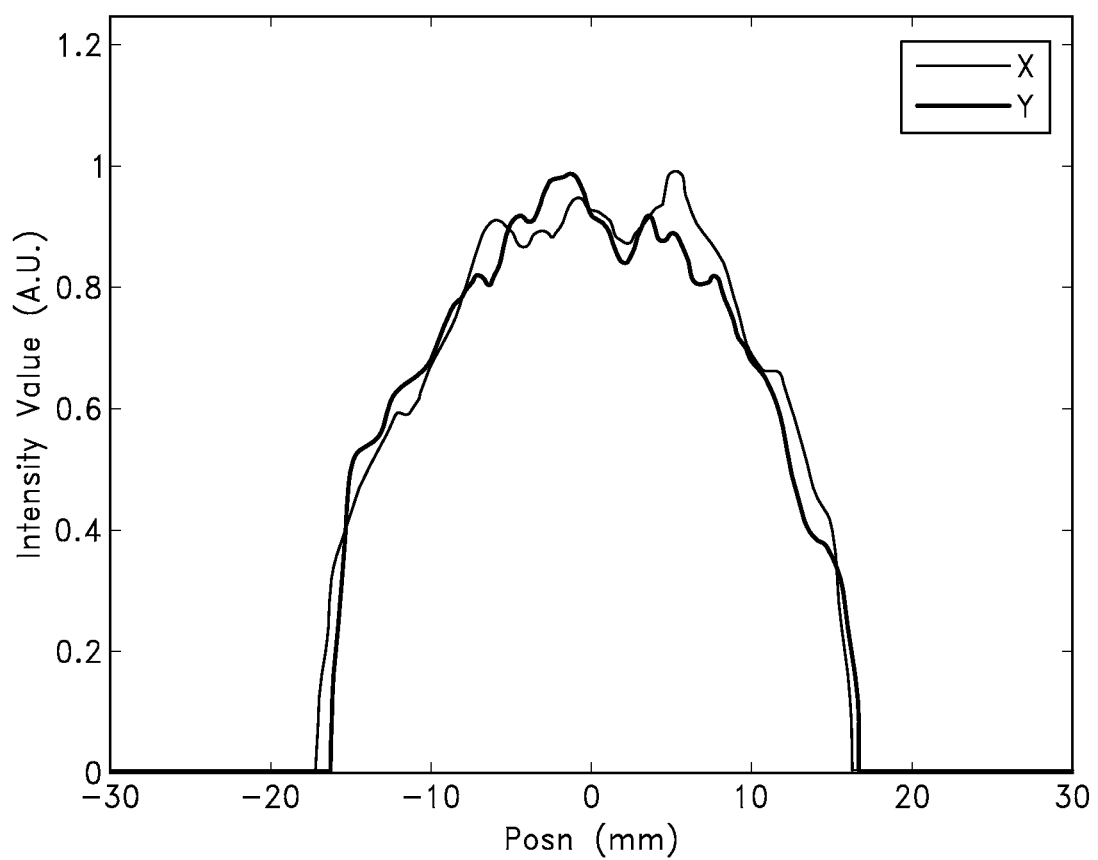
FIG. 30 illustrates two beam profile cross-sections of a light beam emitted from the optical device of FIG. 27 having a grit sandblasted conical inner surface.

FIG. 27 schematically illustrates a simplified optical device 630 compatible with certain embodiments described herein. The optical device 630 of FIG. 27 has a smaller heat sink 660 and does not have a thermoelectric cooler. As schematically illustrated by FIG. 30, the heat sink 660 of certain embodiments comprises a reflective conical inner surface 662 having a first end 664 with a first inner diameter and a second end 666 with a second inner diameter larger than the first inner diameter. In certain embodiments, the optical device 630 of FIG. 27 is advantageously smaller, lighter, and more easily maneuvered by hand than the optical device 630 of FIG. 26.

Figure 28A:
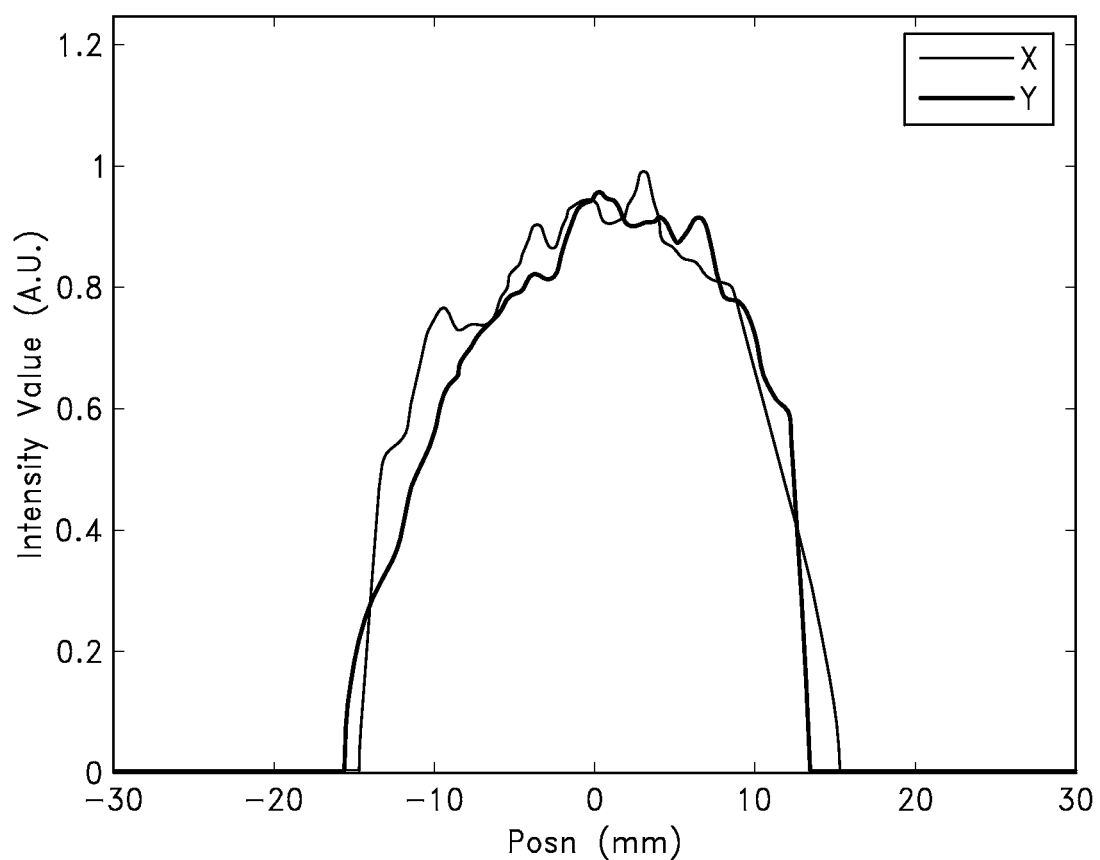
FIG. 28A illustrates two beam profile cross-sections of a light beam emitted from the optical device of FIG. 26 with the planes of the two cross-sections of FIG. 28A generally perpendicular to one another and to the output optical element.
Figure 28B:
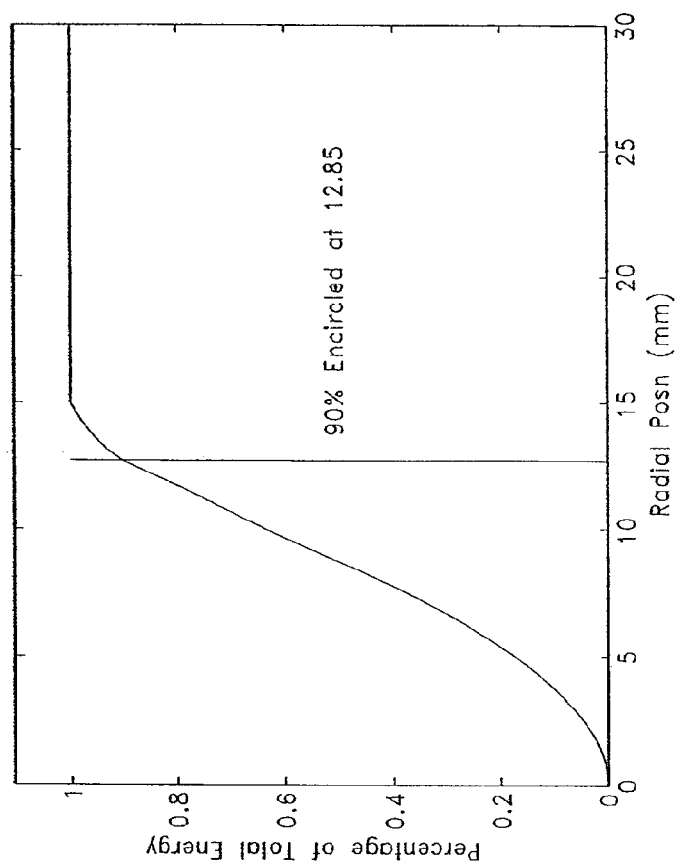
FIG. 28B illustrates the encircled energy of a light beam emitted from the optical device of FIG. 26.

FIG. 28A illustrates two beam profile cross-sections of a light beam emitted from the optical device 630 of FIG. 26 with the planes of the two cross-sections of FIG. 28A generally perpendicular to one another and to an output optical element 650 comprising a lens. The beam diameter of FIG. 28A is approximately 30 millimeters. FIG. 28B illustrates the encircled energy of a light beam emitted from the optical device 630 of FIG. 26. Approximately 90% of the encircled energy falls within a diameter of approximately 25.7 millimeters.

Figure 29A:
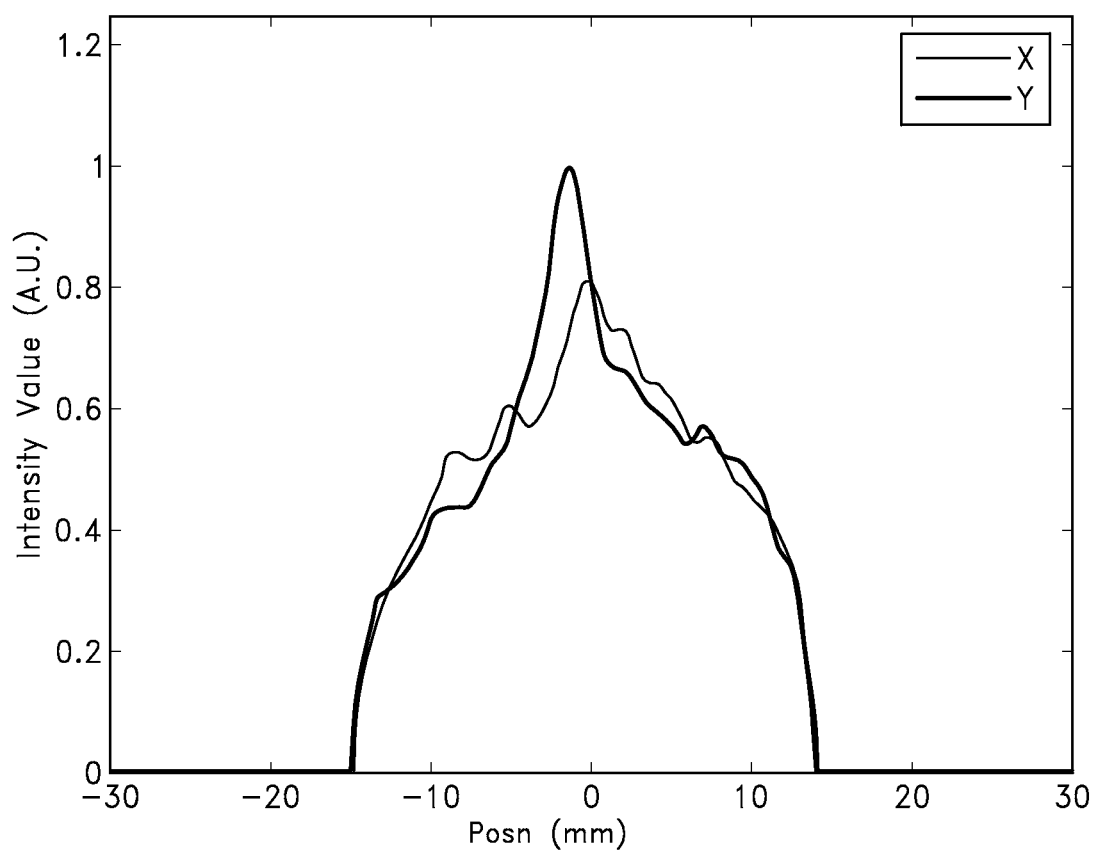
FIG. 29A illustrates two beam profile cross-sections of a light beam emitted from the optical device of FIG. 27 having a smooth gold-plated conical inner surface.
Figure 29B:
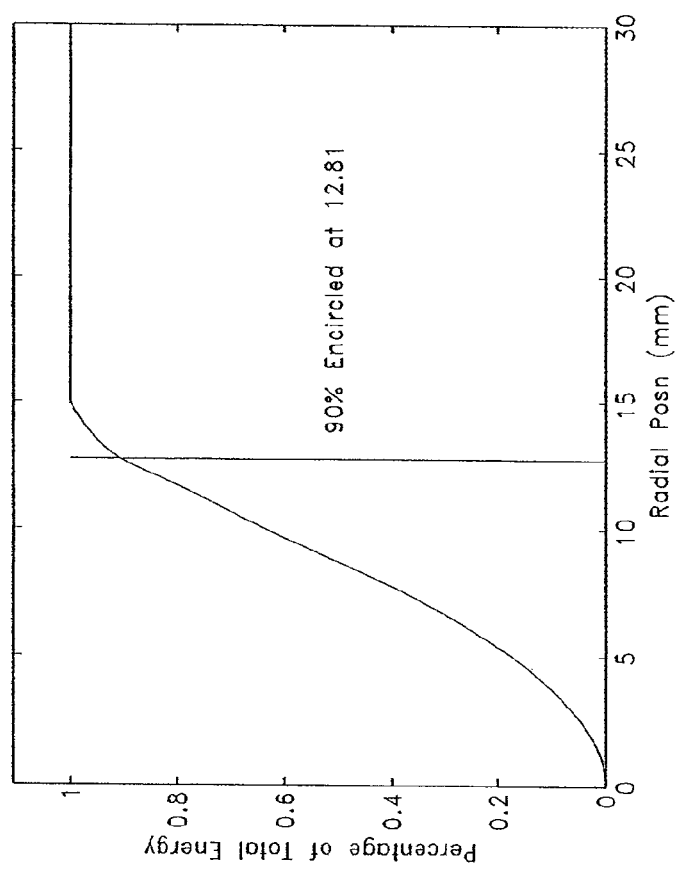
FIG. 29B illustrates the encircled energy of a light beam emitted from the optical device of FIG. 27.

FIG. 29A illustrates two beam profile cross-sections of a light beam emitted from the optical device 630 of FIG. 27 having a smooth gold-plated conical inner surface 662. The planes of the two cross-sections of FIG. 29A are generally perpendicular to one another and to the output optical element 650. The beam diameter of FIG. 29A is approximately 30 millimeters. The light beam has a high flux region near the center of the beam profile. This high flux region qualifies as a hot spot, where a hot spot is defined as regions of the light beam in which the local flux, averaged over a 3 millimeter by 3 millimeter area, is more than 10% larger than the average flux. FIG. 29B illustrates the encircled energy of a light beam emitted from the optical device 630 of FIG. 27. Approximately 90% of the encircled energy falls within a diameter of approximately 25.6 millimeters.

In certain embodiments having a smooth inner surface 662, multiple reflections of light emitted from the optical fiber 622 at large enough angles are focused near the output optical element 650, contributing to the hot spot region of the beam profile. FIG. 30 illustrates two beam profile cross-sections of a light beam emitted from the optical device 630 of FIG. 27 having a grit sandblasted conical inner surface 662. This inner surface 662 is roughened to reduce the amount of specular reflections from the inner surface 662. In certain such embodiments, the beam profile does not have a hot spot region. Certain embodiments of the optical device 630 advantageously generate a light beam substantially without hot spots, thereby avoiding large temperature gradients at the patient's skin which would otherwise cause discomfort to the patient.

Figure 31A:
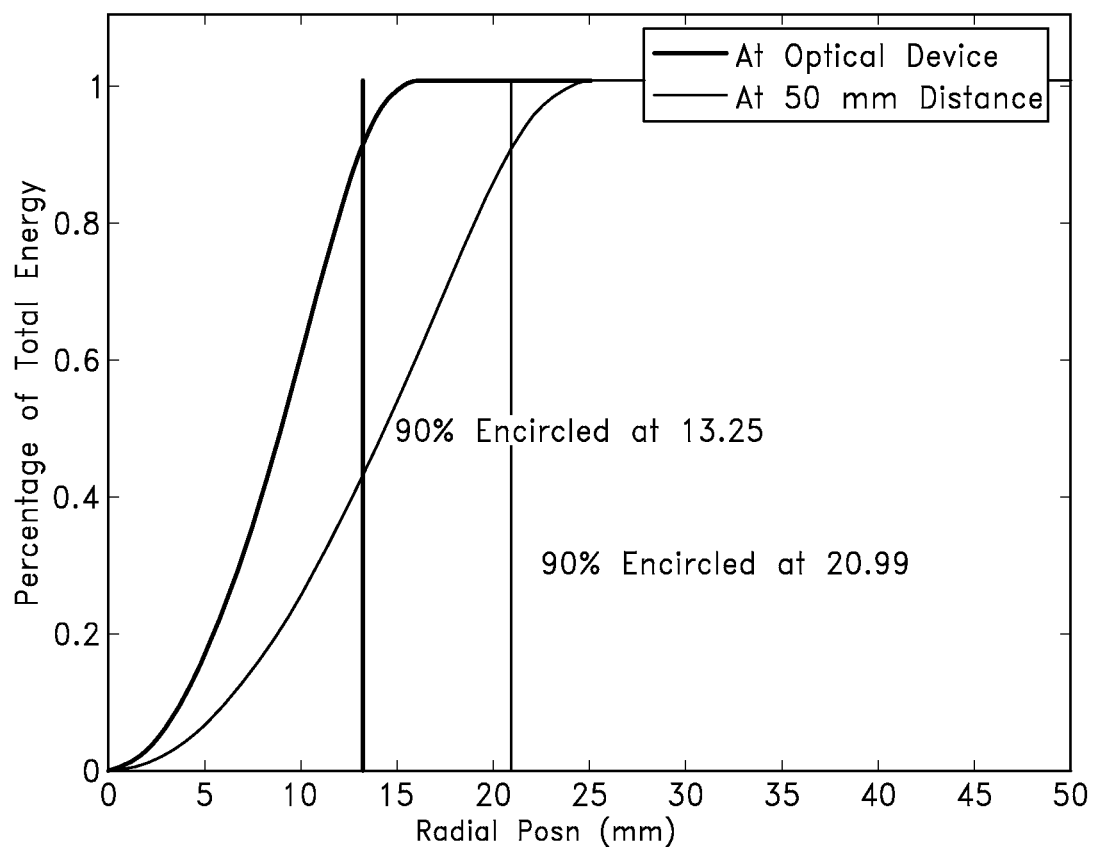
FIGS. 31A and 31B illustrate the beam divergence for the optical device of FIG. 26 and of FIG. 27 (with a sandblasted inner surface), respectively.
Figure 31B:
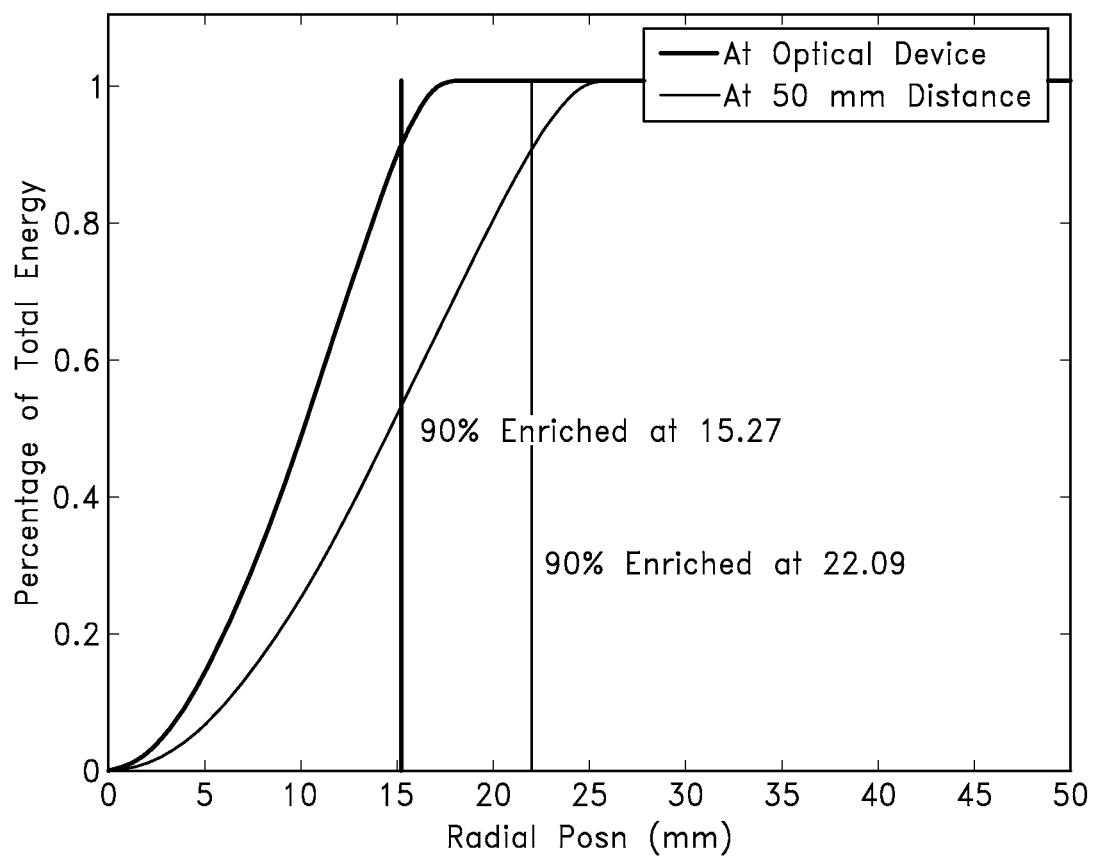

In certain embodiments, the beam divergence emitted from the output optical element 650 is significantly less than the scattering angle of light inside the body tissue being irradiated, which is typically several degrees. FIGS. 31A and 31B illustrate the beam divergence for the optical device 630 of FIG. 26 and of FIG. 27 (with the sandblasted inner surface 622), respectively. The beam divergence was measured by measuring the beam profile at two separate planes and comparing the increase in beam diameter (e.g., the diameter that encircled 90% of the energy) further from the output optical element 650. In certain embodiments, the beam divergence has a full angle of about 12 degrees. The numerical aperture of the optical device 630 of FIG. 26 is approximately 0.152 and the numerical aperture of the optical device 630 of FIG. 27 is approximately 0.134, which equates to a difference of less than approximately 2.5 degrees.

Light Parameters

It is desirable to apply an efficacious amount of light energy to the internal tissue to be treated using light sources positioned outside the body, as schematically illustrated in the Figures discussed herein. Examples of use of external light energy to treat internal tissues are disclosed in U.S. Pat. Nos. 6,537,304 and 6,918,922, both of which are incorporated in their entireties by reference herein.

The various parameters of the light beam emitted from the emission surface of the light source are advantageously selected to provide treatment while controlling, inhibiting, preventing, minimizing, or reducing injury or discomfort to the patient due to heating of the skin, tissue, or bone by the light. While discussed separately, these various parameters below can be combined with one another within the disclosed values in accordance with embodiments described herein.

Wavelength

The following section discusses theories and potential action mechanisms, as they presently appear to the inventors, regarding the selection of wavelengths for certain embodiments of phototherapy described herein. The scope of the claims of the present application is not to be construed to depend on the accuracy, relevance, or specifics of any of these theories or potential action mechanisms. Thus the claims of the present application are to be construed without being bound by theory or by a specific mechanism.

In certain embodiments, non-invasive delivery and heating by the electromagnetic radiation place practical limits on the ranges of electromagnetic radiation wavelengths to be used in the treatment of the patient's brain. In certain embodiments, the wavelength of electromagnetic radiation used in the treatment of the patient's brain is selected in view of one or more of the following considerations: (1) the ability to stimulate mitochondrial function in vitro; (2) the ability to penetrate tissue; (3) the absorption in the target tissue; (4) the efficacy in ischemia models in vivo; (5) the availability of laser sources with the desired power at the desired wavelength or wavelengths; and (6) the ability to stimulate beneficial responses in cells used in cell therapy (e.g., stem cells) or the tissues to which those cells are delivered. The combination of these effects offers few wavelengths to be used as a therapeutic agent in vivo. These factors can be combined in certain embodiments to create an efficiency factor for each wavelength. Wavelengths around 800 nanometers are particularly efficient. In addition, 808-nanometer light has previously been found to stimulate mitochondrial function and to work in the myocardial infarction models in rat and dog. The following discussion deals with these considerations in more detail.

In certain embodiments, the light source 40 generates light which is substantially monochromatic (i.e., light having one wavelength, or light having a narrow band of wavelengths). So that the amount of light transmitted to the brain is maximized, the wavelength of the light is selected in certain embodiments to be at or near a transmission peak (or at or near an absorption minimum) for the intervening tissue. In certain such embodiments, the wavelength corresponds to a peak in the transmission spectrum of tissue at about 820 nanometers. In other embodiments, the wavelength of the light is preferably between about 630 nanometers and about 1064 nanometers, more preferably between about 780 nanometers and about 840 nanometers, and most preferably includes wavelengths of about 785, 790, 795, 800, 805, 810, 815, 820, 825, or 830 nanometers. An intermediate wavelength in a range between approximately 730 nanometers and approximately 750 nanometers (e.g., about 739 nanometers) appears to be suitable for penetrating the skull, although other wavelengths are also suitable and may be used. In several embodiments, shorter wavelengths are preferred, such as 600 to 700 nm, including 610, 620, 630, 640, 650, 660, 670, 680, 690, and 700 nm.

In certain embodiments, light in the visible to near-infrared wavelength range is used to irradiate the long bones (FIG. 46). In certain embodiments, the light has a wavelength distribution peaked at a peak wavelength and has a linewidth less than ±10 nanometers from the peak wavelength. In certain such embodiments, the light has a linewidth less than 4 nanometers, full width at 90% of energy. In certain embodiments, the center wavelength is (808±10) nanometers with a spectral linewidth less than 4 nanometers, full width at 90% of energy. Longer or shorter wavelengths are used in other embodiments.

In other embodiments, the light source 40 generates light having a plurality of wavelengths (e.g. applied concurrently or sequentially). For example, in certain embodiments, a band of wavelengths of (808±5) nanometers is used. In certain embodiments, the light source 40 is adapted to generate light having a first wavelength concurrently with light having a second wavelength. In certain other embodiments, the light source 40 is adapted to generate light having a first wavelength sequentially with light having a second wavelength.

In certain embodiments, a single light source 40 is used as a light generator to generate light, while in other embodiments, a plurality of light sources 40 are used as a light generator to generate light. The light source 40 preferably generates light in the visible to near-infrared wavelength range. In certain embodiments, the light source 40 comprises one or more laser diodes, which each provide coherent light. In embodiments in which the light from the light source 40 is coherent, the emitted light may produce "speckling" due to coherent interference of the light. This speckling comprises intensity spikes which are created by constructive interference and can occur in proximity to the target tissue being treated. For example, while the average power density may be approximately 10 mW/cm$^2$, the power density of one such intensity spike in proximity to the brain (or other) tissue to be treated may be approximately 300 mW/cm$^2$. In certain embodiments, this increased power density due to speckling can improve the efficacy of treatments using coherent light over those using incoherent light for illumination of deeper tissues.

In certain embodiments, the light source 40 includes at least one continuously emitting GaAlAs laser diode having a wavelength of about 830 nanometers. In another embodiment, the light source 40 comprises a laser source having a wavelength of about 808 nanometers. In still other embodiments, the light source 40 includes at least one vertical cavity surface-emitting laser (VCSEL) diode. Other light sources 40 compatible with embodiments described herein include, but are not limited to, light-emitting diodes (LEDs) and filtered lamps.

In certain embodiments, each wavelength is selected so as to work (e.g., cooperate functionally) with one or more chromophores within the target tissue. In several embodiments, irradiation of chromophores increases the production of ATP in the target tissue and/or controls, inhibits, prevents, minimizes, or reduces apoptosis of the injured tissues, thereby producing beneficial effects, as described more fully below.

Some chromophores, such as water or hemoglobin, are ubiquitous and absorb light to such a degree that little or no penetration of light energy into a tissue occurs. For example, water absorbs light above approximately 1300 nanometers. Thus energy in this range has little ability to penetrate tissue due to the water content. However, water is transparent or nearly transparent in wavelengths between 300 and 1300 nanometers. Another example is hemoglobin, which absorbs heavily in the region between 300 and 670 nanometers, but is reasonably transparent above 670 nanometers.

Based on these broad assumptions, one can define an "IR window" into the body. Within the window, there are certain wavelengths that are more or less likely to penetrate. This discussion does not include wavelength dependent scattering effects of intervening tissues.

The absorption/transmittance of various tissues have been directly measured to determine the utility of various wavelengths. For example, blood absorbs less in the region above 700 nanometers, and is particularly transparent at wavelengths above 780 nanometers. Wavelengths below 700 nanometers are heavily absorbed, and are not likely to be useful therapeutically (except for topical indications). However, in certain embodiments, wavelengths below 700 nm are beneficial, for example in treating stem cells prior to delivery to a subject (e.g., as an in vitro pre-treatment).

Absorption by the target tissue can be strong in a range of wavelengths (e.g., between 620 and 980 nanometers) at which copper centers in mitochondria absorb. Thus, absorption in the range of wavelengths is expected upon a photostimulative effect taking place.

By combining the transmittance through intervening tissue with the absorption by target tissue, the efficiency of energy delivery as a function of wavelength can be calculated.

Wavelengths between 780 and 880 nanometers are preferable (efficiency of 0.6 or greater) for certain embodiments described herein. The peak efficiency is about 800 to 830 nanometers (efficiency of 1.0 or greater). These wavelengths are not absorbed by water or hemoglobin, and are likely to penetrate to the long bones. Once these wavelengths reach the long bones, they will be absorbed by the cells within the long bones and converted to useful energy.

Power Density

Phototherapy for the treatment of neurologic conditions (e.g., neurodegenerative diseases such as Parkinson's disease), for the enhancement of stem cell therapy, and/or for improving the viability of stem cells (among other applications), is based in part on the concept that power density (i.e., power per unit area or number of photons per unit area per unit time) and energy density (i.e., energy per unit area or number of photons per unit area) of the light energy applied to tissue appear to be significant factors in determining the relative efficacy of low level phototherapy. Certain embodiments described herein are based at least in part on the concept that, given a selected wavelength of light energy, it is the power density and/or the energy density of the light delivered to tissue (as opposed to the total power or total energy delivered to the tissue) that are important factors in determining the relative efficacy of phototherapy.

The significance of the power density used in phototherapy has ramifications with regard to the devices and methods used in phototherapy of brain tissue, as schematically illustrated by FIGS. 8A and 8B, which show the effects of scattering by intervening tissue. Further information regarding the scattering of light by tissue is provided by V. Tuchin in "Tissue Optics: Light Scattering Methods and Instruments for Medical Diagnosis," SPIE Press (2000), Bellingham, Wash., pp. 3-11, which is incorporated in its entirety by reference herein.

Figure 32B:
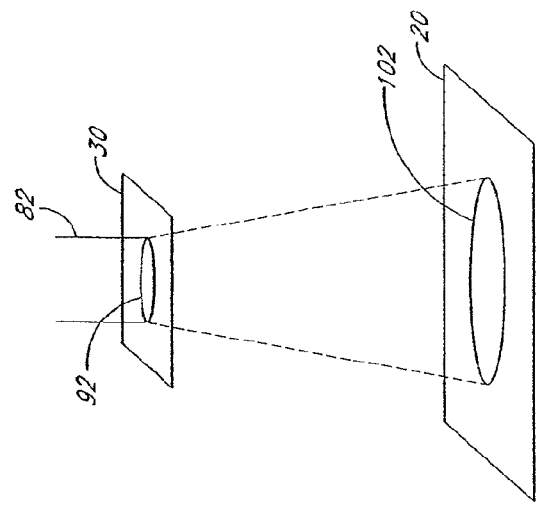
FIGS. 32A and 32B schematically illustrate two light beams having different cross-sections impinging a patient's scalp and propagating through the patient's head to irradiate a portion of the patient's brain tissue.
Figure 32A:
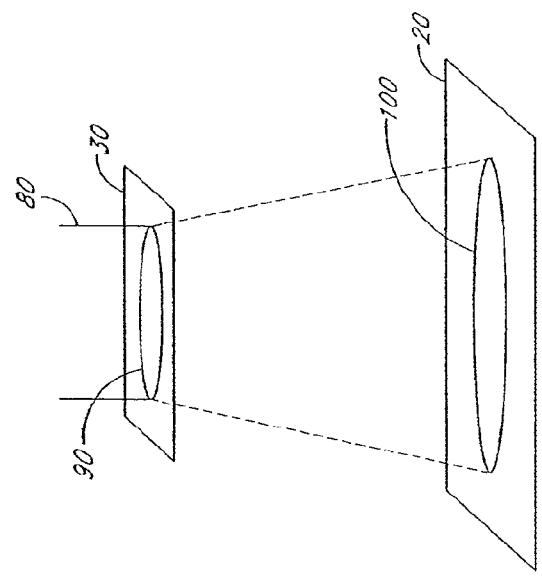

FIG. 32A schematically illustrates a light beam 80 impinging a portion 90 of a patient's scalp 30 and propagating through the patient's head to irradiate a portion 100 of the patient's brain tissue 20. In the example embodiment of FIG. 32A, the light beam 80 impinging the scalp 30 is collimated and has a circular cross-section with a radius of 2 cm and a cross-sectional area of approximately 12.5 cm$^2$. For comparison purposes, FIG. 32B schematically illustrates a light beam 82 having a significantly smaller cross-section impinging a smaller portion 92 of the scalp 30 to irradiate a portion 102 of the brain tissue 20. The light beam 82 impinging the scalp 30 in FIG. 32B is collimated and has a circular cross-section with a radius of 1 cm and a cross-sectional area of approximately 3.1 cm$^2$. The collimations, cross-sections, and radii of the light beams 80, 82 illustrated in FIGS. 32A and 32B are examples; other light beams with other parameters are also compatible with embodiments described herein. In particular, similar considerations apply to focused beams or diverging beams, as they are similarly scattered by the intervening tissue.

As shown in FIGS. 32A and 32B, the cross-sections of the light beams 80, 82 become larger while propagating through the head due to scattering from interactions with tissue of the head. Assuming that the angle of dispersion is 15 degrees and the irradiated brain tissue 20 is 2.5 cm below the scalp 30, the resulting area of the portion 100 of brain tissue 20 irradiated by the light beam 80 in FIG. 32A is approximately 22.4 cm$^2$. Similarly, the resulting area of the portion 102 of brain tissue 20 irradiated by the light beam 82 in FIG. 32B is approximately 8.8 cm$^2$.

Irradiating the portion 100 of the brain tissue 20 with a power density of 10 mW/cm$^2$ corresponds to a total power within the portion 100 of approximately 224 mW (10 mW/cm$^2$×22.4 cm$^2$). Assuming only approximately 5% of the light beam 80 is transmitted between the scalp 30 and the brain tissue 20, the incident light beam 80 at the scalp 30 will have a total power of approximately 4480 mW (224 mW/0.05) and a power density of approximately 358 mW/cm$^2$ (4480 mW/12.5 cm$^2$). Similarly, irradiating the portion 102 of the brain tissue 20 with a power density of 10 mW/cm$^2$ corresponds to a total power within the portion 102 of approximately 88 mW (10 mW/cm$^2$×8.8 cm$^2$), and with the same 5% transmittance, the incident light beam 82 at the scalp 30 will have a total power of approximately 1760 mW (88 mW/0.05) and a power density of approximately 568 mW/cm$^2$ (1760 mW/3.1 cm$^2$). These calculations are summarized in Table 1.

TABLE 1

|  | 2 cm Spot Size (FIG. 32A) | 1 cm Spot Size (FIG. 32B) |
|---|---|---|
| Scalp: | | |
| Area | 12.5 cm$^2$ | 3.1 cm$^2$ |
| Total power | 4480 mW | 1760 mW |
| Power density | 358 mW/cm$^2$ | 568 mW/cm$^2$ |
| Brain: | | |
| Area | 22.4 cm$^2$ | 8.8 cm$^2$ |
| Total power | 224 mW | 88 mW |
| Power density | 10 mW/cm$^2$ | 10 mW/cm$^2$ |

These example calculations illustrate that to obtain a desired power density at the brain 20, higher total power at the scalp 30 can be used in conjunction with a larger spot size at the scalp 30. Thus, by increasing the spot size at the scalp 30, a desired power density at the brain 20 can be achieved with lower power densities at the scalp 30 which can reduce the possibility of overheating the scalp 30. In certain embodiments, the light can be directed through an aperture to define the illumination of the scalp 30 to a selected smaller area. In several embodiments, similar calculations generate light parameters that are used to treat other tissues, such as other neural tissue (e.g., spinal cord or peripheral nerves), cardiac tissue, etc.

In certain embodiments the light energy has a time averaged irradiance or power density at the emission surface of the light source between about 10 mW/cm$^2$ to about 10 W/cm$^2$, between about 100 mW/cm$^2$ to about 1000 mW/cm$^2$, between about 500 mW/cm$^2$ to about 1 W/cm$^2$, or between about 650 mW/cm$^2$ to about 750 mW/cm$^2$ across the cross-sectional area of the light beam. For a pulsed light beam, the time-averaged irradiance is averaged over a time period long compared to the temporal pulse widths of the pulses (e.g., averaged over a fraction of a second longer than the temporal pulse width, over 1 second, or over multiple seconds). For a continuous-wave (CW) light beam with time-varying irradiance, the time-averaged irradiance can be an average of the instantaneous irradiance averaged over a time period longer than a characteristic time period of fluctuations of the light beam. In certain embodiments, a duty cycle in a range between 1% and 80%, between 10% and 30%, or about 20% can be used with a peak irradiance at the emission surface 22 of the output optical assembly 20 between about 12.5 mW/cm$^2$ to about 1000 W/cm$^2$, between about 50 mW/cm$^2$ to about 50 W/cm$^2$, between about 500 mW/cm$^2$ to about 5000 mW/cm$^2$, between about 2500 mW/cm$^2$ to about 5 W/cm$^2$, or between about 3.25 W/cm$^2$ to about 3.75 W/cm$^2$ across the cross-sectional area of the light beam. In certain embodiments, the pulsed light beam has an energy or fluence (e.g., peak irradiance multiplied by the temporal pulsewidth) at the emission surface of the light source between about 12.5 μJ/cm$^2$ to about 1 J/cm$^2$, between about 50 μJ/cm$^2$ to about 50 mJ/cm$^2$, between about 500 μJ/cm$^2$ to about 5 mJ/cm$^2$, between about 2.5 mJ/cm$^2$ to about 5 mJ/cm$^2$, or between about 3.25 mJ/cm$^2$ to about 3.75 mJ/cm$^2$.

The cross-sectional area of the light beam of certain embodiments (e.g., multimode beams) can be approximated using an approximation of the beam intensity distribution. For example, measurements of the beam intensity distribution can be approximated by a Gaussian ($1/e^2$ measurements) or by a "top hat" distribution and a selected perimeter of the beam intensity distribution can be used to define a bound of the area of the light beam. In certain embodiments, the irradiance at the emission surface of the light source is selected to provide the desired irradiances at the subdermal target tissue. The irradiance of the light beam is preferably controllably variable so that the emitted light energy can be adjusted to provide a selected irradiance at the subdermal tissue being irradiated. In certain embodiments, the light beam emitted from the emission surface of the light source is continuous with a total radiant power in a range of about 4 Watts to about 6 Watts. In certain embodiments, the radiant power of the light beam is 5 Watts±20% (CW). In certain embodiments, the peak power for pulsed light is in a range of about 10 Watts to about 30 Watts (e.g., 20 Watts). In certain embodiments, the peak power for pulsed light multiplied by the duty cycle of the pulsed light yields an average radiant power in a range of about 4 Watts to about 6 Watts (e.g., 5 Watts).

In certain embodiments, the light source 40 is capable of emitting light energy at a power sufficient to achieve a predetermined power density at the subdermal target tissue (e.g., at a depth of approximately 2 centimeters from the dura, at the depth of the marrow cavity of the irradiated long bones; at the myocardium, etc.). It is presently believed that phototherapy of tissue is most effective when irradiating the target tissue with power densities of light of at least about 0.01 mW/cm$^2$ and up to about 1 W/cm$^2$ at the level of the tissue. In various embodiments, the subsurface power density is at least about 0.01, 0.05, 0.1, 0.5, 1, 5, 10, 15, 20, 30, 40, 50, 60, 70, 80, or 90 mW/cm$^2$, respectively, depending on the desired clinical performance. In certain embodiments, the subsurface power density at the target tissue is about 0.01 mW/cm$^2$ to about 100 mW/cm$^2$, about 0.01 mW/cm$^2$ to about 50 mW/cm$^2$, about 2 mW/cm$^2$ to about 20 mW/cm$^2$, or about 5 mW/cm$^2$ to about 25 mW/cm$^2$. It is believed that these subsurface power densities are especially effective at producing the desired biostimulative effects on the tissue being treated. In certain embodiments, a duty cycle in a range between 1% and 80%, between 10% and 30%, or about 20% can be used with a peak irradiance at the target tissue of 0.05 mW/cm$^2$ to about 500 mW/cm$^2$, about 0.05 mW/cm$^2$ to about 250 mW/cm$^2$, about 10 mW/cm$^2$ to about 100 mW/cm$^2$, or about 25 mW/cm$^2$ to about 125 mW/cm$^2$.

In certain embodiments, the irradiance of the light beam is selected to provide a predetermined irradiance at the subdermal target tissue (e.g., the brain, the myocardium, the marrow cavity of the irradiated long bones). The selection of the appropriate irradiance of the light beam emitted from the emission surface of the light source to use to achieve a desired subdermal irradiance preferably includes consideration of scattering by intervening tissue. Further information regarding the scattering of light by tissue is provided by U.S. Pat. No. 7,303,578, which is incorporated in its entirety by reference herein, and V. Tuchin in "Tissue Optics: Light Scattering Methods and Instruments for Medical Diagnosis," SPIE Press (2000), Bellingham, Wash., pp. 3-11, which is incorporated in its entirety by reference herein.

Taking into account the attenuation of energy as it propagates from the skin surface, through body tissue, bone, and fluids, to the subdermal target tissue, surface power densities preferably between about 10 mW/cm$^2$ to about 10 W/cm$^2$, or more preferably between about 100 mW/cm$^2$ to about 500 mW/cm$^2$, will typically be used to attain the selected power densities at the subdermal target tissue. To achieve such surface power densities, the light source 40 is preferably capable of emitting light energy having a total power output of at least about 25 mW to about 100 W. In various embodiments, the total power output is limited to be no more than about 30, 50, 75, 100, 150, 200, 250, 300, 400, or 500 mW, respectively. In certain embodiments, the light source 40 comprises a plurality of sources used in combination to provide the total power output. The actual power output of the light source 40 is preferably controllably variable. In this way, the power of the light energy emitted can be adjusted in accordance with a selected power density at the subdermal tissue being treated.

Certain embodiments utilize a light source 40 that includes only a single laser diode that is capable of providing about 25 mW to about 100 W of total power output at the skin surface. In certain such embodiments, the laser diode can be optically coupled to the scalp 30 via an optical fiber or can be configured to provide a sufficiently large spot size to avoid power densities which would burn or otherwise damage the scalp 30. In other embodiments, the light source 40 utilizes a plurality of sources (e.g., laser diodes) arranged in a grid or array that together are capable of providing at least about 25 mW to about 100 W of total power output at the skin surface. The light source 40 of other embodiments may also comprise sources having power capacities outside of these limits.

Temporal Pulsewidth, Temporal Pulseshape, Duty Cycle, Repetition Rate, and Irradiance Per Pulse In some embodiments, a pulsed light beam is used having a temporal profile comprising a plurality of pulses ($P_1$, $P_2$, ..., $P_i$), each pulse having a temporal pulsewidth during which the instantaneous intensity or irradiance I(t) of the pulse is substantially non-zero. For example, a pulse $P_1$ has a temporal pulsewidth from time t=0 to time t=$T_1$, pulse $P_2$ has a temporal pulsewidth from time t=$T_2$ to time t=$T_3$, and pulse $P_i$ has a temporal pulsewidth from time t=$T_i$ to time t=$T_{i+1}$. The temporal pulsewidth can also be referred to as the "pulse ON time." The pulses are temporally spaced from one another by periods of time during which the intensity or irradiance of the beam is substantially zero. For example, pulse $P_1$ is spaced in time from pulse $P_2$ by a time t=$T_2$-$T_1$. The time between pulses can also be referred to as the "pulse OFF time." In certain embodiments, the pulse ON times of the pulses are substantially equal to one another, while in certain other embodiments, the pulse ON times differ from one another. In certain embodiments, the pulse OFF times between the pulses are substantially equal to one another, while in certain other embodiments, the pulse OFF times between the pulses differ from one another. As used herein, the term "duty cycle" has its broadest reasonable interpretation, including but not limited to, the pulse ON time divided by the sum of the pulse ON time and the pulse OFF time. For a pulsed light beam, the duty cycle is less than one. The values of the duty cycle and the temporal pulsewidth fully define the repetition rate of the pulsed light beam. Further disclosure regarding parameters of pulsed light compatible with certain embodiments described herein may be found in United States Patent Publication No. 2009/0254154, which is incorporated in its entirety by reference herein.

Each of the pulses can have a temporal pulseshape which describes the instantaneous intensity or irradiance of the pulse I(t) as a function of time. For example, the temporal pulseshapes of the pulsed light beam may be irregular, and need not be the same among the various pulses. In certain embodiments, the temporal pulseshapes of the pulsed light beam are substantially the same among the various pulses. For example, the pulses can have a square temporal pulseshape, with each pulse having a substantially constant instantaneous irradiance over the pulse ON time. In certain embodiments, the peak irradiances of the pulses differ from one another, while in certain other embodiments, the peak irradiances of the pulses are substantially equal to one another (see, e.g., FIGS. 21 A and B, and 21 C and D, respectively, of United States Patent Publication No. 2009/0254154, each of which is incorporated in its entirety by reference herein). Various other temporal pulseshapes (e.g., triangular, trapezoidal) are also compatible with certain embodiments described herein. For example, FIG. 21C of U.S. patent application Ser. No. 12/403,824, filed Mar. 13, 2009, which is incorporated in its entirety by reference herein, schematically illustrates a plurality of trapezoidal pulses in which each pulse has a rise time (e.g., corresponding to the time between an instantaneous irradiance of zero and a peak irradiance of the pulse) and a fall time (e.g., corresponding to the time between the peak irradiance of the pulse and an instantaneous irradiance of zero). In certain embodiments, the rise time and the fall time can be expressed relative to a specified fraction of the peak irradiance of the pulse (e.g., time to rise/fall to 50% of the peak irradiance of the pulse).

As used herein, the term "peak irradiance" of a pulse $P_i$ has its broadest reasonable interpretation, including but not limited to, the maximum value of the instantaneous irradiance $I(t)$ during the temporal pulsewidth of the pulse. In certain embodiments, the instantaneous irradiance is changing during the temporal pulsewidth of the pulse while in certain other embodiments, the instantaneous irradiance is substantially constant during the temporal pulsewidth of the pulse.

As used herein, the term "pulse irradiance" $I_{P_i}$ of a pulse $P_i$ has its broadest reasonable interpretation, including but not limited to, the integral of the instantaneous irradiance $I(t)$ of the pulse $P_i$ over the temporal pulsewidth of the pulse:

$$I_{P_i} = \int_{T_i}^{T_{i+1}} I(t) \cdot dt / (T_{i+1} - T_i).$$

As used herein, the term "total irradiance" $I_{TOTAL}$ has its broadest reasonable interpretation, including but not limited to, the sum of the pulse irradiances of the pulses:

$$I_{TOTAL} = \sum_{i=0}^{N} I_{P_i}.$$

As used herein, the term "time-averaged irradiance" $I_{AVE}$ has its broadest reasonable interpretation, including but not limited to, the integral of the instantaneous irradiance $I(t)$ over a period of time T large compared to the temporal pulsewidths of the pulses:

$$I_{AVE} = \int_0^T I(t) \cdot dt / T.$$

The integral $$\int_0^T I(t) \cdot dt$$

provides the energy of the pulsed light beam.

For example, for a plurality of square pulses with different pulse irradiances $I_{P_i}$ and different temporal pulsewidths $\Delta T_i$, the time-averaged irradiance over a time T equals $$I_{AVE} = \frac{1}{T} \sum_i I_{P_i} \cdot \Delta T_i.$$

For another example, for a plurality of square pulses with equal pulse irradiances $I_P$, with equal temporal pulsewidths, and equal pulse OFF times (having a duty cycle D), the time-averaged irradiance equals $I_{AVE} = I_P \cdot D$. For example, as shown in FIG. 21D of U.S. patent application Ser. No. 12/403,824, the time-averaged irradiance (shown as a dashed line) is less than the pulse irradiance of the pulses.

The pulse irradiances and the duty cycle can be selected to provide a predetermined time-averaged irradiance. In certain embodiments in which the time-averaged irradiance is equal to the irradiance of a continuous-wave (CW) light beam, the pulsed light beam and the CW light beam have the same number of photons or flux as one another. For example, a pulsed light beam with a pulse irradiance of 5 mW/cm$^2$ and a duty cycle of 20% provides the same number of photons as a CW light beam having an irradiance of 1 mW/cm$^2$. However, in contrast to a CW light beam, the parameters of the pulsed light beam can be selected to deliver the photons in a manner which achieve results which are not obtainable using CW light beams.

For example, for hair removal, tattoo removal, or wrinkle smoothing, pulsed light beams have previously been used to achieve selective photothermolysis in which a selected portion of the skin is exposed to sufficiently high temperatures to damage the hair follicles (e.g., temperatures greater than 60 degrees Celsius), to ablate the tattoo ink (e.g., temperatures much greater than 60 degrees Celsius), or to shrink the collagen molecules (e.g., temperatures between 60-70 degrees Celsius), respectively, while keeping the other portions of skin at sufficiently low temperatures to avoid unwanted damage or discomfort. The parameters of these pulsed light beams are selected to achieve the desired elevated temperature at the selected portion of the skin by absorption of the light by the selected chromophore while allowing heat to dissipate (characterized by a thermal relaxation time) during the pulse OFF times to keep other areas of skin at lower temperatures. As described by J. Lepselter et al., "Biological and clinical aspects in laser hair removal," J. Dermatological Treatment, Vol. 15, pp. 72-83 (2004), the pulse ON time for hair removal is selected to be between the thermal relaxation time for the epidermis (about 3-10 milliseconds) and the thermal relaxation time for the hair follicle (about 40-100 milliseconds). In this way, the hair follicle can be heated to sufficiently high temperatures to damage the follicle without causing excessive damage to the surrounding skin.

In contrast to these treatments which are based on creating thermal damage to at least a portion of the skin, certain embodiments described herein utilize pulse parameters which do not create thermal damage to at least a portion of the skin. In certain embodiments, one or more of the temporal pulsewidth, temporal pulseshape, duty cycle, repetition rate, and pulse irradiance of the pulsed light beam are selected such that no portion of the skin is heated to a temperature greater than 60 degrees Celsius, greater than 55 degrees Celsius, greater than 50 degrees Celsius, or greater than 45 degrees Celsius. In certain embodiments, one or more of the temporal pulsewidth, temporal pulseshape, duty cycle, repetition rate, and pulse irradiance of the pulsed light beam are selected such that no portion of the skin is heated to a temperature greater than 30 degrees Celsius above its baseline temperature, greater than 20 degrees Celsius above its baseline temperature, or greater than 10 degrees Celsius above its baseline temperature. In certain embodiments, one or more of the temporal pulsewidth, temporal pulseshape, duty cycle, repetition rate, and pulse irradiance of the pulsed light beam are selected such that no portion of the bone marrow is heated to a temperature greater than 5 degrees Celsius above its baseline temperature, greater than 3 degrees Celsius above its baseline temperature, or greater than 1 degree Celsius above its baseline temperature. As used herein, the term "baseline temperature" has its broadest reasonable interpretation, including but not limited to, the temperature at which the tissue would have if it were not irradiated by the light. In contrast to previous low-light level therapies, the pulsed light beam has an average radiant power in the range of about 1 Watt to about 6 Watts including about 1 to about 3 Watts, about 3 to about 4 Watts, or about 4 Watts to about 6 Watts.

In certain embodiments, the pulse parameters are selected to achieve other effects beyond those which are achievable using CW light beams. In certain embodiments described herein, pulsed irradiation may provide a more efficacious mobilization of HSCs, increased proliferation, differentiation, engraftment of stem cells, or improve the overall efficacy of stem cell therapy. The pulsed irradiation can provide higher peak irradiances for shorter times, thereby providing more power to propagate to the target tissue while allowing thermal relaxation of the intervening tissue and blood between pulses to avoid unduly heating the intervening tissue. The time scale for the thermal relaxation is typically in the range of a few milliseconds. For example, the thermal relaxation time constant (e.g., the time for tissue to cool from an elevated temperature to one-half the elevated temperature) of human skin is about 3-10 milliseconds, while the thermal relaxation time constant of human hair follicles is about 40-100 milliseconds. Thus, previous applications of pulsed light to the body for hair removal have optimized temporal pulsewidths of greater than 40 milliseconds with time between pulses of hundreds of milliseconds.

However, while pulsed light of this time scale advantageously reduces the heating of intervening tissue and blood, it does not provide an optimum amount of efficaciousness as compared to other time scales. In certain embodiments described herein, one or more of the patient's long bones are irradiated with pulsed light having parameters which are not optimized to reduce thermal effects, but instead are optimized to stimulate, to excite, to induce, or to otherwise support one or more intercellular or intracellular biological processes which are involved in the mobilization and proliferation of HSCs from the bone marrow cavity. Thus, in certain such embodiments, the selected temporal profile can result in temperatures of the irradiated tissue which are higher than those resulting from other temporal profiles, but which are more efficacious than these other temporal profiles. In certain embodiments, the pulsing parameters are selected to utilize the kinetics of the biological processes rather than optimizing the thermal relaxation of the tissue. In certain embodiments, the pulsed light beam has a temporal profile (e.g., peak irradiance per pulse, a temporal pulse width, and a pulse duty cycle) selected to modulate membrane potentials in order to enhance, restore, or promote cell survival, cell function, or both of the irradiated target cells. For example, in certain embodiments, the pulsed light has a temporal profile which enhances the proliferation of HSCs but does not optimize the thermal relaxation of the irradiated tissue.

In certain embodiments, the temporal profile (e.g., peak irradiance, temporal pulse width, and duty cycle) are selected to enhance the proliferation and mobilization of HSCs from the bone marrow while maintaining the irradiated portion of the long bones at or below a predetermined temperature. This predetermined temperature is higher than the optimized temperature which could be achieved for other temporal profiles (e.g., other values of the peak irradiance, temporal pulse width, and duty cycle) which are optimized to minimize the temperature increase of surrounding tissue due to the irradiation. For example, a temporal profile having a peak irradiance of 10 W/cm$^2$ and a duty cycle of 20% has a time-averaged irradiance of 2 W/cm$^2$. Such a pulsed light beam provides the same number of photons to the irradiated surface as does a continuous-wave (CW) light beam with an irradiance of 2 W/cm$^2$. However, because of the "dark time" between pulses, the pulsed light beam can result in a lower temperature increase than does the CW light beam. To minimize the temperature increase of the irradiated portion of the long bones, the temporal pulse width and the duty cycle can be selected to allow a significant portion of the heat generated per pulse to dissipate before the next pulse reaches the irradiated portion. In certain embodiments described herein, rather than optimizing the beam temporal parameters to minimize the temperature increase, the temporal parameters are selected to effectively correspond to or to be sufficiently close to the timing of the biomolecular processes involved in the absorption of the photons to provide an increased efficacy. Rather than having a temporal pulse width on the order of hundreds of microseconds, certain embodiments described herein utilize a temporal pulse width which does not optimize the thermal relaxation of the irradiated tissue (e.g., milliseconds, tens of milliseconds, hundreds of milliseconds). Since these pulse widths are significantly longer than the thermal relaxation time scale, the resulting temperature increases are larger than those of smaller pulse widths, but still less than that of CW light beams due to the heat dissipation the time between the pulses.

Beam Size and Beam Profile

In certain embodiments, the light beam will be manipulated (e.g. with non-transmissive materials) to yield a rectangular, oval, or other geometric shape in the approximate length and width of the particular long bone to be irradiated. In certain embodiments, multiple light sources can be used to irradiate a single long bone.

In certain embodiments, the light beam has a nominal diameter in a range of about 10 millimeters to about 40 millimeters, in a range of about 20 millimeters to about 35 millimeters, less than 33 millimeters, or equal to about 30 millimeters. In certain embodiments, the cross-sectional area is generally circular with a radius in a range of about 1 centimeter to about 2 centimeters. In certain embodiments, the light beam irradiating the skin has a cross-sectional area greater than about 2 cm$^2$ or in a range of about 2 cm$^2$ to about 20 cm$^2$ (e.g., at an emission surface of an optical element generating the light beam).

As used herein, the beam diameter is defined to be the largest chord of the perimeter of the area of the skin irradiated by the light beam at an intensity of at least 1/e$^2$ of the maximum intensity of the light beam. The perimeter of the light beam used to determine the diameter of the beam is defined in certain embodiments to be those points at which the intensity of the light beam is 1/e$^2$ of the maximum intensity of the light beam. The maximum-useful diameter of certain embodiments is limited by the size of the patient's long bones and by the heating of the patient's body by the irradiation. The minimum-useful diameter of certain embodiments is limited by heating and by the total number of treatment sites that could be practically implemented. For example, to cover a large area of one of the patient's long bones with a beam having a small beam diameter would correspondingly use a large number of treatment sites. In certain embodiments, the time of irradiation per treatment site can be adjusted accordingly to achieve a desired exposure dose.

Specifying the total flux inside a circular aperture with a specified radius centered on the exit aperture ("encircled energy") is a method of specifying the power (irradiance) distribution over the light beam emitted from the emission surface of a light source. The "encircled energy" can be used to ensure that the light beam is not too concentrated, too large, or too small. In certain embodiments, the light beam emitted from the emission surface has a total radiant power, and the light beam has a total flux inside a 20-millimeter diameter cross-sectional circle centered on the light beam at the emission surface which is no more than 75% of the total radiant power. In certain such embodiments, the light beam has a total flux inside a 26-millimeter diameter cross-sectional circle centered on the light beam at the emission surface 22 which is no less than 50% of the total radiant power.

In certain embodiments, the beam intensity profile has a semi-Gaussian profile, while in certain other embodiments, the beam intensity profile has a "top hat" profile. In certain embodiments, the light beam is substantially without high flux regions or "hot spots" in the beam intensity profile in which the local flux, averaged over a 3 millimeter by 3 millimeter area, is more than 10% larger than the average flux. Certain embodiments employ a light beam substantially without hot spots, thereby avoiding large temperature gradients at the patient's skin which would otherwise cause discomfort to the patient.

Divergence

In certain embodiments, the beam divergence emitted from the emission surface of the light source is significantly less than the scattering angle of light inside the body tissue being irradiated, which is typically several degrees. In certain embodiments, the light beam has a divergence angle greater than zero and less than 35 degrees.

Targets of Cell Therapy

As discussed above, cell therapy can be used to treat a wide variety of disorders. For example, Parkinson's disease is a chronic, progressive neurodegenerative disease or movement disorder that affects up to one million people in the United States. Parkinson's disease affects neurologic function by degrading motor skills of the subject and by causing dementia. The pathology of Parkinson's disease includes reduced formation and action of dopamine, which is produced in the dopaminergic neurons of the brain. Previous research of the causes and possible treatments of Parkinson's disease have been directed towards efforts to compensate for the reduced formation and action of dopamine caused by the disease.

Dementia (e.g., as resulting from Parkinson's disease) is a collection of symptoms but is not generally considered a disease itself. Dementia is characterized as the loss of cognitive function having a severity so as to interfere with a person's daily activities. Cognitive function includes activities such as knowing, thinking, learning, memory, perception, and judging. Symptoms of dementia can also include changes in personality, mood, and behavior of the subject. Although, in some cases, dementia can be treated by treating or curing the underlying disease (e.g. infection, nutritional deficiency, tumor), in most cases dementia is considered incurable.

Dementia tends to develop mostly in elderly people. It has been estimated that 5-8% of all people over the age of 65 have some form of dementia, and with that figure doubling every five years above that age. It is estimated that as many as half of people in their 80's suffer from some form of dementia. One of the most common causes of dementia is an underlying neurological disorder, such as Alzheimer's disease. Alzheimer's disease affects about 4 million Americans and appears to be increasing in frequency, as is the resulting dementia. Other non-limiting examples of causes of dementia include AIDS or HIV infection, Creutzfeldt-Jakob disease, head trauma (including single-event trauma and long term trauma such as multiple concussions or other traumas which may result from athletic injury), Lewy body disease, Pick's disease, Parkinson's disease, Huntington's disease, drug or alcohol abuse, brain tumors, hydrocephalus, and kidney or liver disease.

Furthermore, people suffering from mental diseases or disorders can suffer from varying levels of diminishment of cognitive function that do not rise to the level of dementia. Additionally, generally healthy individuals may also perceive some loss of cognitive function, most commonly a reduction in the function of memory. Loss or diminishment of memory may occur in any of the four commonly designated phases of memory, namely learning, retention, recall and recognition, and may be related to immediate memory, recent memory or remote memory. Loss of motor function may occur as a result of any of a number of causes, including many of those discussed above for which there is also a loss of cognitive function.

Alzheimer's disease is another neurological disorder that affects numerous individuals around the world. Replacement of diseased neurons through cell therapy may help slow or compensate for the loss of function Alzheimer's patients' experience.

Apart from degenerative disorders, acute injury to neural tissue may lead to loss of neural function. For example, traumatic brain injury can yield cell damage or death by both primary and secondary mechanisms (discussed further below). Head injury in general, whether from a direct impact to the head or from swelling of the brain due to indirect impact, can also reduce the function of neurons. Additionally, spinal cord injury is one of the most publicly recognized forms of acute injury to neural tissue. Cell therapy in this area of neurological disorder is aimed at restoration (complete or partial) function to organs or limbs that have lost function due to an injury. Even modest clinical improvements have the potential to yield great effects in terms of restoration of the activities an individual can perform as well as their quality of life.

In addition to neurological disorders and injury, in several embodiments, cell therapy plays a major role in treating cardiac damage. Myocardial infarctions and strokes often result in substantial loss of function in portions of the myocardium. Generally, the myocardium is viewed as comprising a terminally differentiated group of cells with limited capacity for self-renewal. Thus, cell therapy to treat cardiac tissue damage represents great potential progress in helping post-infarction or post-stroke patients regain functionality.

Many other diseases that affect various tissues are key targets for cell therapy. In several embodiments, liver damage or cancer is treated with cell therapy in order to replace lost or malfunctioning cells. In several embodiments, diabetic patients are treated with pancreatic progenitor cells (or other stem cells differentiated to pancreatic identity) in order to recapitulate loss of insulin secretion.

As discussed above, cancers are a particularly interesting area from the perspective of cell therapies, in that the standard therapeutic regime for treating the disease, induces damage to host tissues. In the end, the goal is to kill the cancerous cells, and not so many of the host cells that the patient dies. As such, combating these treatment-induced side effects with cell therapy may increase the probability of survival of cancer patients.

As discussed more fully below, the use of LLLT in combination with cell therapy enhances the efficacy of the cell therapy and leads to a more pronounced therapeutic effect. Moreover, LLLT, in several embodiments, positively impacts stem cells in a fashion which makes them more suitable for use in cell therapy. Additionally, LLLT, in several embodiments, not only enhances the effects of exogenously administered stem cells used in cell therapy, it also positively affects endogenous stem cells (e.g., resident neural progenitors or resident cardiac progenitors) such that the combination of administered cell and endogenous cells yields a synergistically enhanced therapeutic effect.

Embryonic stem cells, which are typically derived from an early stage embryo, have the potential to develop into any type of cell in the body. In contrast, adult stem cells generally develop into cell types related to the tissue from which the stem cells were isolated.

Use of embryonic stem cells in a clinical setting is often problematic because embryonic stem cells are typically allogeneic to a patient, as the embryonic stem cells rarely originate from that patient. As a result, rejection of transplanted embryonic stem cells may be a significant concern. Likewise, the pluripotency of embryonic stem cells does not guarantee differentiation into cells related to the target tissue. As discussed further below, in some embodiments, mesenchymal stem cells are used in order to limit the adverse immunological response to transplanted cells. In contrast, adult stem cells taken from the patient and subsequently reintroduced into the same patient will generally not be rejected. Further, because adult stem cells generally develop into related cell types, the risk that the adult stem cells will develop into undesired cell types may be reduced by taking adult stem cells from the tissue that is to be treated or repaired. Therefore, in some embodiments, non-embryonic stem cells are used (e.g., adult stem cells). In certain embodiments, use of autologous adult stem cells is preferred in order to significantly minimize the risk of immune rejection of transplanted cells. However, in several embodiments, embryonic stem cells are employed.

LLLT and Stem Cell Mobilizing Compounds to Increase Stem Cell Production

In several embodiments, a method for increasing the number of one or more particular cell types in a patient, such as in a patient's bloodstream is disclosed. The cell types can include, for example, white blood cells (e.g., a neutrophil, macrophage, natural killer cell, basophil, eosinophil, B cell, CD4 T-cell, or CD8 T-cell) platelets, or red blood cells. In some embodiments, an increased quantity of cells, such as stem cells (e.g., HSC) are mobilized into the peripheral bloodstream of a patient for collection for a diagnostic purpose, such as screening for a hematologic or oncologic disease, a therapeutic purpose, such as autologous or heterologous blood or blood component donation, or to stimulate the bone marrow prior to transplantation, or a storage purpose, such as cell banking.

In some embodiments, a combination of a therapeutically-effective amount of one, two, or more agents that can stimulate mobilization into the peripheral bloodstream, production and/or improve function of one, two, or more cell types is administered. The agent(s) could be given through any desired route of administration, including orally, rectally, intravenously, intramuscularly, subcutaneously, or an aerosol. Some non-limiting embodiments of an agent that can stimulate mobilization into the peripheral bloodstream, production of and/or improve function of a cell type include IL-1, IL-2, IL-3, IL-6, GM-CSF, G-CSF, plerixafor, PDGF, TGF-beta, NGF, IGFs, growth hormone, erythropoietin, thrombopoietin, and the like. In addition to naturally occurring growth factors, growth factor analogs and growth factor derivatives such as fusion proteins can be used as well. In some embodiments, the method involves administration of a therapeutically-effective amount of G-CSF and a therapeutically-effective amount of electromagnetic radiation. In some embodiments, the method comprises administering a combination of a therapeutically-effective amount of plerixafor and a therapeutically-effective amount of electromagnetic radiation. In some embodiments, a therapeutically-effective amount of electromagnetic radiation is combined with another agent that, in some embodiments, could be a hematopoietic stem cell mobilizer. In some embodiments, a therapeutically-effective amount of electromagnetic radiation is combined with combinations of two or more of G-CSF, GM-CSF, plerixafor, IL-1, IL-2, IL-3, IL-6, PDGF, TGF-beta, NGF, IGFs, growth hormone, erythropoietin, thrombopoietin or another agent.

In some embodiments, the G-CSF and electromagnetic radiation are used to prevent or treat neutropenia. In still other embodiments, the therapeutic agent and electromagnetic radiation are used to prevent or treat anemia or thrombocytopenia.

In some embodiments, at least a portion of the electromagnetic radiation is administered after the administration of the agent, such as G-CSF. In other embodiments, at least a portion of the electromagnetic radiation is administered prior to the agent, such as G-CSF. In still other embodiments, at least a portion of the agent, such as G-CSF and at least a portion of the electromagnetic radiation are administered concurrently. In some embodiments, the dose of G-CSF administered can be between about 1-200 micrograms/kg, such as between about 1-200 micrograms/kg, 1-10 micrograms/kg, or 5-10 micrograms/kg intravenously (IV) or subcutaneously (SQ) every other day, every day, twice daily, or another dosing frequency depending on the desired clinical result. In some embodiments, 1, 2, 3, 4, 5, 6, 7, 8, 9, 10, or more doses of either the G-CSF, electromagnetic radiation, or both are administered to the patient until the patient's absolute neutrophil count increases to greater than $500/mm^3$, $750/mm^3$, $1000/mm^3$, $1250/mm^3$, $1500/mm^3$, or more.

In some embodiments, at least a portion of the electromagnetic radiation is delivered to one, two, or more bones including the long bones of the body. The long bones of the body are those that are typically longer than they are wide. Such bones include, but are not limited to the femur, tibia, fibula, humerus, radius, ulna, metacarpals, and metatarsals. Other non-limiting examples of bones to deliver the electromagnetic radiation to could include the anterior or posterior iliac crest, ischial tuberosity, ribs, sternum, or cervical, thoracic, lumbar, or sacral vertebrae.

In several embodiments, the time-averaged irradiance at the HSCs receiving light (e.g., the marrow cavity of the irradiated long bones) is greater than $0.01\ mW/cm^2$.

In several embodiments, the biostimulatory effect of phototherapy will enhance the effects of a particular agent such as G-CSF, plerixafor, or another HSC mobilizer, on proliferation of a cell such as a HSC and/or production of neutrophils. Further examples of the biostimulatory effect of phototherapy are disclosed in U.S. Patent Application Publication No. 2008/0221211, now abandoned, which describes the treatment of neurological injury or cancer by administration of dichloroacetic acid and/or electromagnetic radiation, and which is incorporated in its entirety by reference herein. The efficacy of such a combination approach would be of great value to the medical field because HSCs could be collected peripherally. Based on the current skill and knowledge in the art, the synergistic effect of the combination of an agent such as those disclosed herein, e.g., a hematopoietic stem cell mobilizer and biostimulation via phototherapy would also be unexpected, and would otherwise be thought to be contraindicated in some cancer or neutropenic patients (the target patient population), as light therapy/electromagnetic radiation has been shown to induce proliferation of cancer cells.

LLLT Effects on Stem Cells

The LLLT devices, parameters, and procedures disclosed herein, in several embodiments, are used to enhance the efficacy of cell therapy. As discussed above, cell therapy is a growing field of medicine and in combination with the enhancing effects of LLLT, is an important addition to the selection of therapies to combat disease and injury that cause cell death and/or loss of function. The term "progenitor cell" as used herein has its broadest reasonable meaning, including but not limited to (1) a pluripotent, or lineage-uncommitted, progenitor cell, a "stem cell" or "mesenchymal stem cell" (MSC), that is potentially capable of an unlimited number of mitotic divisions to either renew its line or to produce progeny cells that will differentiate into any of a variety of cells (e.g., cells of the central nervous system including neural cells such as astrocytes, oligodendrocytes, and neurons; cardiac cells; hematopoietic cells, etc.); or (2) a lineage-committed progenitor cell produced from the mitotic division of a stem cell which will eventually differentiate into a neural cell (or other cell type within the lineage of the stem cell, e.g., a cardiac progenitor cell differentiating into a cardiomyocyte). Unlike the stem cell from which it is derived, the lineage-committed progenitor is generally considered to be incapable of an unlimited number of mitotic divisions and will eventually differentiate into a cell type within its lineage (e.g., neural to neural, cardiac to cardiac, etc.). Progenitor cells also encompass the endogenous stores of cells within the body that, in some embodiments are positively affected by LLLT. For example, the resident bone marrow cells are, in some embodiments, induced to proliferate and/or differentiate in response to LLLT administration. As described more fully above, in several embodiments, this response is advantageously used to boost the production of hematopoietic stem cells from the bone marrow to combat various leukemias or as a prophylactic measure prior to other cancer therapies.

The selection of progenitor cell type is, in several embodiments, driven by the characteristics of the disease to be treated and the patient to be treated. For example, certain cell types, such as bone marrow derived stem cells are fairly easily isolated from a patient and readministered to the same patient (e.g., autologous transplant to a cancer patient post-therapy). As discussed above, LLLT is used, in some embodiments, to increase the mobilization of bone marrow derived stem cells, thereby increasing the efficiency of peripheral blood collection of stem cells. While in some embodiments, bone marrow derived stem cells are administered in an allogeneic transplant, certain cell types may present additional benefits for such transplants. For example, mesenchymal cells, in several embodiments, are preferred due to their immune modulating function, which is advantageous in an allogeneic transplant setting.

Mesenchymal stem cells are typically isolated from bone marrow or adipose tissue, and, in several embodiments, suppress immune responses. In several embodiments, MSCs inhibit host T cell responses to a "non-self" marker (such as an allogeneic cell). In several embodiments, host antigen presenting cell (APC) function is altered by MSCs. In some embodiments, monocyte function is reduced by MSCs, through MSC-derived inhibition of on monocyte maturation. In several embodiments, these effects of MSCs are manifest as decreased inflammation post-transplant. In some embodiments, the administration of MSCs assists in lowering inflammation due to disease or injury, in addition to reducing subsequent inflammation due to the transplant of the cells themselves. In several embodiments, MSCs additionally function in an anti-fibrotic manner, which reduces fibrosis (and associated loss of function) in the target tissue. In some embodiments, the release of trophic/paracrine factors (as discussed below) mediates such functions. Thus, the immunomodulatory effects of MSCs are particularly advantageous in embodiments involving allogeneic cell therapy, as the MSCs assist in combating and/or reducing graft versus host immune responses which lower the efficacy of cell therapy.

As used herein, the term "viability" shall be given its ordinary meaning and shall also refer to the ability of a cell, be it a stem cell or a resident cell, to survive disease, trauma, or other injury that would compromise the normal functionality of the cell. In some embodiments, viability is measured by assessing the size of a certain population of cells, while in some embodiments, specific chemical, biological, or analytical tests are performed to evaluate the viability of the cells. Viability is also, in some embodiments, assessed by function, wherein an increase in function may be associated with an increase in viability.

As used herein, the term "proliferation" shall be given its ordinary meaning and shall refer to the process by which one or more stem cells (endogenous or exogenous) divide and increase the population of stem cells (e.g., mitotic division). In several embodiments, proliferation is measured by simple total cell count. In other embodiments, proliferation is assessed by expression of certain proteins (e.g., proliferating cell nuclear antigen, PCNA), or by monitoring entry of cells into the cell cycle.

The term "differentiation" as used herein has its broadest reasonable meaning, including but not limited to the process whereby an unspecialized, pluripotent stem cell proceeds through one or more intermediate stage cellular divisions, ultimately producing one or more specialized cell types. Differentiation thus includes the process whereby precursor cells, e.g., uncommitted cell types that precede the fully differentiated forms but may or may not be true stem cells, proceed through intermediate stage cell divisions to ultimately produce specialized cell types. Differentiation encompasses the process whereby mesenchymal stem cells (MSC) are induced to differentiate into one or more of the committed cell types comprising the central nervous system, in vivo or in vitro.

The term "migration" as used herein shall be given its ordinary meaning and shall also refer to the movement of a stem cell (either endogenous or exogenous) from its initial site (e.g., an endogenous storage site or a site of administration) to a second site (e.g., a final position in a target tissue). In some embodiments, migration occurs based on fluid flow or pressure changes in the environment surrounding the cell. In some embodiments, chemoattractant or chemorepellents induce migration of cells.

As used herein, the term "engraftment" shall be given its ordinary meaning and shall also refer to the process (or result of that process) whereby a cell is incorporated into another group of cells or another tissue. For example, in some embodiments, exogenously administered stem cells engraft (e.g., become a part of) the host myocardium. Engraftment may or may not occur in conjunction with migration, depending on the embodiment. Likewise, engraftment may or may not be associated with increased viability (e.g., engraftment is not a requirement for maintaining or increasing viability of cells), depending on the embodiment.

The terms "growth chamber" and "cell culture chamber" as used herein are used interchangeably and are to be interpreted very broadly to refer to any container or vessel suitable for culturing cells, including, but not limited to, dishes, culture plates (single or multiple well), bioreactors, incubators, and the like. Certain embodiments described herein utilize a cell culture apparatus such as is described in U.S. patent application Ser. No. 10/700,355, filed Nov. 3, 2003 and incorporated by reference herein in its entirety.

Implantation of Irradiated Cells

In several embodiments, LLLT is administered in combination with cell therapy, resulting in enhanced effects of cell therapy. The stem cells may be delivered by numerous routes, including direct injection, catheter-based approaches, intravascular administration, stereotactic-guided delivery, etc. In some embodiments, the enhancement is manifest as an increased viability of the stem cells. In some embodiments, the increased viability is advantageous because the cells are present in a tissue that is afflicted with a disease, and therefore may present one or more cellular pro-death signals. In some embodiments, LLLT enhances viability by increasing the resistance of the cells to apoptotic factors. In some embodiments, anti-apoptotic pathways are upregulated in cells that have received LLLT. While not the only factor to consider, enhanced viability of cells, in some embodiments, is of particular importance, as replacement of damaged or diseased cells may be the most efficacious when the replacement cell is likely to survive.

In some embodiments, LLLT enhances the proliferation of stem cells. In some embodiments, the increase in proliferation results in a substantially larger population of stem cells that can functionally replace (partially or fully) the damaged or diseased cells of the host. For example, administration of a small population of neural progenitor cells to a individual with Parkinson's disease (e.g. by stereotactic delivery of the cells to a target region of the brain) and administration of LLLT, in some embodiments, induces proliferation of the neural progenitor cells to a degree which compensates for the loss of speech or motor control associated with Parkinson's. In some embodiments, LLLT can enhance the proliferation of endogenous stem cells to potentiate the effects of the exogenously delivered stem cells. In some embodiments, the light parameters discussed above are tailored to generate a desired proliferative growth curve (e.g., decreasing frequency and/or intensity of LLLT over time to reduce the proliferative stimulation). In this manner, uncontrolled proliferation of either endogenous or administered stem cells (or other cells receiving LLLT) is avoided.

In several embodiments, LLLT improves the migration of stem cells. In some embodiments, chemoattractant signals present in the target tissue induce the migration of stem cells (endogenous or exogenous) to a desired location. In several embodiments, LLLT potentiates the response of the cells to such a signal, thereby allowing a more rapid repositioning of cells to a desired location. Once in its desired location, in some embodiments, the additional effects of LLLT described herein allow the cell to more rapidly or efficiently provide a therapeutic benefit (e.g., provide function that is lost due to damage or disease). In some embodiments, chemorepellant signals drive cells away from an undesired location. In some embodiments, the combination of chemoattractant and chemorepellant signals work in concert to direct the cells to a desired location. In some embodiments, the chemoattractant and/or chemorepellant signals are exogenously administered as well. In some such embodiments, a series of injections of a chemoattractant compound are pre-delivered to a target tissue in order to generate a gradient of signal for the administered cells to respond to. Post-administration, the cells migrate along this gradient, thereby coming to rest at a desirable position.

In several embodiments, engraftment of the stem cells is improved by administration of LLLT. As discussed above this may be particularly advantageous in certain therapeutic applications, such as for example cell therapy directed to target tissues that experience shear flow, flex, or other forces that may dislodge the cells. For example, in some embodiments, LLLT and cardiac progenitor cells are administered, and engraftment is enhanced (as compared to progenitor cells alone). This is particularly advantageous because the blood flow through the heart could wash the administer cells out of the target organ (for example if the target for the cells was an intracardiac site). Moreover, the constant flex of the myocardium may dislodge the administered cells. As such, the increased engraftment of administered cells increases the efficacy of the therapy due to the retention of a larger number of cells at the target site.

In several embodiments, the function of stem cells is improved by the administration of LLLT. Functional assessment depends on the variety of cell that is administered, e.g., neural function versus cardiac function. Modes of assessing are described in more detail below. In several embodiments, however, the function of administered stem cells (or endogenous stem cells) is improved by light therapy. By way of example, LLLT may promote increase firing of a neuron (derived from a neural progenitor). Similarly, in some embodiments, increased neurotransmitter release results. In some embodiments, alterations in cell biology occur (e.g., increased or decreased axonal transport) which are beneficial to the function of the neuron.

In several embodiments, LLLT positively impacts the administered cells which are themselves enhanced in one or more of the manners described herein. In some embodiments, the effects of the LLLT on the stem cells results in a cascade that yields beneficial effects to the cells of the damaged or diseased host tissue. For example, in some embodiments, the irradiation of stem cells with LLLT induces pro-survival paracrine factor (e.g., growth factors, immunosuppressive molecules) release from the stem cells, which, in turn, improves the survival of the damaged or diseased host tissue. Thus, in some embodiments, the characteristics of the stem cells are enhanced, which improves cell therapy. In some embodiments, the LLLT-treated stem cells become a source of a signal that improves damaged or diseased host tissue (e.g., the cells are a vehicle for a beneficial effect rather than providing the effect directly).

In several embodiments, the stem cells are responsive to the in vivo environment into which they are transplanted.

For example, tissue damage or disease is often associated with various signaling cascades, which, in balance, determine the outcome of a subset of cells (or the entire tissue). In some embodiments, the administered cells detect, and subsequently respond to the milieu of damage, disease, and/or inflammatory signals in the target tissue. In several embodiments (as discussed above), certain characteristics of the administered cells advantageously alter the balance, to the benefit of the survival of the administered cells and/or the cells of the host tissue. For example, the MSCs discussed above, in several embodiments, respond to the pro-inflammatory environment in a damaged tissue by releasing anti-inflammatory cytokines, altering T-cell function, and/or altering monocyte maturation. Thus, MSCs may be of particular benefit in allogeneic transplants. Also, in some embodiments, other progenitor cell types possess similar environmentally-responsive characteristics. Such cells, with the ability to respond to local signals, generate counteractive local and/or paracrine signals, and effectively alter the local environment in a beneficial (e.g., pro-survival or regeneration of function manner) are used in several embodiments. In some embodiments, a combination of these mechanisms results. As discussed, such cells are particularly advantageous in allogeneic transplants, though in some embodiments, they are used in autologous cell transplants.

In certain embodiments, a method is provided for treating damage or illness in the central nervous system in a mammal or human, comprising delivering an effective amount of light energy to an in vitro culture comprising progenitor cells, (e.g. stem cells, induced pluripotent cells, genetically modified adult cells, etc.) and implanting the cells into the central nervous system of a mammal or human, wherein delivering an effective amount of light energy includes delivering light having a wavelength in the visible to near-infrared wavelength range and a power density of at least about 0.01 mW/cm$^2$ to the cells in culture.

In certain embodiments, treatment of a patient comprises implantation of progenitor cells into the central nervous system ("CNS") of the patient. Following implantation, the progenitor cells differentiate to form one or more cell types of the central nervous system. The implanted cells may serve any of a variety of purposes, including replacement of cells or tissues that have been irreparably damaged, repair of a portion of the CNS, enhance the production of important CNS neurochemicals such as dopamine, serotonin, endogenous opioid peptides, and the like. Implantation of progenitor cells may be performed alone, or it may be done in combination with the methods of enhancing neurologic functioning, as described herein. For example, the progenitor cells may be treated with an agent or combination of agents in addition to the laser irradiation, prior to or after implantation. By way of example, the additional agent may be selected from the group consisting of pharmaceutical compounds, cytokines, growth factors, neurotransmitters, hormones, trophic factors, transcription factors, monoclonal antibodies, polyclonal antibodies, venom, or signal transduction molecules. In several embodiments, the agent or combination of agents may have the effect of stimulating or mobilizing progenitor cells.

In several embodiments, treatment of a patient suffering from loss of cardiac function due to an adverse cardiac event comprises implantation of cardiac progenitor cells into the myocardium of the patient (e.g., by catheter-based injection into the myocardial wall). As discussed, herein, the cells may optionally be pre-irradiated, or may be irradiated post-implantation, or combinations thereof. Following implantation, the progenitor cells differentiate to form one or more cardiac cell types. In some embodiments, the cells functionally replace the damaged cardiac cells of the patient, thereby restoring cardiac function (partially or fully). Adverse cardiac events include, but are not limited to, myocardial infarction, ischemic cardiac tissue damage, congestive heart failure, aneurysm, atherosclerosis-induced events, cerebrovascular accident (stroke), and coronary artery disease In certain embodiments, progenitor cells are inoculated and grown in a cell culture in vitro, using parameters including power density as discussed above. Because the light energy is applied directly to the cell culture in vitro and does not travel through intervening body tissue, the power density selected to be delivered to the cell is generally equal to the power density of the light energy as it is emitted from the light apparatus. If lenses, filters, dispersion gratings, or any other material lies between the light source and the cells, any absorption or dispersion of the light energy by such material should be taken into account and the applied light energy adjusted, if needed, to account for the material. In certain embodiments, the treated cells are implanted following treatment. In certain other embodiments, at least some treated cells remain in culture to maintain the cell line for later use.

After in vitro treatment of cells using electromagnetic energy, the cells are transplanted or implanted to a recipient site in a patient. In certain embodiments, the treatment prior to transplantation or implantation includes culturing cells sufficient for implantation. The recipient site may be a site of injury, illness, or defect, or it may be a region of relatively healthy tissue. In certain embodiments, the recipient site and/or the region surrounding such site is treated with light energy according to the methods described supra, before and/or after implantation to enhance the rate at which the implanted cells are integrated with surrounding tissue at the recipient site.

In certain embodiments, progenitor cells such as stem cells are treated with electromagnetic energy as noted above and then implanted into the brain of a patient, such a patient who is at risk for Parkinson's disease, exhibits symptoms of Parkinson's disease, and/or has been diagnosed with Parkinson's disease. As discussed herein, numerous other diseases are treated with combination of appropriate stem cells and LLLT. Following implantation, the recipient site is optionally treated with electromagnetic energy, including directly at the recipient site or through the skull at the recipient site, or some other portion of the brain or other neural tissue, such as the cortex or the spinal cord. In several embodiments, the transplanted cells produce dopamine to treat, or lessen the symptoms and/or delay onset of Parkinson's disease in the patient.

In certain embodiments, progenitor cells are treated with electromagnetic energy and implanted or transplanted at a site of physical trauma to the spinal cord or one or more nerves of a patient. Following implantation, the recipient site is optionally treated with electromagnetic energy. Such optional treatment may include treatment immediately following implantation and/or one or more treatment periods following implantation. The transplanted cells help repair damage to the spinal cord or nerve(s) such that the recovery or prognosis is enhanced in patients having implanted progenitor cells as compared with those who do not receive such implants.

In several embodiments, the progenitor cells are treated with electromagnetic energy after delivery to the target tissue (e.g., in vivo). In some embodiments, this approach improves the overall efficacy of treatment, as there is limited lag time between the exposure of the cells to LLLT and the receipt of beneficial effects by the target tissue. In several embodiments, combinations of LLLT treatment are used. For example, in some embodiments, cells are irradiated both before and after administration. In some embodiments, irradiation occurs one or more times in vitro prior to implantation and/or one or more times after implantation.

Procedures for Light Therapy

In certain embodiments, a patient is treated by identifying a plurality of treatment sites (e.g., at least about 10) on the patient's scalp or other target tissue, administering a plurality of stem cells, directing an electromagnetic radiation source to each of the treatment sites, and propagating electromagnetic radiation from the source to each treatment site. In some embodiments, the stem cells are irradiated prior to administration to a patient. In some embodiments, irradiation of the cells is performed prior to implantation as well as one or more times post-implantation. In certain embodiments, the electromagnetic radiation from the source has a wavelength within a range between about 600 and 1000 nanometers, including about 600 to 630 nm, 630 to 650, nm, 650 to 670 nm, 670 to 700 nm, 700 to 800 nm, 800 to 900 nm, 900 to 1000 nm, and overlapping ranges thereof.

In some embodiments a single treatment site is irradiated. In some embodiments, the treatment site is selected from the group consisting of, heart, lungs, liver, pancreas, kidney, spleen, intestine, bone, bone marrow, teeth/gums, skeletal or smooth muscle, skin, or combinations thereof.

As described more fully below, in certain embodiments, the treatment sites are identified using an apparatus comprising a plurality of optically transmissive elements, each of which corresponds to a treatment site. In certain such embodiments, each of the treatment sites is irradiated by electromagnetic radiation from a source placed in contact with each of the optically transmissive elements. In certain other embodiments, the treatment sites are instead identified by other indicia. For example, each of the treatment sites can be identified by markings made on the scalp, or by structures placed in proximity to the scalp. Each of the treatment sites can then be irradiated. In certain embodiments, each of the treatment sites is irradiated by an electromagnetic radiation source in contact with the scalp or in contact with an intervening optically transmissive element which contacts the scalp. In certain other embodiments, the scalp is not contacted by either the electromagnetic radiation source or an intervening element.

In certain embodiments, each of the treatment sites is irradiated using a single electromagnetic radiation source which is sequentially moved from one treatment site to another. In certain other embodiments, a plurality of sources are used to irradiate multiple treatment sites concurrently. In certain such embodiments, the number of sources is fewer than the number of treatments sites, and the plurality of sources are sequentially moved to sequentially irradiate the treatment sites.

Figure 33:
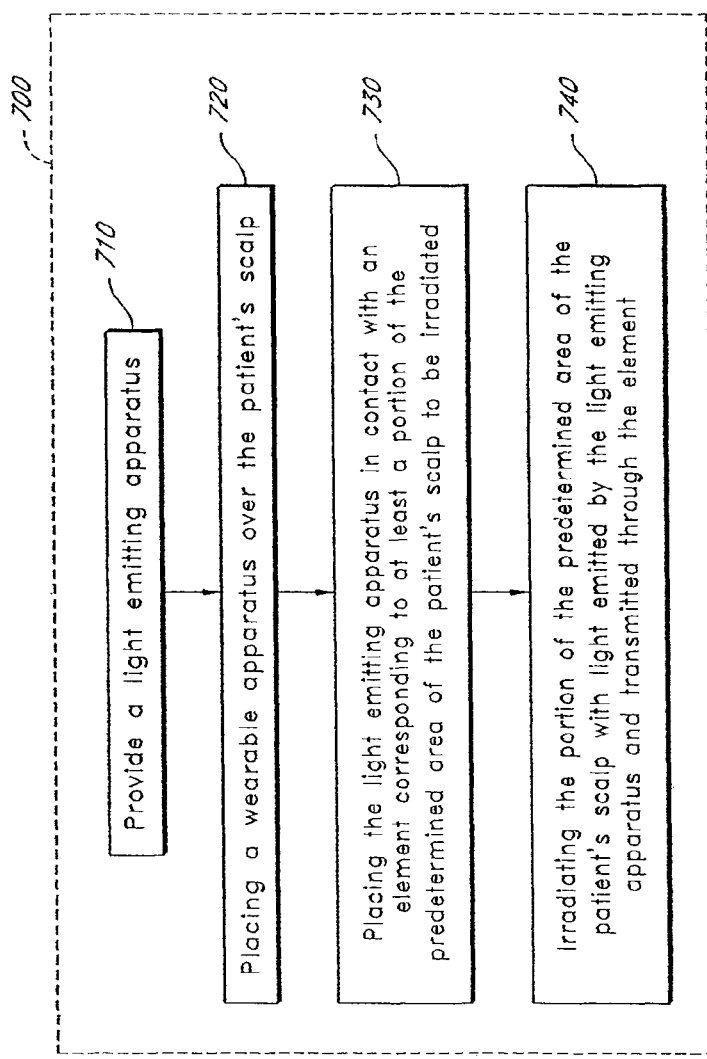
FIG. 33 is a flow diagram of an example method for controllably exposing at least one predetermined area of a patient's scalp to laser light to irradiate the patient's brain.

FIG. 33 is a flow diagram of an example method 700 for controllably exposing at least one predetermined area of a patient's scalp to laser light to irradiate the patient's brain. As discussed above, though not shown in FIG. 33, similar methods are used to treatment of other tissues, in some embodiments. Additionally not shown in FIG. 33 are the optional time points for administering stem cells to a target tissue. As discussed above, cell administration occurs prior to irradiation of the tissue (e.g. before 740). In other embodiments, administration of cells is performed after irradiation of the tissue 740. In still other embodiments, irradiation and/or cell delivery occurs multiple times over a therapeutic regime. As described more fully below, the method 700 is described by referring to the wearable apparatus 500 and the light emitting apparatus 600 described herein. Other configurations of a wearable apparatus 500 and a light emitting apparatus 600 are also compatible with the method 700 in accordance with embodiments described herein.

The method 700 comprises providing a light emitting apparatus 600 in an operational block 710. In certain embodiments, the light emitting apparatus 600 comprises a source 610 of laser light, an optical conduit 620 optically coupled to the source 610, and an optical device 630 optically coupled to the optical conduit 620. Other configurations of the light emitting apparatus 600 besides those in FIGS. 28-34 are also compatible with certain embodiments described herein.

The method 700 further comprises placing a wearable apparatus 500 over the patient's scalp (or other treatment site) in an operational block 720. The apparatus 500 comprises a body 510 and a plurality of elements 520. Each element 520 has a first portion 522 which conforms to a corresponding portion of the patient's scalp when the apparatus 500 is worn by the patient. Each element 520 also has a second portion 524 which conforms to the optical device 630 when the optical device 630 contacts the element 520. Each element 520 is substantially transmissive to laser light emitted by the optical device 630. Other configurations of the wearable apparatuses depicted in the Figures are also compatible with certain embodiments described herein.

The method 700 further comprises placing the light emitting apparatus 600 in contact with an element 520 corresponding to at least a portion of the predetermined area of the patient's scalp (or other treatment site) to be irradiated in an operational block 730. The method 700 further comprises irradiating the portion of the predetermined area of the patient's scalp with light emitted by the light emitting apparatus 600 and transmitted through the element 520 in an operational block 740. As discussed above, depending on the embodiment, the stem cells are optionally delivered prior to irradiating the target tissue. In some embodiments, the stem cells are irradiated after administration to the target tissue.

In certain embodiments, providing the light emitting apparatus 600 in the operational block 710 comprises preparing the light emitting apparatus 600 for use to treat the patient. In certain embodiments, preparing the light emitting apparatus 600 comprises cleaning the portion of the light emitting apparatus 600 through which laser light is outputted. In certain embodiments, preparing the light emitting apparatus 600 comprises verifying a power calibration of laser light outputted from the light emitting apparatus 600. Such verification can comprise measuring the light intensity output from the light emitting apparatus 600 and comparing the measured intensity to an expected intensity level.

In certain embodiments, placing the wearable apparatus 500 over the patient's scalp in the operational block 720 comprises preparing the patient's scalp (or other tissue) for treatment. For example, in certain embodiments, preparing the patient's scalp for treatment comprises removing hair from the predetermined areas of the patient's scalp to be irradiated. Removing the hair (e.g., by shaving) advantageously reduces heating of the patient's scalp by hair which absorbs laser light from the light emitting apparatus 600. In certain embodiments, placing the wearable apparatus 500 over the patient's scalp in the operational block 720 comprises positioning the wearable apparatus 500 so that each element 520 is in contact with a corresponding portion of the patient's scalp.

In certain embodiments, placing the light emitting apparatus 600 in contact with the element 520 in the operational block 730 comprises pressing the light emitting apparatus 600 to the element 520 so that the first portion 522 of the element 520 conforms to the patient's scalp and the second portion 524 of the element 520 conforms to the light emitting apparatus 600. In certain embodiments, by pressing the light emitting apparatus 600 against the element 520 in this way, pressure is applied to the portion of the patient's scalp in contact with the element 520 so as to advantageously blanch the portion of the patient's scalp in contact with the element 520.

In certain embodiments, irradiating the portion of the predetermined area of the patient's scalp (or other tissue) in the operational block 740 comprises triggering the outputting of light from the light emitting apparatus 600 by pressing the light emitting apparatus 600 against the element 520 with a predetermined level of pressure. In certain embodiments, the outputting of light from the light emitting apparatus 600 continues only if a predetermined level of pressure is maintained by pressing the light emitting apparatus 600 against the element 520. In certain embodiments, light is outputted from the light emitting apparatus 600 through the element 520 for a predetermined period of time.

In certain embodiments, the method further comprises irradiating additional portions of the predetermined area of the patient's scalp (or other tissue) during a treatment process. For example, after irradiating a first portion of the predetermined area corresponding to a first element 520, as described above, the light emitting apparatus 600 can be placed in contact with a second element 520 corresponding to a second portion of the predetermined area and irradiating the second portion of the predetermined area with light emitted by the light emitting apparatus 600 and transmitted through the element 520. The various portions of the predetermined area of the patient's scalp can be irradiated sequentially to one another in a predetermined sequence. In certain embodiments, the predetermined sequence is represented by indicia corresponding to the elements 520 of the wearable apparatus 500. In certain such embodiments, the laser emitting apparatus 600 comprises an interlock system which interfaces with the indicia of the wearable apparatus 500 to prevent the various portions of the predetermined area from being irradiated out of the predetermined sequence.

In certain embodiments, a system for treating a patient comprises a support (e.g., a wearable apparatus 500 as described herein) for identifying a plurality of sites on a patient's scalp (or other treatment site) for the application of therapeutic electromagnetic energy in a wavelength range between about 800 nanometers and about 830 nanometers. The system further comprises an instruction for use of the support in combination with an electromagnetic light source (e.g., a light emitting apparatus 600 as described herein) of the therapeutic electromagnetic energy. The instruction for use in certain embodiments comprises instructions compatible with the method 700 described herein.

In certain embodiments, a system for treating a patient comprises an electromagnetic light source (e.g., a light emitting apparatus 600 as described herein) and a plurality of stem cells for administration to a target tissue in the patient. The system further comprises an instruction for use of the electromagnetic radiation source by optically coupling the source to a patient's scalp (or other site) at a plurality of locations to deliver a therapeutic electromagnetic energy to the patient's brain (or other tissue). The instruction for use in certain embodiments comprises instructions compatible with the method 700 described herein.

Certain embodiments utilizing phototherapy as described herein are based at least in part on the finding described above that, for a selected wavelength, the power density (light intensity or power per unit area, in $W/cm^2$) or the energy density (energy per unit area, in $J/cm^2$, or power density multiplied by the exposure time) of the light energy delivered to tissue is an important factor in determining the relative efficacy of the phototherapy, and efficacy is not as directly related to the total power or the total energy delivered to the tissue. In the methods described herein, power density or energy density as delivered to a portion of the patient's brain 20, which can include an area affected by neurodegenerative disease (e.g., Parkinson's disease), appears to be important factors in using phototherapy to treat the brain 20. Certain embodiments apply optimal power densities or energy densities to the intended target tissue, within acceptable margins of error.

As described in U.S. Patent Application Publication Nos. 2004/0138727A1, now U.S. Pat. No. 7,303,578, 2007/0179570A1, and 2007/0179571A1, now U.S. Pat. No. 7,575,589, each of which is incorporated in its entirety by reference herein, LLLT has been is particularly applicable with respect to treating and saving surviving but endangered neurons after stroke (e.g., in a zone of danger surrounding the primary infarct after a stroke or cerebrovascular accident). In some embodiments light energy delivered within a certain range of power densities and energy densities provides the desired biostimulative (or other biological) effect on the intracellular environment, such that proper function is returned to previously nonfunctioning or poorly functioning mitochondria in neurons which are at risk due to stroke. The biological effect may include interactions with chromophores within the target tissue, which facilitate production of ATP thereby feeding energy to injured cells which have experienced decreased blood flow due to the stroke. Because strokes correspond to blockages or other interruptions of blood flow to portions of the brain, effects of increasing blood flow of said blocked vessels by phototherapy, in some embodiments, may be of less importance in the efficacy of phototherapy for stroke victims. In other embodiments, treating vessels with interrupted flow may be beneficial. Further information regarding the role of power density and exposure time is described by Hans H. F. I. van Breugel and P. R. Dop Bär in "Power Density and Exposure Time of He—Ne Laser Irradiation Are More Important Than Total Energy Dose in Photo-Biomodulation of Human Fibroblasts In Vitro," Lasers in Surgery and Medicine, Volume 12, pp. 528-537 (1992), which is incorporated in its entirety by reference herein.

A prominent feature of early Parkinson's disease is the damage to the neuronal processes (e.g., axons and their synapses) that communicate with other neurons. Axons are thin, cylindrical processes that extend so far from the neuronal cell that they require an axonal transport system to supply vital nutrients and important organelles like mitochondria and synaptic vesicles. One recent hypothesis to explain why axons and synapses are damaged in Parkinson's disease patients is a failure in the axonal transport system in dopaminergic neurons.

To determine if axonal transport is defective, two different models of sporadic Parkinson's disease have been previously used in studies by Dr. Patricia Trimmer et al. of the University of Virginia Department of Neuroscience. In these studies, axonal transport of mitochondria was found to be significantly reduced in processes of Parkinson's disease cybrids (unique human neuronal cell lines that contain the mitochondrial DNA of individual Parkinson's disease patients and which share many important attributes with injured dopaminergic neurons in the brains of Parkinson's disease patients) and similar human neuronal cells exposed to rotenone (a pesticide that damages neurons in a manner that resembles Parkinson's disease). These findings suggest that reduced axonal transport plays an important role in the early stages of Parkinson's disease.

Studies which have exposed Parkinson's disease cybrid cells and rotenone-treated neuronal cells to low energy laser treatment have found that axonal transport of mitochondria was restored. Such studies illustrate that low energy laser treatment can improve the supply of vital nutrients and organelles to axons and synapses in Parkinson's disease to compensate at least in part for the reduced axonal transport. In view of the hypothesis that axonal transport of essential nutrients is reduced in Parkinson's disease, certain embodiments described herein advantageously provide low energy laser treatment to combat this reduction of transport. In certain embodiments described herein, delivering electromagnetic radiation to brain cells causes an improvement of mitochondrial function in irradiated neurons.

In certain embodiments, the apparatus and methods of phototherapy described herein increase the cerebral blood flow of the patient. In certain such embodiments, the cerebral blood flow is increased by at least about 5%, 10%, 15%, 20%, or 25% immediately post-irradiation, as compared to immediately prior to irradiation.

A number of studies have investigated the effects of in vitro irradiation of cells using pulsed light on various aspects of the cells. A study of the action mechanisms of incoherent pulsed radiation at a wavelength of 820 nanometers (pulse repetition frequency of 10 Hz, pulse width of 20 milliseconds, dark period between pulses of 80 milliseconds, and duty factor (pulse duration to pulse period ratio) of 20%) on in vitro cellular adhesion has found that pulsed infrared radiation at 820 nanometers increases the cell-matrix attachment. (T. I. Karu et al., "*Cell Attachment to Extracellular Matrices is Modulated by Pulsed Radiation at* 820 *nm and Chemicals that Modify the Activity of Enzymes in the Plasma Membrane*," Lasers in Surgery and Medicine, Vol. 29, pp. 274-281 (2001) which is incorporated in its entirety by reference herein.) It was hypothesized in this study that the modulation of the monovalent ion fluxes through the plasma membrane, and not the release of arachidonic acid, is involved in the cellular signaling pathways activated by irradiation at 820 nanometers. A study of light-induced changes to the membrane conductance of ventral photoreceptor cells found behavior which was dependent on the pulse parameters, indicative of two light-induced membrane processes. (J. E. Lisman et al., "*Two Light-Induced Processes in the Photoreceptor Cells of Limulus Ventral Eye*," J. Gen. Physiology, Vol. 58, pp. 544-561 (1971), which is incorporated in its entirety by reference herein.) Studies of laser-activated electron injection into oxidized cytochrome c oxidase observed kinetics which establish the reaction sequence of the proton pump mechanism and some of its thermodynamic properties have time constants on the order of a few milliseconds. (I. Belevich et al., "*Exploring the proton pump mechanism of cytochrome c oxidase in real time*," Proc. Nat'l Acad. Sci., Vol. 104, pp. 2685-2690 (2007); I. Belevich et al., "*Proton-coupled electron transfer drives the proton pump of cytochrome c oxidase*," Nature, Vol. 440, pp. 829-832 (2006), both of which are incorporated in its entirety by reference herein.) An in vivo study of neural activation based on pulsed infrared light proposed a photo-thermal effect from transient tissue temperature changes resulting in direct or indirect activation of transmembrane ion channels causing propagation of the action potential. (J. Wells et al., "*Biophysical mechanisms responsible for pulsed low-level laser excitation of neural tissue,*" Proc. SPIE, Vol. 6084, pp. 60840X (2006), which is incorporated in its entirety by reference herein.)

In certain embodiments, delivering the neuroprotective amount of light energy includes selecting a surface power density of the light energy at the scalp 30 corresponding to the predetermined power density at the target area of the brain 20. As described above, light propagating through tissue is scattered and absorbed by the tissue. Calculations of the power density to be applied to the scalp 30 so as to deliver a predetermined power density to the selected target area of the brain 20 preferably take into account the attenuation of the light energy as it propagates through the skin and other tissues, such as bone and brain tissue. Factors known to affect the attenuation of light propagating to the brain 20 from the scalp 30 include, but are not limited to, skin pigmentation, the presence and color of hair over the area to be treated, amount of fat tissue, the presence of bruised tissue, skull thickness, and the location of the target area of the brain 20, particularly the depth of the area relative to the surface of the scalp 30. For example, to obtain a desired power density of approximately 50 mW/cm$^2$ in the brain 20 at a depth of 3 cm below the surface of the scalp 30, phototherapy may utilize an applied power density of approximately 3500 mW/cm$^2$. The higher the level of skin pigmentation, the higher the power density applied to the scalp 30 to deliver a predetermined power density of light energy to a subsurface site of the brain 20. As discussed above, in some embodiments, blanching of the scalp (or other patient surface) defines, in part, the amount of light emission necessary to achieve a desired irradiance at the target tissue.

In certain embodiments, treating a patient suffering from the effects of neurodegenerative disease (e.g., Parkinson's disease) comprises placing the therapy apparatus 10 in contact with the scalp 30 and adjacent the target area of the patient's brain 20. The target area of the patient's brain 20 can be previously identified such as by using standard medical imaging techniques. In certain embodiments, treatment further includes calculating a surface power density at the scalp 30 which corresponds to a preselected power density at the target area of the patient's brain 20. The calculation of certain embodiments includes factors that affect the penetration of the light energy and thus the power density at the target area. These factors include, but are not limited to, the thickness of the patient's skull, type of hair and hair coloration, skin coloration and pigmentation, patient's age, patient's gender, and the distance to the target area within the brain 20. The power density and other parameters of the applied light are then adjusted according to the results of the calculation.

The power density selected to be applied to the target area of the patient's brain 20 depends on a number of factors, including, but not limited to, the wavelength of the applied light, the type of CVA (ischemic or hemorrhagic), and the patient's clinical condition, including the extent of the affected brain area. The power density of light energy to be delivered to the target area of the patient's brain (or other tissue) may also be adjusted to be combined with any other therapeutic agent or agents, especially pharmaceutical neuroprotective agents (or for example, stem cell mobilizing compounds), to achieve the desired biological effect. In such embodiments, the selected power density can also depend on the additional therapeutic agent or agents chosen.

In certain embodiments, the treatment per treatment site proceeds continuously for a period of about 10 seconds to about 2 hours, more preferably for a period of about 1 to about 10 minutes, and most preferably for a period of about 1 to 5 minutes. For example, the treatment time per treatment site in certain embodiments is about two minutes. In other embodiments, the light energy is preferably delivered for at least one treatment period of at least about five minutes, and more preferably for at least one treatment period of at least ten minutes. The minimum treatment time of certain embodiments is limited by the biological response time (which is on the order of microseconds). The maximum treatment time of certain embodiments is limited by heating and by practical treatment times. The light energy can be pulsed during the treatment period or the light energy can be continuously applied during the treatment period.

In certain embodiments, the treatment may be terminated after one treatment period, while in other embodiments, the treatment may be repeated for at least two treatment periods. The time between subsequent treatment periods is preferably at least about five minutes, more preferably at least about 1 to 2 days, and most preferably at least about one week. In certain embodiments in which treatment is performed over the course of multiple days, the apparatus 10 is wearable over multiple concurrent days (e.g., embodiments of FIGS. 1, 3, 9A, 10, 13, and others disclosed, though not expressly depicted). The length of treatment time and frequency of treatment periods can depend on several factors, including the functional recovery of the patient and the results of imaging analysis of the infarct. In certain embodiments, one or more treatment parameters can be adjusted in response to a feedback signal from a device (e.g., magnetic resonance imaging) monitoring the patient.

During the treatment, the light energy may be continuously provided, or it may be pulsed. If the light is pulsed, the pulses are preferably range, in some embodiments from at least about 10 nanoseconds long to about 50 milliseconds long, including about 10-100 ns, 100-500 ns, 500 ns-1 ms, 1 ms-5 ms, 5-10 ms, 10-15 ms, 15-20 ms, 20-30 ms, 30-40 ms, 40-50 ms, and occur overlapping ranges thereof. In some embodiments, pulses are administered for 1, 1.5, 2, 2.5, 3, 3.5, 4 or 4.5 milliseconds. In some embodiments, pulses are administered for longer than 50 milliseconds (e.g., 100 ms, 250 ms, 500 ms, 1 s, or higher). Pulsed light is administered, in some embodiments at a frequency of up to about 100 kHz. In several embodiments, lower frequencies are used, such as, for example, frequencies ranging from 50-150 Hz. In some embodiments, pulsed light is administered at about 60, 70, 80, 90, 95, 100, 105, 110, 115, 120, 130, and 140 Hz. Frequencies less than 50 Hz and greater than 150 Hz are used in some embodiments. For example, in several embodiments, frequencies that match endogenous neural frequencies (e.g., Alpha, Beta, Delta, and/or Theta waves) are used. In some embodiments pulsed light administration is preferred because of a reduction in the amount of heat generated in the target tissue. Parameters may be chosen, in some embodiments to minimize heat. However, certain embodiments are particularly unexpected because the parameters used to generate the most robust effects are not the same as those that would minimize heat generation. As such, certain such embodiments may more specifically target and affect a biological system (e.g. stem cell engraftment or proliferation) as compared to those parameters used to minimize heat.

In some embodiments, pulses described herein are administered in an on/off cycle (e.g., a duty cycle). In some embodiments, the duty cycle is between 0.01% to about 99.9% (e.g., between about 0.01%-0.1%, 0.1%-1%, 1%-10%, 10%-20%, 20%-30%, 30%-40%, 40%-50%, 50%-60%, 60%-70%, 70%-80%, 80%-90%, 90%-99.9%, and overlapping ranges thereof). In one embodiment, the on time is 2 ms and the off time is 1-2 ms. In another embodiment, the on time is about 1-5 ms and the off time is about 1-5 ms. In some embodiments, the on/off times are variable during the course of treatment. For example, in one embodiment, the on or off times are increased (or decreased) by about 10-50% during the course of treatment.

In several embodiments, the duty cycle is synchronized with natural neuronal rhythms. Mammalian neurons generate wave patterns of neuronal firing that can be detected and measured by electroencephalography. The primary types of neuronal waves that have been detected are Alpha, Beta, Delta, and Theta waves.

Alpha waves occur in a frequency range of 8-13 Hz and are associated with states of low levels of activity or non-arousal. For example, after completing a task and taking a period of rest, alpha waves may be generated. Alpha waves are also associated with meditative states. Thus, in several embodiments synchronizing the duty cycle with alpha waves enhances the normal effects associated with generation of alpha waves, e.g., relaxation, deeper thought etc.

Beta waves occur at frequencies ranging from about 13-40 Hz are associated with higher levels of arousal and active engagement in mental activities. In several embodiments, synchronizing the duty cycle with beta waves enhances the ability of an individual performing tasks associated with beta wave generation. For example, in some embodiments, LLLT synchronized with beta waves enables longer periods of concentration, enhanced mental acuity, reduced fatigue after periods of mental activity, etc.

Delta waves occur at frequencies ranging from about 1-4 Hz, the slowest frequency of the various brain waves. Deep sleep commonly generates Delta waves. In several embodiments, LLLT synchronized with delta waves generation enhances the depth and/or perceived quality of sleep and/or deep relaxation. In some embodiments, LLLT is used as a sleep aid, such as for insomniacs, light sleepers, or those who have difficulty sleeping through the night. In some embodiments, LLLT can be used to enhance sleep sessions of those individuals having uncommon or variable work hours (e.g., work at night and sleep during the day).

Theta waves occur at frequencies ranging from about 4-7 Hz. Theta waves may be generated when a person is aware of his/her surroundings but daydreaming or otherwise not focusing on any task in particular. Is some cases, theta waves are associated with free flow of thought and generation of creative ideas. In several embodiments, LLLT synchronized with theta waves enhances an individual's creative thought process enables an individual to generate new ideas and/or thoughts. Such embodiments can be used to, among other applications, assist in overcoming mental blocks (e.g., writer's block or phobias), enhance the efficiency of brainstorming sessions, and/or assist individuals or groups in problem solving.

In some embodiments, the duty cycle is selected to reflect cellular refractory periods (e.g., the refractory period of a cardiac cell).

The course of the action potential in excitable cells comprises five parts: the rising phase, the peak phase, the falling phase, the undershoot phase, and finally the refractory period. During the rising phase the membrane potential depolarizes (becomes more positive, typically from a resting potential of about −70 mV), due to opening of voltage-gated sodium ion channels open, which increases membrane conductance for sodium ions. Once the membrane potential reaches a depolarization threshold (about −35 to about −40 mV) the opening of sodium channels will cause other sodium channels open, resulting in a feed-forward rapid depolarization. The point at which depolarization stops is called the peak phase. At this stage, the membrane potential reaches a maximum. Subsequent to this, there is a falling phase. During this stage the membrane potential hyperpolarizes (becomes more negative). During repolarization, voltage-gated sodium ion channels inactivate and voltage-gated potassium channels activate. Both the sodium ion channels closing and the potassium ion channels opening act to repolarize the cell's membrane potential back towards the resting membrane potential.

However, the potassium conductance has a lag time that leads to a short hyperpolarization, known as the undershoot phase. This period of hyperpolarization is known as the refractory period. Eventually this potassium conductance drops and the exits the refractory period and cell returns to its resting membrane potential.

There are two refractory periods in excitable cells (e.g., neurons). The absolute refractory period is the time period after a first stimulation during which a second stimulation of the cell will not trigger an action potential (or other cellular response normally associated with a stimulus). The absolute refractory period of neurons typically range from about 1 to about 3 milliseconds. Thus, in several embodiments, the duty cycle is adjusted to provide light administration to the cells (e.g., neurons) approximately every 1-3 milliseconds, or in sync with the absolute refractory period The relative refractory period is the time period after a first stimulation during which the probability of a second stimulation of the cell triggering an action potential (or other cellular response normally associated with a stimulus) is reduced, but an action potential may still be possible. The relative refractory period immediately follows the absolute refractory period. During the relative refractory period, a stimulus will need to be proportionally greater (to account for the hyperpolarization) in order to cause the membrane potential of the cell to reach the depolarization threshold, and initiate a new action potential. Absent an additional stimulus, the potassium conductance will return to its resting value and the membrane potential of the cell will return to equilibrium, thus ending the relative refractory period.

As the refractory period is varied depending on the cell type, greater or lesser refractory periods can be accommodated by adjusting the duty cycle. For example, in some embodiments, the duty cycle is adjusted to provide light to the cell approximately every 0.8-1.0 seconds, 1.0-1.2 seconds, 1.2-1.4 seconds, 1.4-1.6 seconds, 1.6-1.8 seconds, 1.8-2.0 seconds, 2.0-2.2 seconds, 2.2-2.4 seconds, 2.4-2.6 seconds, 2.6-2.8 seconds, and 2.8-3.0 seconds (and overlapping ranges thereof). Synchronization of LLLT, in some embodiments, enhances the function of the exposed cells. For example, synchronizing light administration with the refractory period of a sensory neuron, in some embodiments, increases the rate of sensory transmission in the neuron, which, in some embodiments, produces heightened sensory capacity. Additionally, synchronization of LLLT with the refractory period of motor neurons, in some embodiments, aids in normalization of neuronal firing rates, thereby increasing fine motor control and/or serving as a therapy or palsies or other such uncontrolled muscle movements.

In some embodiments, LLLT, whether continuous or pulsed, is administered for a total time (duration per treatment session at one site) of about 1 second to 10 minutes, e.g., between about 1 s to 25 s, 25 s-50 s, 50 s-100 s, 1 minute-2 minutes, 2 minutes-3 minutes, 3 minutes-4 minutes, 4 minutes-5 minutes, 5 minutes-6 minutes, 6 minutes-7 minutes, 7 minutes-8 minutes, 8 minutes-9 minutes, 9 minutes-10 minutes, or greater. In some embodiments, the total time (duration per treatment session at one site) is about 40, 50, 60, 70, 60, 90 100, 110, 120 seconds. In several embodiments, treatment is performed on one or more sites (e.g., 2, 3, 4, 5, 10, 15, 20, 25, 30 or more sites). In several embodiments, multiple treatment sessions are performed at different times (e.g., different hours, different days, etc.) on the same site (or at different sites).

In one embodiment, the invention comprises delivering pulsed LLLT to a neuron (or group neurons) every 1-2 milliseconds. In one embodiment, the invention comprises delivering pulsed LLLT to a cell (e.g., an excitable cell such as a neuron) in synchronicity with the activation or deactivation of an ion channel (e.g., sodium, calcium or potassium channel). In some embodiments, the LLLT is administered before an action potential occurs. In several embodiments, LLLT is administered in sync with the depolarization phase of the action potential. In several embodiments, LLLT is administered in sync with the peak phase of the action potential. In several embodiments, LLLT is administered in sync with the repolarization phase of the action potential. In several embodiments, LLLT is administered in sync with the hyperpolarization phase of the action potential. In some embodiments, the LLLT is administered during the relative refractory period, while in some embodiments, the LLLT is administered during the relative refractory period. In several embodiments, LLLT is administered for a period of time that overlaps one or more phases of an action potential. In several embodiments, LLLT is administered in sync, preceding, or following a particular action potential event. For example, in some embodiments, LLLT is administered based on the opening of sodium channels, while in some embodiments, LLLT is administered based on the potassium induced hyperpolarization of the cell membrane.

In certain embodiments, the treatment per treatment site proceeds continuously for a period of about 10 seconds to about 2 hours, for a period of about 1 to about 10 minutes, or for a period of about 1 to 5 minutes. For example, the treatment time per treatment site in certain embodiments is about two minutes. In other embodiments, the light energy is delivered for at least one treatment period of at least about five minutes, or for at least one treatment period of at least ten minutes. The minimum treatment time of certain embodiments is limited by the biological response time (which is on the order of microseconds). The maximum treatment time of certain embodiments is limited by heating and by practical treatment times (e.g., completing treatment prior to or between other treatment regimens). The light energy can be pulsed during the treatment period or the light energy can be continuously applied during the treatment period. If the light is pulsed, the pulses can be 2 milliseconds long and occur at a frequency of 100 Hz, although longer pulselengths and lower frequencies can be used, or at least about 10 nanosecond long and occur at a frequency of up to about 100 kHz.

In certain embodiments, the treatment may be terminated after one treatment period, while in other embodiments, the treatment may be repeated for at least two treatment periods. The time between subsequent treatment periods can be at least about five minutes, at least two in a 24-hour period, at least about 1 to 2 days, or at least about one week. The length of treatment time and frequency of treatment periods can depend on several factors, including the functional recovery of the patient. In certain embodiments, one or more treatment parameters can be adjusted in response to a feedback signal from a device (e.g., magnetic resonance imaging) monitoring the patient.

In addition to the combination of cell therapy and phototherapy, in certain embodiments, the phototherapy is combined with other types of treatments for an improved therapeutic effect. Treatment can comprise directing light through the scalp of the patient to a target area of the brain concurrently with applying an electromagnetic field to the brain. Similar approaches are taken to treat other target tissues. In such embodiments, the light has an efficacious power density at the target area and the electromagnetic field has an efficacious field strength. For example, the apparatus 50 can also include systems for electromagnetic treatment, e.g., as described in U.S. Pat. No. 6,042,531 issued to Holcomb, which is incorporated in its entirety by reference herein. In certain embodiments, the electromagnetic field comprises a magnetic field, while in other embodiments, the electromagnetic field comprises a radio-frequency (RF) field. As another example, treatment can comprise directing an efficacious power density of light through the scalp of the patient to a target area of the brain concurrently with applying an efficacious amount of ultrasonic energy to the brain. Such a system can include systems for ultrasonic treatment, e.g., as described in U.S. Pat. No. 5,054,470 issued to Fry et al., which is incorporated in its entirety by reference herein.

Assessing Efficacy of Light Therapy and Cell Therapy

Depending on the disease or injury treated by LLLT and cell therapy, various endpoints are used to assess the efficacy of the therapies. For example, neurologic function scales can be used to quantify or otherwise characterize the efficacy of various embodiments described herein. Neurologic function scales generally use a number of levels or points, each point corresponding to an aspect of the patient's condition. The number of points for a patient can be used to quantify the patient's condition, and improvements in the patient's condition can be expressed by changes of the number of points. One example neurologic function scale used as a clinical tool for diagnosis and determining severity of Parkinson's disease is the Unified Parkinson's Disease Rating Scale (UPDRS) which comprises various sections evaluated by interview and clinical observation. In certain embodiments, two or more of the neurologic function scales can be used in combination with one another, and can provide longer-term measurements of efficacy (e.g., at three months).

In certain embodiments described herein, a patient exhibiting symptoms of Parkinson's disease is treated by irradiating a plurality of treatment sites on the patient's scalp. The irradiation is performed utilizing irradiation parameters (e.g., wavelength, power density, time period of irradiation, etc.) which, when applied to members of a treated group of patients, produce at least a 2% average difference between the treated group and a placebo group on at least one neurologic function scale (e.g., UPDRS) analyzed in dichotomized or any other fashion. Certain other embodiments produce at least a 4% average difference, at least a 6% average difference, or at least a 10% average difference between treated and placebo groups on at least one neurologic function scale analyzed in dichotomized or any other fashion. In certain embodiments, the irradiation of the patient's scalp produces a change in the patient's condition. In certain such embodiments, the change in the patient's condition corresponds to a change in the number of points indicative of the patient's condition. In certain such embodiments, the irradiation produces a change of one point, a change of two points, a change of three points, or a change of more than three points on a neurologic function scale.

Other diseases or injuries that are treated with LLLT and cell therapy can be assessed by standard clinical measures related to that disease or injury. For example, treatment of cardiac tissue damage after MI can be evaluated by laboratory measurements of total cardiac output, echocardiography to measure ventricular function, or stress testing to measure an individual's overall cardiovascular performance. Effects of administration of a stem cell mobilizing compound and LLLT irradiation of bone marrow can be measured by a complete blood count.

Possible Action Mechanisms

The following section discusses theories and potential action mechanisms, as they presently appear to the inventors, for certain embodiments of phototherapy described herein. The scope of the claims of the present application is not to be construed to depend on the accuracy, relevance, or specifics of any of these theories or potential action mechanisms. Thus the claims of the present application are to be construed without being bound by theory or by a specific mechanism.

Figure 34:
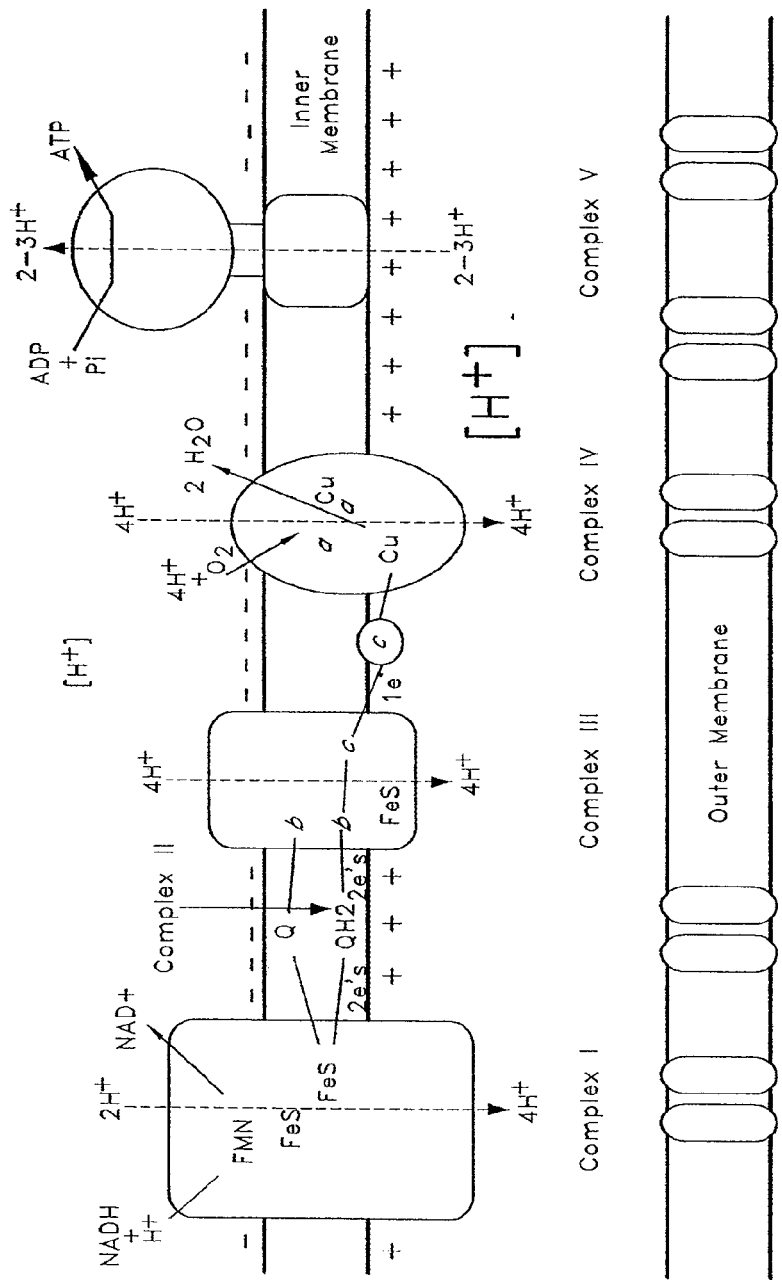
FIG. 34 is a schematic diagram of the electron transport chain in mitochondria.

There are five large components of the electron transfer chain, Complexes I-IV and the ATPase (also called Complex V), with each complex containing a number of individual proteins (see FIG. 34). One of the critical complexes, Complex IV (cytochrome oxidase), is the component responsible for the metabolism of oxygen. The cytochrome C oxidase protein is a key player in the electron transfer in Complex IV through its copper centers. In several embodiments, administered light is absorbed (photoaccepted) by one or more of these copper centers.

As an aside, cytochrome C oxidase has enjoyed a renaissance in the last few years as an important factor in the regulation of apoptosis (programmed cell death). Release of cytochrome C oxidase from the mitochondria into the cytosol is a pro-apoptotic signal.

Light is known to affect biological systems, such as vision, regulation of circadian hormones, melanin production, and Vitamin D synthesis. With respect to specific organelles, specific wavelengths of light targeted at the cytochrome C receptor in the mitochondria can preserve mitochondrial function, as well as, reduce the size of myocardial infarcts and stroke. It has also been shown that these effects can be reproduced across multiple species. Given that there is some conservation of the mitochondrial target receptor (i.e., copper ions in cytochrome C) between species, effects demonstrated in animal models are likely to be readily translated to similar effects in human patients. These effects may be due to production of new cells (neurogenesis), preservation of existing tissue (neuroprotection) or a combination of both.

The mitochondria convert oxygen and a carbon source to water and carbon dioxide, producing energy (as ATP) and reducing equivalents (redox state) in the process. The process details of the electron transport chain in mitochondria are schematically diagrammed in FIG. 34. The chemical energy released from glucose and oxygen is converted to a proton gradient across the inner membrane of the mitochondria. This gradient is, in turn, used by the ATPase complex to make ATP. In addition, the flow of electrons down the electron transfer chain produces NADPH and NADH (and other factors such as FAD). These cofactors are important for maintaining the redox potential inside the cell within the optimal range. This process has been called the chemiosmotic theory of mitochondrial function (Dr. Peter Mitchell was awarded a Nobel Prize in chemistry for elucidating these key processes).

The clinical and cellular responses to light for in vivo treatment efficacy of ischemic conditions of acute myocardial infarction and stroke has been demonstrated in multiple validated animal models. As described more herein, these effects are wavelength-specific. In several embodiments, the wavelength specificity may be dependent upon a known mitochondrial receptor (cyctochrome C oxidase). In some embodiments, targeting of this receptor results in formation of adenosine triphosphate (ATP), enhanced mitochondrial survival, and/or maintenance of cytochrome C oxidase activity.

In stroke, the occlusion of a major artery results in a core area of severe ischemia (e.g., with significant reductions in blood flow, for example flow reduced to less than 20% of pre-occlusion levels). The core area has a rapid loss of ATP and energy production, and the neurons are depolarized. This core of the infarct is surrounded by an ischemic penumbra which can be up to twice as large as the core of the infarct. Cells within the penumbra show less severe decreases in loss of blood flow (e.g., ranging up to 20 to 40%, or more, of normal). Neurons in the penumbra tend to be hyperpolarized and electrically silent. In the penumbra, the cells undergo progression of cell death lasting from hours to days after the infarct. Also, inflammation after infarct can play a role in determining the final infarct size and anti-inflammatory modulators can reduce infarct size. The infarct is dynamic, with different parts of the infarct being affected to different degrees over a period of hours to days. Photon therapy has been implicated in a number of physiological processes that could favor cell survival in the penumbral region of a stroke.

The action of light on a cell is mediated by one or more specific photo acceptors. A photo acceptor molecule first absorbs the light. After this absorptive event and promotion of an electron to an excited state, one or more primary molecular processes from these high energy states can lead to a measurable biological effect at the cellular level. An action spectra represents the biological activity as a function of wavelength, frequency or photon energy. Karu was the first researcher to propose that the action spectra should resemble the absorption spectra of the photoacceptor molecule. Since an absorptive event occurs for a transfer of energy to take place, the stimulatory wavelengths of the action spectra falls within the absorptive spectra of the photo acceptor.

Figure 36:
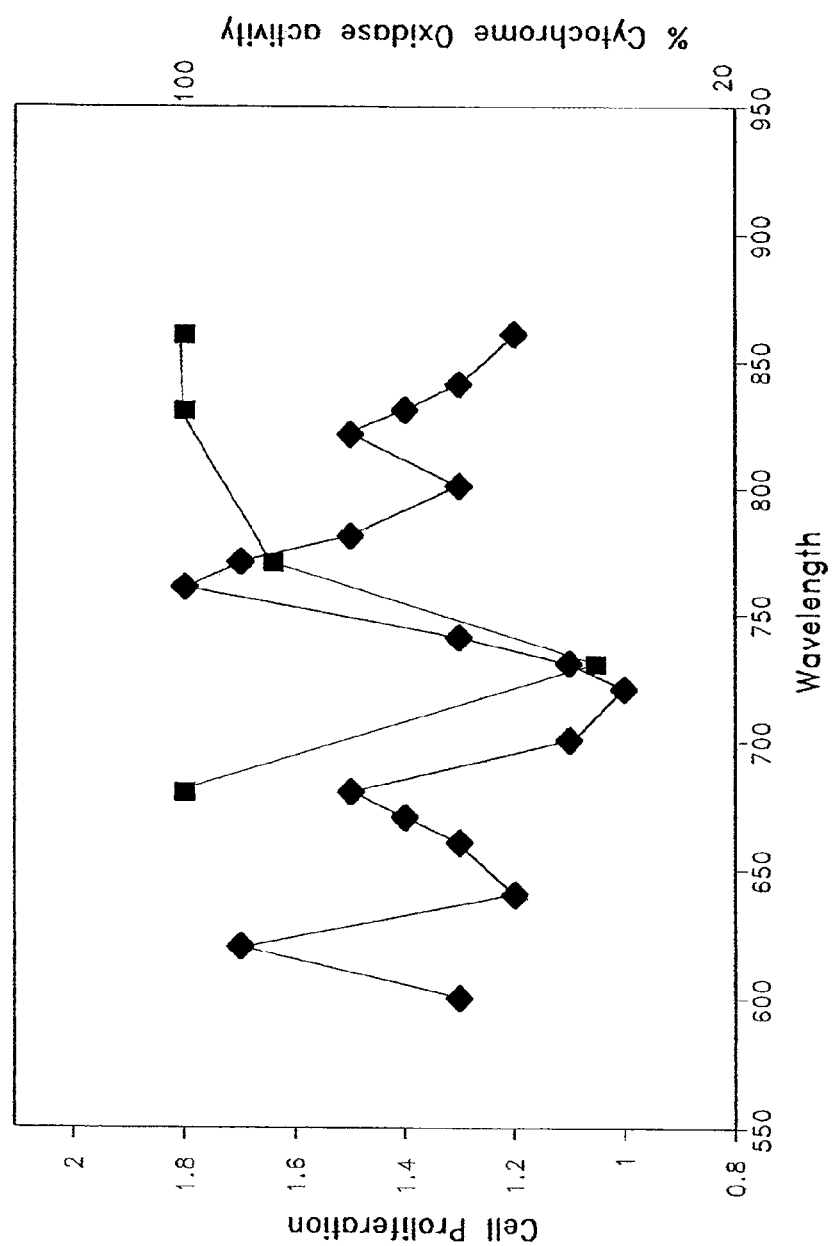
FIG. 36 is a graph of cell proliferation and cytochrome oxidase activity percentage as functions of the wavelength of light used to stimulate mammalian cells.

It has been postulated by others that light can directly activate Complex IV and indirectly driving the production of ATP via ATPase (and reducing equivalents). For example, Karu studied the activation spectra of these processes and found that wavelengths that maximally stimulated energy-dependant cellular functions corresponded to the absorption bands of the copper centers in cytochrome C oxidase. FIG. 36 is a graph of cell proliferation and cytochrome oxidase activity percentage as functions of the wavelength of light used to stimulate mammalian cells. Based on these results, wavelengths of 620, 680, 760, and 820 nanometers (±10 nanometers) promote cellular activities. The 620 and 820 nanometer wavelengths are close to the strongest copper absorption maxima of 635 and 810 nanometers.

Karu was also the first to propose a specific mechanism for photon therapy at the cellular level (see, e.g., T. Karu, "*Photobiological Fundamentals of Low Power Laser Therapy,*" IEEE Journal of Quantum Electronics, 1987, Vol. 23, page 1703; T. Karu, "*Mechanisms of interaction of monochromatic visible light with cells,*" Proc. SPIE, 1995, Vol. 2630, pages 2-9). Karu's hypothesis was based on the absorption of monochromatic visible and near infrared radiation by components of the cellular respiratory chain. Absorption and promotion of electronically excited states cause changes in redox properties of these molecules and acceleration of electron transfer (primary reactions). Primary reactions in mitochondria of eukaryotic cells are followed by a cascade of secondary reactions occurring in the cytoplasm, cell membrane, and nucleus. Karu defined the action spectra for mammalian cells of several secondary reactions (DNA, RNA synthesis, cellular adhesion). The action spectra for all of these secondary markers were very similar, suggesting a common photo acceptor. Karu then compared these action spectra with absorption spectra of the copper centers of cytochrome C oxidase in both reduced and oxidized states. Cytochrome C oxidase contains four redox active metal centers and has a strong absorbance in the near infrared spectral range. The spectral absorbance of cytochrome C oxidase and the action spectra were very similar. Based on this, Karu suggested that the primary photoacceptors are mixed valence copper centers within cytochrome C oxidase.

Cytochrome C oxidase is the terminal enzyme of the mitochondrial electron transport chain of all eukaryotes and is required for the proper function of almost all cells, especially those of highly metabolically active organs, such as the brain and heart. Cytochrome C has also been suggested to be the critical chromophore responsible for stimulatory effects of irradiation with infrared light to reverse the reduction in cytochrome C oxidase activity produced by the blockade of voltage dependent sodium channels with tetrodotoxin and up regulated cytochrome C activity in primary neuronal cells. It has been demonstrated by researchers (see, e.g., M. T. Wong-Riley et al., *NeuroReport*, 2001, Vol. 12, pages 3033-3037; J. T. Eells et al., *Proceedings National Academy of Science*, 2003, Vol. 100, pages 3439-3444) that in vivo, rat retinal neurons are protected from damage induced by methanol intoxication. Methanol's toxic metabolite is formic acid which inhibits cytochrome C.

Several investigators have demonstrated the increased synthesis of ATP from infrared irradiation both in vitro and in vivo. Karu has shown that irradiation of cells in vitro at wavelengths of 632 nanometers, 670 nanometers, and 820 nanometers can increase mitochondrial activity.

Additional data from other groups suggest that cytochrome C oxidase is an important target. Light (670 nanometers) can rescue primary neurons from the toxic effects of the sodium channel blocker tetrodotoxin (TTX). TTX reduces cytochrome oxidase activity in treated neurons, and this reduction is reversed by light treatment (an increase in cytochrome oxidase activity). In an in vivo model, 670 nanometer light is used to rescue retinal function in a methanol-mediated model of retinal damage. Methanol is metabolized to formate, a selective mitochondrial toxin targeted at cytochrome C oxidase. Irradiation with light (670 nanometers) rescued the retina from damage induced by methanol.

Several studies hypothesize that photon therapy would be effective in animal models for acute myocardial infarction (AMI) and ischemic stroke, by virtue of the photon therapy inducing a cascade of signaling events initiated by the initial absorption of light by cytochrome C. These signaling events apparently up-and-down regulate genes, transcription factors, as well as increase mitochondrial function.

Without being bound by theory or a specific mechanism, in stroke, reduction of infarct volume may occur in one of two ways or a combination of both: (i) preservation of existing tissue (neuroprotection), and (ii) generation of new tissue (neurogenesis). A number in vitro and in vivo studies appear to support both of these potential mechanisms. The potential effects of NIR light on neurogenesis are straightforward; it either increases the number of new cells, or it prevents the loss of new cells that are generated as a result of the ischemic insult. Neuroprotection can result from at least three mechanisms: (i) direct stimulation of tissue survival; (ii) indirect stimulation of tissue survival (e.g., increased growth factor activity); and (iii) decrease in toxic factors. Analogous mechanisms are likely involved in the survival of other tissues in response to injury (e.g., cardioprotective mechanism).

Figure 35:
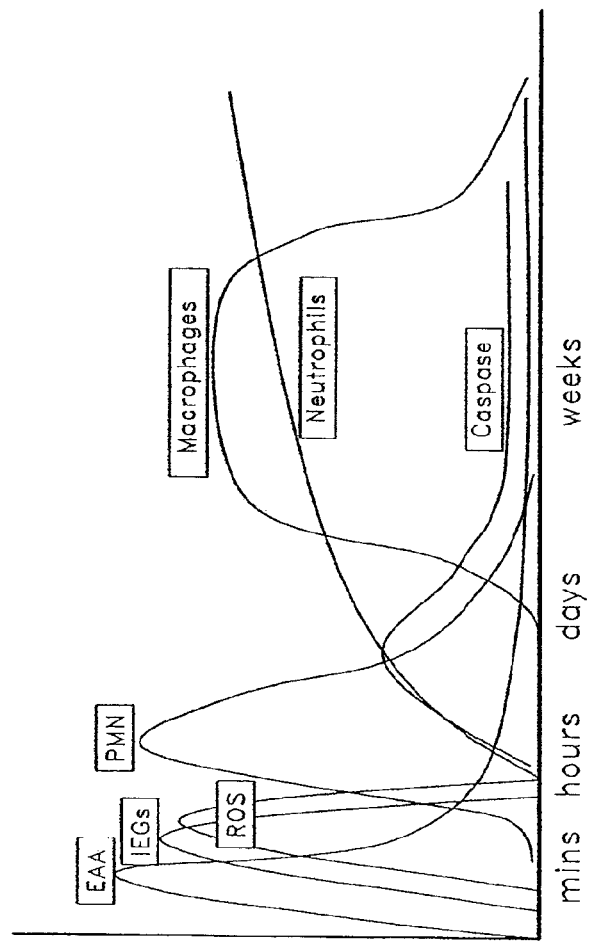
FIG. 35 is a graph which shows mediators responsible for ischemic stroke tissue damage and the time points at which they occur.

FIG. 35 is a graph which shows mediators responsible for ischemic stroke tissue damage and the time points at which they occur. FIG. 35 illustrates several potential places where photon therapy could potentially intervene to reduce infarct severity. Early after ischemic stroke, excitatory amino acids (EAAs) induce $Ca^{2+}$ influx via NMDA receptor activation leading to neuronal and glial cell injury. A number of immediately early genes (IEGs) express such as c-fos, c-jun, within 30 minutes. Reactive oxygen species (ROSs) create lipid peroxidation and activated phagocytes which create further injury. ROSs damage most cellular components. Cytokines are then expressed causing migration of polymorphonuclear neutrophils (PMNs) into the ischemic brain. Macrophages and neutrophils follow into the brain parenchyma. Apoptosis occurs via caspase activation which further increases stroke damage.

Preservation of existing tissue (neuroprotection) can result from direct stimulation of the tissue (e.g., by ATP synthesis or by prevention of cytochrome C release from mitochondria). Ischemia results in depletion of ATP in the ischemic zone due to lack of oxygen and glucose. The resultant lack of ATP, depending on severity, results in decreased cellular function. In extreme cases, energy depletion leads to cell depolarization, calcium influx, and activation of necrotic and apoptotic processes. Near-infrared radiation (NIR) stimulates the production of ATP in a variety of cell types in culture, and in cardiac tissue. A single irradiation of infarcted cardiac tissue results in a statistically significant 3-fold increase in tissue ATP levels four hours after treatment. The effect of NIR is prolonged long after irradiation is ceased. The prolonged effect could also be due, in part, to preservation of mitochondrial function. NIR irradiated, infarcted cardiac tissue has exhibited over a 50% reduction in damaged mitochondria. After ischemia, the myocardial tissue that is not immediately lost is in a "stunned" state, and can remain stunned for a period of days. In particular, it is the mitochondria in the tissue that are stunned. Stunned mitochondria are still intact, but with characteristic morphological changes that are indicative of mitochondria that are not metabolically active. As such, even with restored blood flow, the mitochondria are unable to convert oxygen and glucose to useable energy (ATP).

Neuroprotection can also result from direct stimulation of the tissue by preventing cytochrome C release from mitochondria. The release of cytochrome C from the mitochondria into the cytoplasm is a potent apoptotic signal. Cytochrome C release results in the activation of caspase-3 and activation of apoptotic pathways. The apoptotic cells appear as soon as a few hours after stroke, but the cell numbers peak at 24 to 48 hours after reperfusion. In rat models of stroke, cytoplasmic cytochrome C can be detected out to at least 24 hours after the occlusion. In vitro 810-nanometer light can prevent the TTX-induced decrease in cytochrome oxidase activity. In several embodiments, photon therapy maintains cytochrome oxidase activity in vivo by preventing release of cytochrome C into the cytoplasm, resulting in the prevention of apoptosis. The release of cytochrome C is regulated by the Bcl/Bax system. Bax promotes release and Bcl decreases release. In myofiber cultures in vitro, NIR light promotes Bcl-2 expression and inhibits Bax expression, which fits with the prevention of cytochrome C release data. Thus, in some embodiments, light therapy has an effect on one or more levels of the biochemical cascade that controls neuronal (or cellular) viability.

Neuroprotection can also result from indirect stimulation (e.g., by angiogenesis or by up-regulation of cell survival genes and/or growth factors). Regarding angiogenesis and stroke, recent research indicates that the reduction in cerebral blood flow (CBF) can lead to compensatory neovascularization in the affected regions. The low CBF results in the up regulation of hypoxia inducible factor-1 (HIF-1), vascular endothelial growth factor (VEGF), and VEGF receptors. In the rat pMCAo model, infusion of VEGF results in a reduction of infarct size. In AMI models, VEGF is increased with photon therapy.

Regarding up-regulation of cell survival genes and/or growth factors, it has been shown that photon therapy may up-, and down-regulate certain beneficial genes. It is possible that these gene products can prevent or ameliorate apoptosis, which is known to occur throughout the stoke penumbra and in stunned myocardium of AMI. In AMI models, expression of the cardioprotective molecules HSP70 and VEGF are increased. In stroke, equivalent neuroprotective molecules could be up-regulated, preserving tissue and resulting in reduction of infarct volumes. A variety of factors have been implicated in neuroprotection in addition to VEGF, including BDNF, GDNF, EGF, FGF, NT-3, etc. In several embodiments, one or more of these of factors that are up-regulated to promote neuronal (or other cellular) survival. In some embodiments, LLLT increases one or more of the following: mitochondrial respiration, production of molecular oxygen, DNA synthesis, DNA repair, and cell proliferation. In certain embodiments, these factors play a role in enhancing the viability, proliferation, migration, and/or engraftment of administered stem cells.

Neuroprotection can also result from decreases in toxic factors (e.g., antioxidant protection or by reduction of deleterious factors to tissue function and survival). Regarding antioxidant protection, in some embodiments, NIR light may reduce damage induced by free radicals. By-products of free radical damage are found in damaged brain tissue following stroke. This damage is thought to be mediated by neutrophils during reperfusion injury. The nominal spin-trap agent NXY-059 (a free radical scavenger) reduces infarct size if given within 2.25 hours of a stroke (in rat, although it is more effective if given sooner). NIR light can induce the expression of catalase in AMI models. Catalase is a powerful anti-oxidant which can prevent free radical damage and, if produced in the area of the stroke, it may prevent loss via the same mechanism as NXY-059. Axon survival is known to be improved by catalase.

In addition, a number of cytokines and other factors are produced during reperfusion that are deleterious to tissue function and survival. These factors promote activity of existing phagocytic and lymphocytic cells as well as attract additional cells to the area of damage. In several embodiments, NIR light can decrease the levels of cytokines in models of neuronal damage. In particular, IL-6 and MCP-1 (pro-inflammatory cytokines) are induced in models of spinal cord damage. NIR light significantly reduces IL-6 and MCP-1 and promotes regrowth of the spinal cords neurons. IL-6 is thought to play a significant role in spinal cord damage in man also.

Regarding neurogenesis, in the last several years, it has been become well-established that the brain has the ability to generate new nerve cells in certain instances. Neural stem cells have been shown to exist in the periventricular areas and in the hippocampus. Naturally-occurring growth factors in the adult human brain can spur the production of new nerve cells from these stem cells. After a stroke, neurogenesis commences in the hippocampus with some cells actually migrating to the damaged area and becoming adult neurons.

In several embodiments, NIR light is effective because administration either increases the number of new cells that are formed, or prevents the loss of the newly formed cells. The latter may be more significant and the majority of newly-formed cells die within 2 to 5 weeks after the stroke (rat model). In an unpublished study by Oron, NIR light has been shown to increase the survival of cardiomyocytes implanted into infarcted heart. Other studies have shown the human neural progenitor cells can be induced to differentiate with stimulation of 810-nanometer irradiation without the presence of specific growth factors that are normally required for differentiation. In several embodiments, neurogenesis occurs due to the administered if the infrared irradiation acting as a stimulating signal much like a growth factor. Early data from a porcine study of AMI has shown that the 810-nanometer-irradiated pig myocardium showed evidence of cardiogenesis. This result was demonstrated by the presence of significant desmin staining in the laser treated group over control, and by ultrastructural analysis which demonstrated the presence of what appears to be developing cardiomyocytes.

In vitro and near in vitro like conditions (retinal studies) have previously demonstrated that light can induce beneficial effects in animals. Yet these effects required little if any ability to penetrate non-involved tissues. For treatments of Parkinson's disease by irradiation through intervening tissue, certain embodiments utilize wavelengths that can penetrate to the target tissue.

Light can be absorbed by a variety of chromophores. Some chromophores, such as cytochrome C oxidase can convert the light energy into chemical energy for the cell. Other chromophores can be simple and the light energy is converted to heat, for example water. The absorption of light energy is wavelength dependent and chromophore dependant.

Some chromophores, such as water or hemoglobin, are ubiquitous and absorb light to such a degree that little or no penetration of light energy into a tissue occurs. For example, water absorbs light above approximately 1300 nanometers. Thus energy in this range has little ability to penetrate tissue due to the water content. However, water is transparent or nearly transparent in wavelengths between 300 and 1300 nanometers. Another example is hemoglobin, which absorbs heavily in the region between 300 and 670 nanometers, but is reasonably transparent above 670 nanometers.

As discussed above, one can define an "IR window" into the body which encompasses certain wavelengths that are more or less likely to penetrate. The absorption/transmittance of various tissues have been directly measured to determine the utility of various wavelengths.

Figure 37:
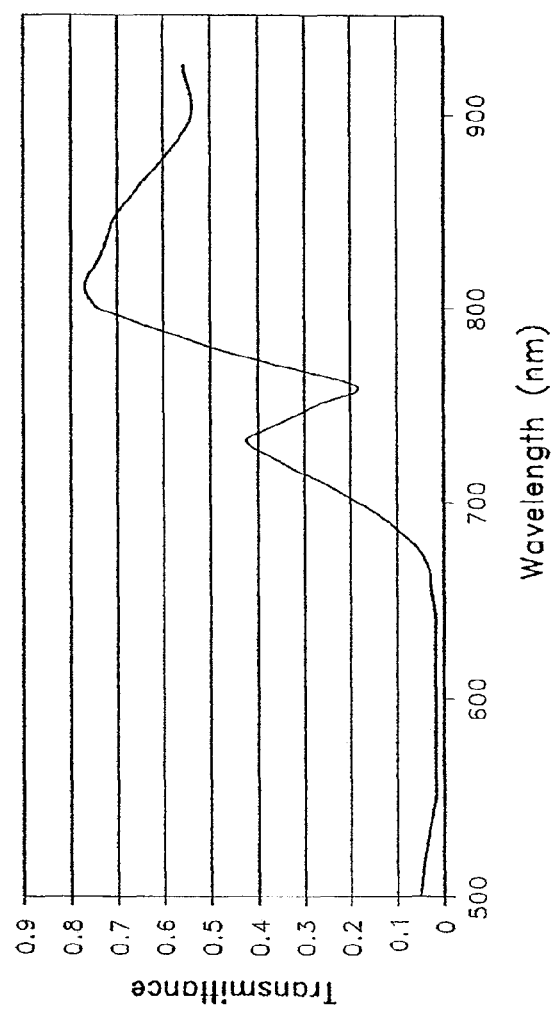
FIG. 37 is a graph of the transmittance of light through blood (in arbitrary units) as a function of wavelength.

FIG. 37 is a graph of the transmittance of light through blood (in arbitrary units) as a function of wavelength. Blood absorbs less in the region above 700 nanometers, and is particularly transparent at wavelengths above 780 nanometers. Wavelengths below 700 nanometers are heavily absorbed, and are not likely to be useful therapeutically (except for topical indications). However, in certain embodiments, wavelengths below 700 nm are beneficial, for example in treating stem cells prior to delivery to a subject (e.g., as an in vitro pre-treatment).

Figure 38:
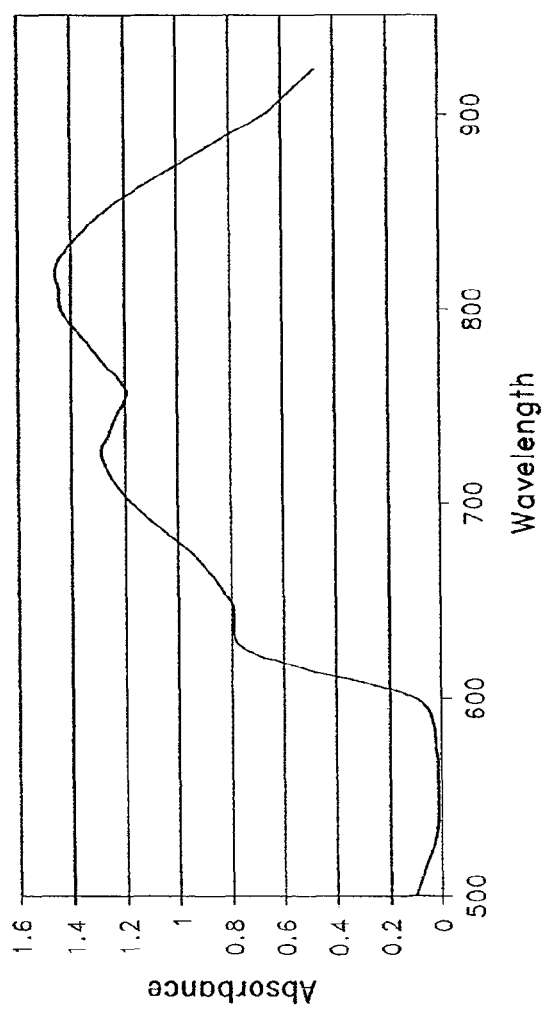
FIG. 38 is a graph of the absorption of light by brain tissue.

FIG. 38 is a graph of the absorption of light by brain tissue. Absorption in the brain is strong for wavelengths between 620 and 900 nanometers. This range is also where the copper centers in mitochondria absorb. The brain is particularly rich in mitochondria as it is a very active tissue metabolically (the brain accounts for 20% of blood flow and oxygen consumption). As such, the absorption of light in the 620 to 900 nanometer range is expected if a photostimulative effect is to take place. As discussed herein, in several embodiments, light is administered to the brain (whole or portions thereof) at wavelengths between about 620-900 nm.

Figure 39:
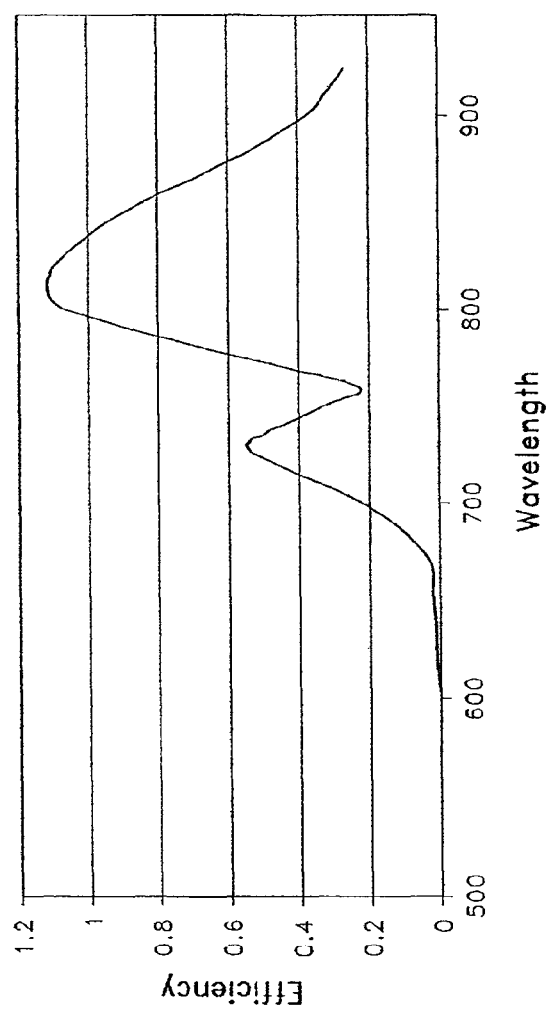
FIG. 39 is a graph of the efficiency of energy delivery as a function of wavelength.

By combining FIGS. 37 and 38, the efficiency of energy delivery as a function of wavelength can be calculated, as shown in FIG. 39. Wavelengths between 780 and 880 nanometers are preferable (efficiency of 0.6 or greater) for targeting the brain. The peak efficiency is about 800 to 830 nanometers (efficiency of 1.0 or greater). These wavelengths are not absorbed by water or hemoglobin, and are likely to penetrate to the brain. Once these wavelengths reach the brain, they will be absorbed by the brain and converted to useful energy in several embodiments.

Figure 40:
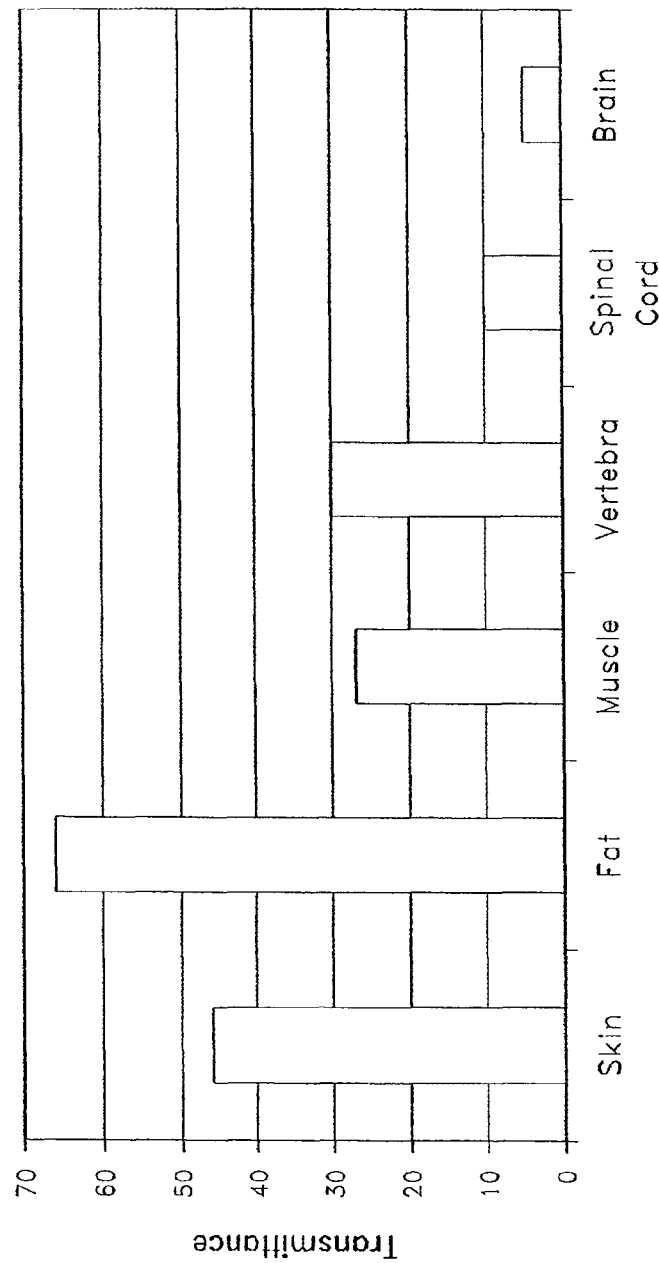
FIG. 40 is a bar graph of the absorption of 808 nanometer light through various rat tissues.

These effects have been directly demonstrated in rat tissues. The absorption of 808 nanometer light was measured through various rat tissues, as shown in FIG. 40. Soft tissues such as skin and fat absorb little light. Muscle, richer in mitochondria, absorbs more light. Even bone is fairly transparent. However, as noted above, brain tissue, as well as spinal cord tissue, absorb 808 nanometer light well.

Two wavelengths have demonstrated efficacy in animal models of ischemia/mitochondrial damage, namely, 670 nanometers and 808 nanometers. Light having a wavelength of 670 nanometers has shown efficacy in retinal damage. Light having a wavelength of 808 nanometers has demonstrated efficacy in animal models of myocardial infarction (as well as soft tissue injury).

The effects of near infrared light on soft tissue injury have been established in FDA approved trials for carpal tunnel syndrome (830 nanometers) and knee tendonitis (830 nanometers). In both cases, 830 nanometer light was superior to placebo for resolution of symptoms.

Light having a wavelength of 808 nanometers was also used to reduce infarct volume and mortality in myocardial infarction (MI) models in rat, dog, and pig. The MI models are particularly relevant to wavelength selection as similar processes—apoptosis, calcium flux, mitochondrial damage—have been implicated in stroke and MI.

Certain wavelengths of light are associated with activation of biological processes, and others are not. In particular, light mediated mitochondrial activation has been used as a marker of biostimulation. Given the lack of in vivo markers, the use of in vitro markers of light activation was used to help narrow down the large number of potential wavelengths. Wavelengths that activate mitochondria were determined, and these wavelengths were used in vivo models.

Penetration to the target tissue is also of importance. If a biological effect is to be stimulated, then the stimulus must reach the target tissue and cell. In this regard, wavelengths between 800 and 900 nanometers are useful, as they can penetrate into the body. In particular, wavelengths of 800 to 830 nanometers are efficient at penetrating to the brain and then being absorbed by the brain.

The use of 808 nanometer light has a solid basis for the treatment of stroke. This wavelength of light can penetrate to the target tissue (brain), is absorbed by the target tissue, stimulates mitochondrial function, and works in a related animal model of ischemia (MI). This supposition is supported by the striking finding that 808 nanometer light can reduce the neurological deficits and infarct volume associated with stroke (in rats).

Other wavelengths have some of these properties. For example, 670 nanometer light can promote mitochondrial function and preserve retinal neurons. However, this wavelength does not penetrate tissue well as it is highly absorbed by hemoglobin. It is therefore not useful in treating stroke or neurodegenerative conditions.

In certain embodiments, wavelengths from 630 to 904 nanometers may be used. This range includes the wavelengths that activate mitochondria in vitro, and that have effects in animal models. These wavelengths also include the predominant bands that can penetrate into the body.

Transmission in Human Brain

Power density measurements have been made to determine the transmission of laser light having a wavelength of approximately 808 nanometers through successive layers of human brain tissue. Laser light having a wavelength of (808±5) nanometers with a maximum output of approximately 35 Watts was applied to the surface of the cortex using a beam delivery system which approximated the beam profile after the laser light passes through the human skull. Peak power density measurements were taken through sections of human brain tissue using an Ocean Optics spectrophotometer Model USB 2000, Serial No. G1965 and beam diameter after scattering was approximated using a Sony Model DCR-IP220, Serial No. 132289.

A fresh human brain and spinal cord specimen (obtained within six hours after death) was collected and placed in physiologic Dakins solution. The pia layer, arachnoid layer, and vasculature were intact. The brain was sectioned in the midline sagittally and the section was placed in a container and measurements taken at thicknesses of 4.0 centimeters (±0.5 centimeter), 2.5 centimeters (±0.3 centimeter), and 1.5 centimeters (±0.2 centimeter). The power density measurements are shown in Table 2:

TABLE 2

| Thickness | Power density at cortex | Average power density at thickness |
|---|---|---|
| 4.0 cm | 20 mW/cm$^2$ | 4.9 µW/cm$^2$ |
| 2.5 cm | 20 mW/cm$^2$ | 20 µW/cm$^2$ |
| 1.5 cm | 10 mW/cm$^2$ | 148 µW/cm$^2$ |

Figure 41:
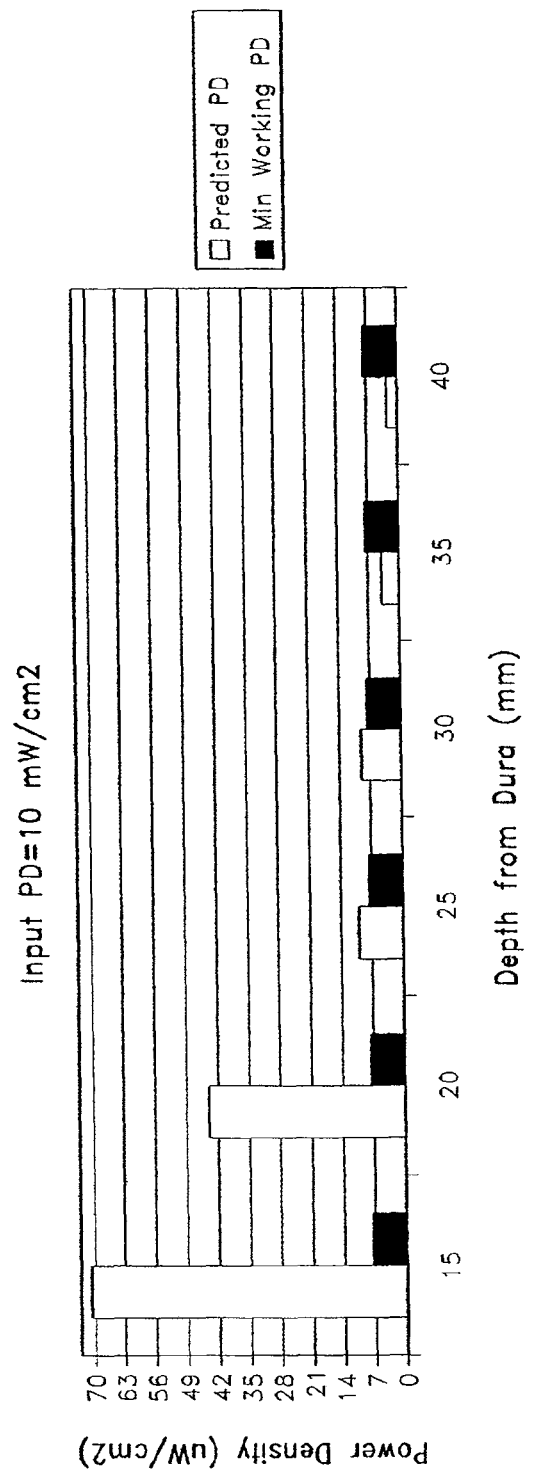
FIG. 41 is a graph of the power density versus the depth from the dura for an input power density of 10 mW/cm$^2$.
Figure 42:
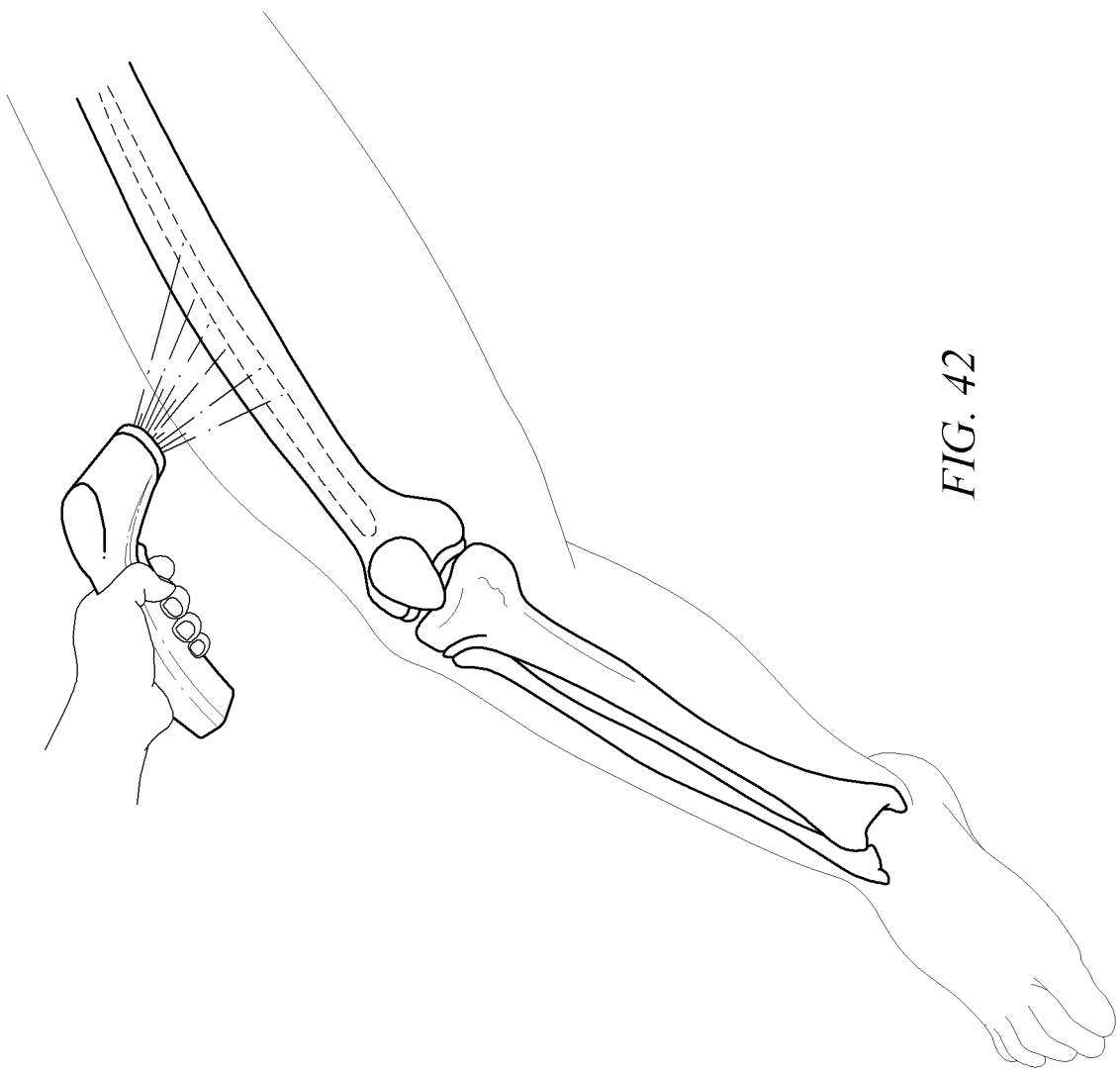
FIG. 42 depicts a laser device used in accordance with several embodiments described herein. In particular.

FIG. 41 is a graph of the power density versus the depth from the dura for an input power density of 10 mW/cm$^2$ with the light bars corresponding to predicted values of the power density and dark bars corresponding to an estimated minimum working power density of 7.5 µW/cm$^2$, as described below.

Based upon prior animal experimentation, a conservative estimation of the minimum known power density within the tissue of the brain which is able to show efficacy in stroke animal models is 7.5 µW/cm$^2$. This estimated minimum working power density is drawn from an experiment in which 10 mW was applied to the rat brain surface, and 7.5 µW/cm$^2$ power density was directly measured 1.8 centimeters from the surface. This stroke model consistently produced significant efficacy, including for strokes 1.8 centimeters from the laser probe. Note that this 7.5 µW/cm$^2$ is a conservative estimate; the same power density at the brain surface also consistently produces significant efficacy in the 3 centimeter rabbit clot shower model. Note also that the power density measurements in the human brain experiment do not factor in the effect from the CNS-filled sulci, through which the laser energy should be readily transmitted. However, even conservatively assuming 7.5 µW/cm$^2$ as the minimum power density hurdle and ignoring expected transmission benefits from the sulci, the experiment described above confirms that approximately 10-15 mW/cm$^2$ transmitted upon the cortex (as per an example dosimetry in man) will be effective to at least 3.0 centimeters from the surface of the brain.

In Vivo Thermal Measurements

In vivo thermal measurements were made to determine the heating effect in living tissue of laser light having a wavelength of approximately 808 nanometers. A GaAlAs laser source of 808-nanometer light was placed in direct contact with the skin of the heads of live rabbits and rats. The laser source had an approximately Gaussian beam profile with a beam diameter of 2.5-4.0 millimeters (1/e$^2$). Thermocouple probes (Model Bat-12 from Physitemp Instruments Inc. of Clifton, N.J.) were placed in the subcutaneous tissue and below the dura and measurements were recorded at various power densities. The results of these measurements are shown in Table 3:

TABLE 3

| Animal | Probe location | Dose | Exposure time | Temperature increase |
|---|---|---|---|---|
| Rat | Subcutaneous | 15 mW/cm$^2$ | 4 minutes | approximately 3° C. |
| Rat | Subdural | 15 mW/cm$^2$ | 4 minutes | approximately 1° C. |
| Rat | Subcutaneous | 75 mW/cm$^2$ | 4 minutes | approximately 7° C. |
| Rat | Subdural | 75 mW/cm$^2$ | 4 minutes | approximately 7° C. |
| Rabbit | Subcutaneous | 7.5 mW/cm$^2$ | 5 minutes | less than 0.5° C. |
| Rabbit | Subdural | 7.5 mW/cm$^2$ | 5 minutes | less than 0.5° C. |
| Rabbit | Subcutaneous | 37.5 mW/cm$^2$ | 5 minutes | approximately 5.5° C. |
| Rabbit | Subdural | 37.5 mW/cm$^2$ | 5 minutes | less than 0.5° C. |

There is minimal heating (e.g., less than 0.5° C.) in the subdural region at four times the therapeutic energy density. The "heat sink" effect of living tissue that minimizes possible heating in the cortex is significantly larger in humans than in rats or rabbits, due to the larger heat sink and blood flow volume, which further limits the undesirable effects of heating in the treated region of the brain. Therefore, in certain embodiments described herein, a therapeutic dosage of energy is delivered to the target area of the brain without undesirable heating of the dura.

Treatment of Heat Stroke

In certain embodiments, a method prevents heat stroke in a subject. The term "preventing" in this context includes reducing the severity of a later heat stroke in a subject that has undergone treatment, reducing the incidence of heat stroke in individuals who have undergone treatment, as well as reducing the likelihood of onset heat stroke in a subject that has undergone treatment. The method includes delivering light energy having a wavelength in the visible to near-infrared wavelength range through the skull to at least one area of the brain of a subject, wherein the wavelength, power density and amount of the light energy delivered are sufficient to prevent, reduce the severity, or reduce the incidence of heat stroke in the subject.

EXAMPLES

Example 1: Effect of Phototherapy on ATP Production in Neurons

An in vitro experiment was done to demonstrate one effect of phototherapy on neurons, namely the effect on ATP production. Normal Human Neural Progenitor (NHNP) cells were obtained cryopreserved through Clonetics of Baltimore, Md., catalog #CC-2599. The NHNP cells were thawed and cultured on polyethyleneimine (PEI) with reagents provided with the cells, following the manufacturers' instructions. The cells were plated into 96 well plates (black plastic with clear bottoms, Becton Dickinson of Franklin Lakes, N.J.) as spheroids and allowed to differentiate into mature neurons over a period of two weeks.

A Photo Dosing Assembly (PDA) was used to provide precisely metered doses of laser light to the NHNP cells in the 96 well plates. The PDA included a Nikon Diaphot inverted microscope (Nikon of Melville, N.Y.) with a LUDL motorized x,y,z stage (Ludl Electronic Products of Hawthorne, N.Y.). An 808 nanometer laser was routed into the rear epi-fluorescent port on the microscope using a custom designed adapter and a fiber optic cable. Diffusing lenses were mounted in the path of the beam to create a "speckled" pattern, which was intended to mimic in vivo conditions after a laser beam passed through human skin. The beam diverged to a 25 millimeter diameter circle when it reached the bottom of the 96 well plates. This dimension was chosen so that a cluster of four adjacent wells could be lased at the same time. Cells were plated in a pattern such that a total of 12 clusters could be lased per 96 well plate. Stage positioning was controlled by a Silicon Graphics workstation and laser timing was performed by hand using a digital timer. The measured power density passing through the plate for the NHNP cells was 50 mW/cm$^2$.

Two independent assays were used to measure the effects of 808 nanometer laser light on the NHNP cells. The first was the CellTiter-Glo Luminescent Cell Viability Assay (Promega of Madison, Wis.). This assay generates a "glow-type" luminescent signal produced by a luciferase reaction with cellular ATP. The CellTiter-Glo reagent is added in an amount equal to the volume of media in the well and results in cell lysis followed by a sustained luminescent reaction that was measured using a Reporter luminometer (Turner Biosystems of Sunnyvale, Calif.). Amounts of ATP present in the NHNP cells were quantified in Relative Luminescent Units (RLUs) by the luminometer.

The second assay used was the alamarBlue assay (Biosource of Camarillo, Calif.). The internal environment of a proliferating cell is more reduced than that of a non-proliferating cell. Specifically, the ratios of NADPH/NADP, FADH/FAD, FMNH/FMN and NADH/NAD, increase during proliferation. In several embodiments, laser irradiation may have an effect on one or more of these ratios. Compounds such as alamarBlue are reduced by these metabolic intermediates and can be used to monitor cellular states. The oxidization of alamarBlue is accompanied by a measurable shift in color. In its unoxidized state, alamarBlue appears blue; when oxidized, the color changes to red. To quantify this shift, a 340PC microplate reading spectrophotometer (Molecular Devices of Sunnyvale, Calif.) was used to measure the absorbance of a well containing NHNP cells, media and alamarBlue diluted 10% v/v. The absorbance of each well was measured at 570 nanometers and 600 nanometers and the percent reduction of alamarBlue was calculated using an equation provided by the manufacturer.

The two metrics described above, (RLUs and % Reduction) were then used to compare NHNP culture wells that had been lased with 50 mW/cm$^2$ at a wavelength of 808 nanometers. For the CellTiter-Glo assay, 20 wells were lased for 1 second and compared to an unlased control group of 20 wells. The CellTiter-Glo reagent was added 10 minutes after lasing completed and the plate was read after the cells had lysed and the luciferase reaction had stabilized. The average RLUs measured for the control wells was 3808+/−3394 while the laser group showed a two-fold increase in ATP content to 7513+/−6109. The standard deviations were somewhat high due to the relatively small number of NHNP cells in the wells (approximately 100 per well from visual observation), but a student's unpaired t-test was performed on the data with a resulting p-value of 0.02 indicating that the two-fold change is statistically significant.

The alamarBlue assay was performed with a higher cell density and a lasing time of 5 seconds. The plating density (calculated to be between 7,500-26,000 cells per well based on the certificate of analysis provided by the manufacturer) was difficult to determine since some of the cells had remained in the spheroids and had not completely differentiated. Because plating conditions were identical, wells from the same plate were compared. The alamarBlue was added immediately after lasing and the absorbance was measured 9.5 hours later. The average measured values for percent reduction were 22%+/−7.3% for the 8 lased wells and 12.4%+/−5.9% for the 3 unlased control wells (p-value=0.076). Thus, in several embodiments, the laser treatment results in a positive metabolic effect in the lased cells.

Several embodiments of the invention increase ATP concentrations, and are particularly advantageous because increases in cellular ATP concentration and a more reduced state within the cell are both related to cellular metabolism and are considered to be indications that the cell is viable and healthy. In some embodiments, positive effects of laser irradiation on cellular metabolism in in-vitro neuronal cell cultures are achieved.

Example 2: Transcranial Laser Therapy for Treatment of Stroke

In a second set of experiments, transcranial laser therapy for stroke was investigated using a low-energy infrared laser to treat behavioral deficits in a rabbit small clot embolic stroke model (RSCEM). This example is described in more detail by P. A. Lapchak et al., "*Transcranial Infrared Laser Therapy Improves Clinical Rating Scores After Embolic Strokes in Rabbits,*" Stroke, Vol. 35, pp. 1985-1988 (2004), which is incorporated in its entirety by reference herein.

RSCEM was produced by injection of blood clots into the cerebral vasculature of anesthetized male New Zealand White rabbits, resulting in ischemia-induced behavioral deficits that can be measured quantitatively with a dichotomous rating scale. In the absence of treatment, small numbers of microclots caused no grossly apparent neurologic dysfunction while large numbers of microclots invariably caused encephalopathy or death. Behaviorally normal rabbits did not have any signs of impairment, whereas behaviorally abnormal rabbits had loss of balance, head leans, circling, seizure-type activity, or limb paralysis.

For laser treatment, a laser probe was placed in direct contact with the skin. The laser probe comprised a low-energy laser (wavelength of 808±5 nanometers) fitted with an OZ Optics Ltd. fiber-optic cable and a laser probe with a diameter of approximately 2 centimeters. Instrument design studies showed that these specifications would allow for laser penetration of the rabbit skull and brain to a depth of 2.5 to 3 centimeters, and that the laser beam would encompass the majority of the brain if placed on the skin surface posterior to bregma on the midline. Although the surface skin temperature below the probe was elevated by up to 3° C., the focal brain temperature directly under the laser probe was increased by 0.8° C. to 1.8° C. during the 10-minute laser treatment using the 25 mW/cm$^2$ energy setting. Focal brain temperature returned to normal within 60 minutes of laser treatment.

The quantitative relationship between clot dose and behavioral or neurological deficits was evaluated using logistic (S-shaped) curves fitted by computer to the quantal dose-response data. These parameters are measures of the amount of microclots (in mg) that produced neurologic dysfunction in 50% of a group of animals ($P_{50}$). A separate curve was generated for each treatment condition, with a statistically significant increase in the $P_{50}$ value compared with control being indicative of a behavioral improvement. The data were analyzed using the t test, which included the Bonferroni correction when appropriate.

To determine if laser treatment altered physiological variables, 14 rabbits were randomly divided into 2 groups, a control group and a laser-treated group (25 mW/cm$^2$ for 10 minutes). Blood glucose levels were measured for all embolized rabbits using a Bayer Elite XL 3901B Glucometer, and body temperature was measured using a Braun Thermoscan Type 6013 digital thermometer. Within 60 minutes of embolization, there was an increase in blood glucose levels in both the control group and the laser-treated group that was maintained for the 2 hours post-embolization observation time. Blood glucose levels returned to control levels by 24 hours, regardless of the extent of stroke-induced behavioral deficits. Laser treatment did not significantly affect glucose levels at any time. Neither embolization nor laser treatment significantly affected body temperature in either group of rabbits.

Figure 43A:
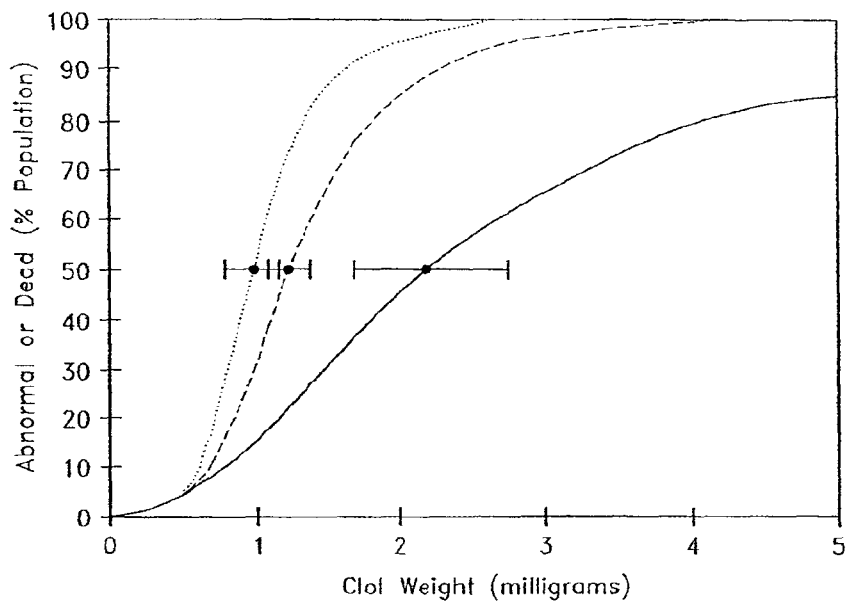
FIG. 43A is a graph of the effects of laser treatment of 7.5 mW/cm$^2$ for a treatment duration of 2 minutes on a population of rabbits having small clot embolic stroke.

FIG. 43A is a graph for the percentage of the population which was either abnormal or dead as a function of the clot weight in milligrams for laser treatment of 7.5 mW/cm$^2$ for a treatment duration of 2 minutes. As shown by FIG. 43A, the control curve (dotted line) has a $P_{50}$ value of 0.97±0.19 mg (n=23). Such laser treatment initiated 3 hours after the stroke significantly improved behavioral performance, with the $P_{50}$ value increased to 2.21±0.54 mg (n=28, *P=0/05) (solid line). The effect was durable and was measurable 3 weeks after embolization. However, the same setting did not improve behavior if there was a long delay (24 hours) after embolization (dashed line) ($P_{50}$=1.23±0.15 mg, n=32).

In several embodiments, as discussed above, LLLT is advantageous if started soon after an injury (e.g., traumatic injury or onset of stroke). In several embodiments, treatment is administered as soon as possible after an injury. In some embodiments, a plurality of additional treatments are made after an initial treatment. In some embodiments, incorporation of a delay before, during, or after therapy (e.g., prior to a second treatment) is beneficial. For example, in some embodiments, improved therapeutic effects are obtained if there a purposeful delay between an injury and the inception of treatment. In some embodiments, outcomes are improved if an immediate treatment is made, followed by a delay prior to a second treatment. In several embodiments, the delay is on the order of hours, for example, between about 1 and 8 hours after an injury, including 1-2 hours, 2-4 hours, 3-5 hours, 4-6 hours, 5-7 hours, and 7-8 hours after injury. In some embodiments, treatment is delayed between about 6 to 24 hours after injury (including 6-8 hours, 8-10 hours, 10-12 hours, 12-14 hours, 14-18 hours, 18-20 hours, 20-22 hours and 22-24 hours, and overlapping ranges thereof). In some embodiments, treatment is delayed from 24-48 hours. In several embodiments the delays are tailored to the response characteristics of an individual patient (e.g., tailored therapy).

Figure 43B:
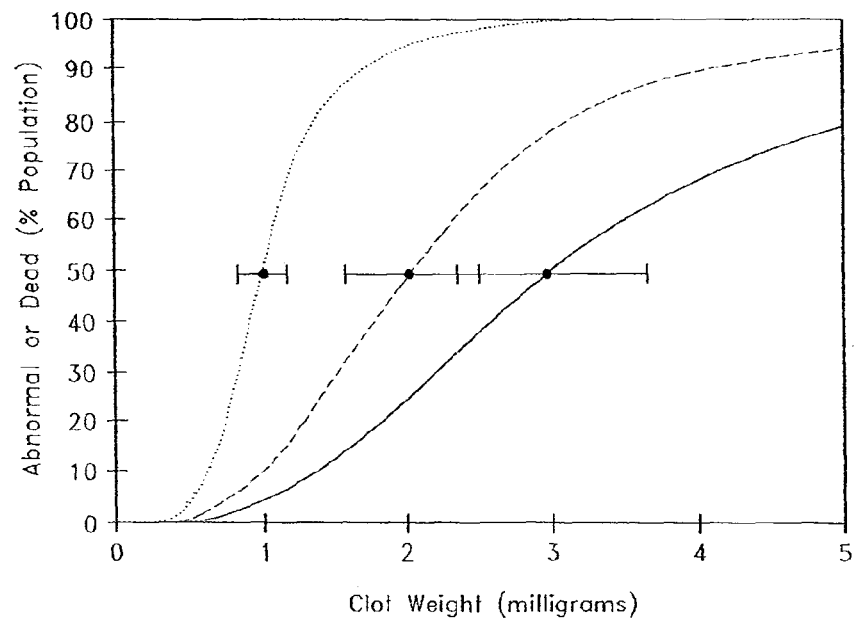
FIG. 43B is a graph of the effects of laser treatment of 25 mW/cm$^2$ for a treatment duration of 10 minutes on a population of rabbits having small clot embolic stroke.

FIG. 43B is a graph for the percentage of the population which was either abnormal or dead as a function of the clot weight in milligrams for laser treatment of 25 mW/cm2 for a treatment duration of 10 minutes. As shown by FIG. 43B, the control curve (dotted line) has a $P_{50}$ value of 1.10±0.17 mg (n=27). Such laser treatment initiated 1 (dashed line) or 6 (solid line) hours after embolization also significantly increased behavioral performance, with the $P_{50}$ value increased to 2.02±0.46 mg (n=18, *P<0.05) and 2.98±0.65 mg (n=26, *P<0.05), respectively.

Figure 44:
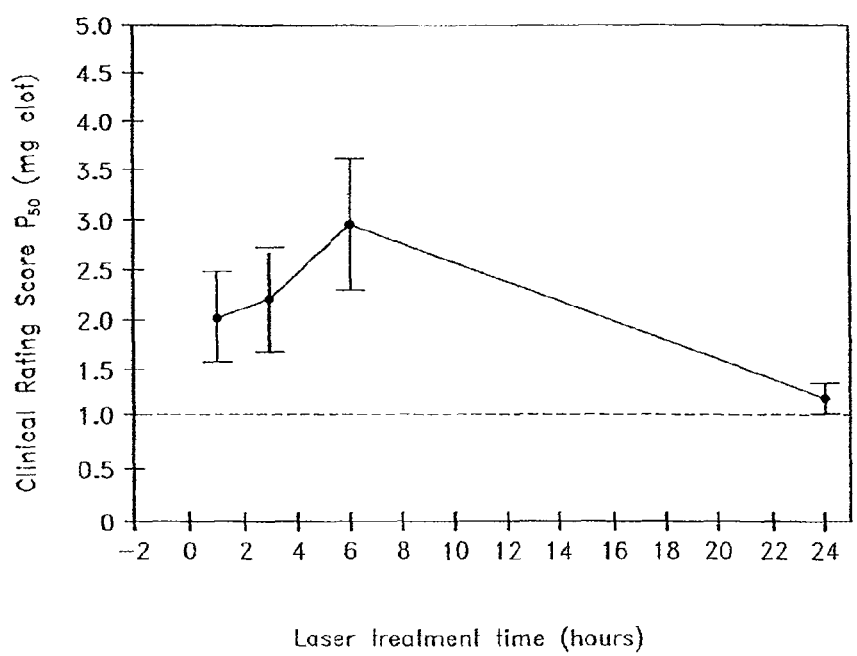
FIG. 44 is a graph showing the therapeutic window for laser-induced behavioral improvements after small-clot embolic strokes in rabbits.

FIG. 44 is a graph showing the therapeutic window for laser-induced behavioral improvements after small-clot embolic strokes in rabbits. Results are shown as clinical rating score $P_{50}$ (mg clot) given as mean±SEM for the number of rabbits per time point (number in brackets) for laser treatment initiated 1, 3, 6, or 24 hours after embolization as shown on the x-axis. The horizontal line represents the mean of the control $P_{50}$ values (*P<0.05).

The results in the RSCEM showed that laser treatment significantly improved behavioral rating scores after embolic strokes in rabbits without affecting body temperature and blood glucose levels. In addition, laser treatment was effective when initiated up to 6 hours after strokes, which is later than any other previously effective single therapy in the same preclinical stroke model. Moreover, the effect was durable and was measurable up to 21 days after embolization. In several embodiments, LLLT provides a viable therapeutic regime for the treatment of stroke (or other brain/neural injuries) that results in long-lasting improvements (e.g., recoveries) in neurological function. The magnitudes of laser-induced improvement in rabbits are similar to previously tested thrombolytics (alteplase, tenecteplase, and microplasmin) and neuroprotective compounds (NXY-059), which are undergoing clinical development. Thus, several embodiments are particularly advantageous as an alternative or supplement to pharmacological therapies. In some embodiments, LLLT works synergistically with pharmacological therapies. For example, in one embodiment, LLLT enhances the therapeutic effect of a given dose of a drug. In another embodiment, LLLT reduces the dose of a drug needed to achieve a comparable effect.

Example 3: LLLT in Combination with Neural Stem Cells to Treat Neurodegeneration Given the propensity of neurological disorders or acute neural injury to induce a loss of function of one or more neural cells, and the disclosure herein regarding the positive effects of LLLT on cells, in particular neural stem cells, the present experiment will be directed to the combination of LLLT and neural stem cell therapy. Cultured healthy neurons will be used to investigate the effects of LLLT and neural stem cell therapy in combination.

Multiple populations of healthy neurons will be cultured under standard sterile tissue culture conditions. A population of healthy neurons will be exposed to rotenone, a chemical stimulus that induces a loss of function in the neurons and is an accepted model for Parkinson's disease, while another population will be maintained under original conditions as a control. The rotenone exposed neurons will exhibit loss of one or more functional endpoints as compared to the control neurons (e.g., diminished action potential duration, diminished neurotransmitter release).

Multiple populations of neural progenitor (stem) cells will also be cultured. A population of neural progenitors will be exposed to LLLT according to parameters disclosed herein. Another population will be maintained unexposed as a control. In one embodiment, LLLT exposure will enhance the viability of the neural progenitors. In one embodiment, the LLLT exposure will enhance the ability of the neural progenitor cells to differentiate based on the environmental cues (e.g., growth factors or differentiation-inducing agents in vitro or in vivo).

LLLT-exposed and unexposed neural progenitor cells will be co-cultured with healthy and rotenone-treated neurons. In several embodiments, the enhanced differentiation of the LLLT-treated cells will increase the number of neural progenitor cells that differentiate into neurons of the same type as in the co-culture. As a result, in one embodiment, rotenone-treated neurons co-cultured with LLLT-treated neural progenitor cells will exhibit recovery from the rotenone-induced loss of function. The recovery will be enhanced as compared to the co-culture employing non-LLLT treated neural progenitors.

In vivo experiments will also be performed. Control and rotenone-treated rats will be used. Rotenone-treated rats will exhibit loss of function as assessed by clinical endpoints for evaluation of Parkinson's disease (e.g., motor control and behavioral tests). LLLT-treated or control neural progenitor cells are stereotactically administered to the substantia nigra of control and rotenone-treated rats. In several embodiments, rotenone-treated rats receiving LLLT-treated neural progenitor cells will exhibit increased motor control and improved clinical assessment scores. In one embodiment, immunohistochemical analysis of brains of rotenone-treated rats receiving LLLT-treated neural progenitor cells will reveal a larger percentage of LLLT-treated neural progenitor cells differentiated into functional neurons, thereby replacing the rotenone-damaged neurons, and accounting for the increased efficacy of cell therapy.

In one embodiment, similar results will be obtained when LLLT-treated progenitors are administered to Alzheimer's rats (e.g., Samaritan FAB Rat Model).

Example 4: LLLT in Combination with Neural Stem Cells to Treat Acute Neural Injury In an additional experiment, rabbits will be subjected to traumatic brain injury (TBI) according to an art-recognized model (e.g., controlled mass weight drop) and will be treated with the combination of stem cells and LLLT. A group of healthy rabbits will be used as a control. Another group of TBI rabbits that do not receive cells will serve as another control. TBI rabbits will exhibit neural damages as assessed by standard neurological severity scales. Neural progenitor cells will be cultured and treated as described above. LLLT-treated and untreated neural stem cells will be administered to healthy and TBI rabbits. In several embodiments, TBI rabbits receiving LLLT-treated neural stem cells will exhibit improved neurological scores as compared to TBI rabbits which did not receive cells. Further, TBI rabbits receiving LLLT-treated neural stem cells will exhibit enhanced recovery of function as compared to TBI rabbits receiving untreated stem cells. In one embodiment, immunohistochemical analysis of brains of TBI rabbits receiving LLLT-treated neural stem cells will reveal that a larger percentage of LLLT-treated neural stem cells differentiated into functional neurons, thereby replacing the TBI-damaged neurons, and accounting for the increased efficacy of cell therapy.

In one embodiment, similar results are achieved when LLLT-treated neural progenitor cells are administered to rabbits receiving surgically induced ischemic stroke.

Example 5: LLLT Treatment of Progenitor Cells Enhances the Therapeutic Potential of the Cells As discussed above, increasing the therapeutic efficacy of cell therapy is desirable. In an additional experiment, LLLT will be administered to cultured neural stem cells according to parameters disclosed herein. Another population of neural stem cells will serve as an untreated control. In several embodiments, LLLT treatment will increase the response of the stem cells to pro-differentiation factors (e.g., growth factors) as compared to the control cells. In several embodiments, LLLT treatment will also improve the ability of the stem cells to survive in adverse growth conditions (e.g., hypoxia, lack of essential growth nutrient). In some embodiments, LLLT treated cells will respond to chemoattractants to a greater degree than control cells, indicating enhanced migratory capacity. In some embodiments, injection of LLLT-treated stem cells into a host tissue (e.g. muscle, brain) will yield a higher degree of engraftment as compared to untreated cells. Improvement in each of these parameters will indicate that stem cells have increased therapeutic potential.

Various embodiments have been described above. Although this invention has been described with reference to these specific embodiments, the descriptions are intended to be illustrative of the invention and are not intended to be limiting. Various modifications and applications may occur to those skilled in the art without departing from the true spirit and scope of the invention.

What is claimed is:

1. A method for enhancing the efficacy of stem cell therapy in a mammal comprising:
    identifying a mammal having neural tissue with an impaired function;
    administering one or more stem cells to said tissue;
    providing a low level light therapy (LLLT) device, wherein said LLLT device has a light emitting surface that emits light energy; and
    delivering light energy to said tissue,
    wherein the light energy has a wavelength between 630 nm and 904 nm, and
    wherein the light energy enhances one or more of an engraftment and migration of said administered stem cells.

2. The method of claim 1, wherein the impaired function is due to degenerative neural disease.

3. The method of claim 2, wherein the degenerative neural disease is selected form the group consisting of Parkinson's disease, Alzheimer's disease, Huntington's disease, dopaminergic impairment, and dementia.

4. The method of claim 1, wherein the impaired neural function is a result of injury to a neuron.

5. The method of claim 1, further comprising delivering said light energy to said stem cells prior to administering said stem cells to said tissue.

6. The method of claim 1, wherein delivering said light energy to said tissue comprises delivering said light energy to said stem cells after administering said stem cells to said tissue.

7. The method of claim 1, wherein the administered stem cells comprise mesenchymal stem cells.

8. The method of claim 7, wherein said mesenchymal stem cells are allogeneic to said mammal.

9. The method of claim 1, wherein said light energy is pulsed.

\* \* \* \* \*